(12) United States Patent
Monia et al.

(10) Patent No.: US 9,796,976 B2
(45) Date of Patent: Oct. 24, 2017

(54) METHODS AND COMPOSITIONS FOR MODULATING ALPHA-1 ANTITRYPSIN EXPRESSION

(71) Applicant: Ionis Pharmaceuticals, Inc., Carlsbad, CA (US)

(72) Inventors: Brett P. Monia, Encinitas, CA (US); Michael L. McCaleb, La Jolla, CA (US); Susan M. Freier, San Diego, CA (US); Shuling Guo, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 15/097,471

(22) Filed: Apr. 13, 2016

(65) Prior Publication Data
US 2016/0362687 A1   Dec. 15, 2016

Related U.S. Application Data

(63) Continuation of application No. 14/386,246, filed as application No. PCT/US2013/033004 on Mar. 19, 2013, now Pat. No. 9,340,784.

(60) Provisional application No. 61/649,075, filed on May 18, 2012, provisional application No. 61/612,793, filed on Mar. 19, 2012.

(51) Int. Cl.
| | |
|---|---|
| *A61K 48/00* | (2006.01) |
| *C12N 15/11* | (2006.01) |
| *C07H 21/02* | (2006.01) |
| *C07H 21/04* | (2006.01) |
| *C12N 15/113* | (2010.01) |
| *A61K 31/7115* | (2006.01) |
| *A61K 31/712* | (2006.01) |
| *A61K 31/7125* | (2006.01) |
| *C07K 14/81* | (2006.01) |

(52) U.S. Cl.
CPC .......... *C12N 15/113* (2013.01); *A61K 31/712* (2013.01); *A61K 31/7115* (2013.01); *A61K 31/7125* (2013.01); *C07K 14/8125* (2013.01); *C12N 2310/11* (2013.01); *C12N 2310/315* (2013.01); *C12N 2310/321* (2013.01); *C12N 2310/3231* (2013.01); *C12N 2310/3233* (2013.01); *C12N 2310/3341* (2013.01); *C12N 2310/341* (2013.01); *C12N 2310/346* (2013.01)

(58) Field of Classification Search
USPC .......................... 514/44; 536/23.1, 24.3, 24.5
See application file for complete search history.

(56) References Cited

U.S. PATENT DOCUMENTS

| | | | |
|---|---|---|---|
| 7,339,051 B2 * | 3/2008 | Crooke | C07K 16/10 536/23.1 |
| 9,340,784 B2 * | 5/2016 | Monia | A61K 31/7115 |
| 2005/0137153 A1 * | 6/2005 | McSwiggen | A61K 49/0008 514/44 A |

* cited by examiner

*Primary Examiner* — Terra C Gibbs
(74) *Attorney, Agent, or Firm* — Ionis Pharmaceuticals, Inc. Patent Dept.

(57) ABSTRACT

Disclosed herein are methods for decreasing A1AT mRNA and protein expression and treating, ameliorating, preventing, slowing progression, or stopping progression of fibrosis. Disclosed herein are methods for decreasing A1AT mRNA and protein expression and treating, ameliorating, preventing, slowing progression, or stopping progression of liver disease, such as, A1ATD associated liver disease, and pulmonary disease, such as, A1ATD associated pulmonary disease in an individual in need thereof. Methods for inhibiting A1AT mRNA and protein expression can also be used as a prophylactic treatment to prevent individuals at risk for developing a liver disease, such as, A1ATD associated liver disease and pulmonary disease, such as, A1ATD associated pulmonary disease.

18 Claims, No Drawings

METHODS AND COMPOSITIONS FOR MODULATING ALPHA-1 ANTITRYPSIN EXPRESSION

SEQUENCE LISTING

The present application is being filed along with a Sequence Listing in electronic format. The Sequence Listing is provided as a file entitled BIOL0163USC1SEQ_ST25.txt created Apr. 12, 2016, which is 108 Kb in size. The information in the electronic format of the sequence listing is incorporated herein by reference in its entirety.

FIELD

Provided are methods and compositions for reducing expression of alpha-1 antitrypsin (A1AT) mRNA and protein in an animal. Such methods and compositions are useful for treating, ameliorating, preventing, slowing progression, or stopping progression of diseases, disorders, and conditions associated with alpha-1 antitrypsin deficiency (A1ATD). Such diseases, disorders, and conditions associated with A1ATD include liver diseases, such as alpha-1 antitrypsin deficiency (A1ATD) associated liver disease, and pulmonary diseases, such as A1ATD pulmonary disease.

BACKGROUND

Alpha-1 antitrypsin (also known as $\alpha_1$-antitrypsin or A1AT) is a 52 kD serpin glycoprotein produced in hepatocytes and in smaller quantities in phagocytes and lung epithelial cells (Gettins, P. G. Chem. Rev. 2002. 102: 4751-4804). A1AT is a protease inhibitor.

A1AT deficiency (A1ATD) is a genetic disorder associated with the development of liver and lung disease (Bals, R. Best Pract. Res. Clin. Gastroenterol. 2010. 24: 629-633). A1AT deficiency is caused by homozygosity for the A1AT mutant Z gene and occurs in 1 in 2,000 births in many North American and European populations (Teckman, J. H. Semin. Liver Dis. 2007. 27: 274-281). Additionally, recent studies have suggested that the PiZ heterozygous state may be associated with increased severity and worse outcome in liver disease of known etiologies, such as HCV, alcoholic liver disease (ALD) or NAFLD (Regev A. J. Pediatr. Gastroenterol. Nutr. 2006. 43: S30-S35). In the most common genetic deficiency (PiZ, resulting from a mutation of glutamate to lysine at position 342 of the gene), there is accumulation of A1AT in the liver as a result of polymer formation (Stockley, R. A. Expert Opin. Emerg. Drugs. 2010. 15: 685-694). The abnormal mutant protein accumulates within the endoplasmic reticulum of hepatocytes as intrahepatocytic globules. The result of this intracellular accumulation in homozygous ZZ individuals is an increased risk of chronic liver disease and hepatocellular carcinoma (Perlmutter, D. H. et al., Hepatology. 2007. 45: 1313-1323; Teckman, J. H. et al., Curr. Gastroenterol. Rep. 2006. 8: 14-20; Eriksson, S. et al., Am. J. Respir. Crit. Care Med. 2003. 168: 856-869). There are no specific treatments for A1ATD associated liver disease, other than liver transplantation.

A1AT deficiency also predisposes individuals to the development of chronic obstructive pulmonary disease (COPD) and emphysema. In the absence of wild-type A1AT, neutrophil elastase is free to break down elastin, which contributes to the elasticity of the lungs, resulting in respiratory disorders (DeMeo, D. L. and Silverman, E. K. Thorax. 2004. 59: 259-264). Also, in such patients, there is an excess of mutant A1AT polymers, which are bound to the alveolar wall. This enables the polymers to act as a chronic stimulus for neutrophil influx in the lungs of A1AT deficient individuals (Mahadeva, R. et al., Am. J. Pathobiol. 2005. 166: 377-387).

Described herein are compositions and methods for modulating A1AT expression. The compounds and treatment methods described herein provide significant advantages over the treatments options currently available for A1AT-related disorders.

SUMMARY

Provided herein are compounds that modulate expression of A1AT mRNA and protein.

Certain embodiments describe compounds. In certain embodiments, the compound is an antisense compound. In certain embodiments, the compound comprises an oligonucleotide. In certain embodiments, the oligonucleotide is an antisense oligonucleotide. In certain embodiments, the oligonucleotide is a modified oligonucleotide. In certain embodiments, the oligonucleotide is a modified antisense oligonucleotide. In certain embodiments, the compound comprises a modified oligonucleotide consisting of 12 to 30 linked nucleosides and having a nucleobase sequence comprising at least 8 contiguous nucleobases of a sequence set out in the sequence listing as one of SEQ ID NOs: 20-41. Certain embodiments describe a composition comprising a compound. In certain embodiments, the composition comprises a compound according to any of the embodiments as described herein or a salt thereof and a pharmaceutically acceptable carrier or diluent.

In certain embodiments, provided are compounds and compositions according to any of the embodiments as described herein for use in therapy.

Provided herein are methods for modulating expression of A1AT mRNA and protein. In certain embodiments, A1AT specific inhibitors modulate expression of A1AT mRNA and protein. In certain embodiments, A1AT specific inhibitors are nucleic acids, proteins, or small molecules.

In certain embodiments, modulation can occur in a cell or tissue. In certain embodiments, the cell or tissue is in an animal. In certain embodiments, the animal is a human. In certain embodiments, A1AT mRNA levels are reduced. In certain embodiments, A1AT protein levels are reduced. In certain embodiments, A1AT mRNA and protein levels are reduced. In certain embodiments, mutant A1AT mRNA and protein levels are reduced. Such reduction can occur in a time-dependent manner or in a dose-dependent manner.

Also provided are methods useful for treating, ameliorating, preventing, slowing progression, or stopping progression of diseases, disorders, and conditions associated with A1ATD. In certain embodiments, such diseases, disorders, and conditions associated with A1ATD include liver diseases, such as alpha-1 antitrypsin deficiency (A1ATD) associated liver disease, viral liver disease, and nonalcoholic steatohepatitis (NASH). In certain embodiments, A1ATD exacerbates underlying liver diseases. In certain embodiments, diseases, disorders, and conditions associated with A1ATD include pulmonary diseases, such as alpha-1 antitrypsin deficiency (A1ATD) associated pulmonary disease, chronic obstructive pulmonary disease (COPD), and emphysema. In certain embodiments, A1ATD exacerbates underlying pulmonary diseases.

Diseases, disorders, and conditions associated with A1ATD can have one or more risk factors, causes, or outcomes in common. Certain risk factors and causes for development of diseases, disorders, and conditions associated with A1ATD include genetic predisposition to alpha-1 antitrypsin deficiency. In certain embodiments, a defect in an individual's genetic code for alpha-1 antitrypsin (A1AT) is responsible for diseases, disorders, and conditions associated with A1ATD, such as, liver diseases and pulmonary diseases. In certain embodiments, genetic mutations lead to expression of mutant A1AT. In certain embodiments, mutant A1AT forms aggregates which are retained in the liver, causing liver dysfunction or hepatic toxicity. Certain outcomes associated with liver disease, including A1ATD associated liver disease, include abdominal swelling or pain, bruising easily, dark urine, light colored stools, itching all over the body, vomiting blood, passing bloody or black stools, jaundice, lack of normal weight and height gain in children, liver cirrhosis, and death. In certain embodiments, mutant A1AT forms aggregates which are retained in the lung, causing pulmonary dysfunction or pulmonary disease. Certain outcomes associated with pulmonary disease, including A1ATD associated pulmonary disease, include chronic cough, fatigue, respiratory infections, shortness of breath (dyspnea), wheezing, pulmonary hypertension, heart disease, and death.

In certain embodiments, methods of treatment include administering an A1AT specific inhibitor to an individual in need thereof. In certain embodiments, the A1AT specific inhibitor is a nucleic acid. In certain embodiments, the nucleic acid is an antisense compound. In certain embodiments, the antisense compound is a modified oligonucleotide. In certain embodiments, the modified oligonucleotide reduces A1AT protein levels, which alleviates hepatic toxicity induced by protein aggregates. In certain embodiments, the modified oligonucleotide reduces A1AT protein in the liver. In certain embodiments, the modified oligonucleotide reduces A1AT protein levels, which alleviates pulmonary dysfunction induced by protein aggregates. In certain embodiments, the modified oligonucleotide reduces A1AT protein in the lung. In certain embodiments, the A1AT protein is mutant A1AT protein.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position of the furanosyl ring other than H or OH. In certain embodiments, 2' substituted nucleosides include nucleosides with bicyclic sugar modifications.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5' position. A 5-methylcytosine is a modified nucleobase.

"A1AT nucleic acid" or "alpha-1 antitrypsin nucleic acid" means any nucleic acid encoding A1AT. For example, in certain embodiments, a A1AT nucleic acid includes a DNA sequence encoding A1AT, an RNA sequence transcribed from DNA encoding A1AT (including genomic DNA comprising introns and exons), and an mRNA sequence encoding A1AT. "A1AT mRNA" means an mRNA encoding an A1AT protein.

"A1AT specific inhibitor" refers to any agent capable of specifically inhibiting the expression of A1AT mRNA and/or A1AT protein at the molecular level. For example, A1AT specific inhibitors include nucleic acids (including antisense compounds), peptides, antibodies, small molecules, and other agents capable of inhibiting the expression of A1AT mRNA and/or A1AT protein.

"A1ATD" or "alpha-1 antitrypsin deficiency" means lack of sufficient A1AT necessary for normal function. A1ATD may occur due to expression of mutant A1AT, which is characterized by abnormal folding of the protein, which may cause A1AT to aggregate in a patient's liver, thus, allowing only small amounts of A1AT to be released into the blood.

"A1ATD associated liver disease" or "alpha-1 antitrypsin deficiency associated liver disease" means liver dysfunction and/or hepatic toxicity associated with alpha-1 antitrypsin deficiency. Symptoms and outcomes of A1ATD associated liver disease include abdominal swelling or pain, bruising easily, dark urine, light colored stools, itching all over his body, vomiting blood, passing bloody or black stools, jaundice, lack of normal weight and height gain in children, liver cirrhosis, and death. Although not limited by mechanism, it is theorized that A1ATD is caused by a mutant form of A1AT which forms protein aggregates that are retained in a patient's liver. The presence of such aggregates interferes with proper function of the liver resulting in liver dysfunction and hepatic toxicity. Examples of A1ATD associated liver diseases include, but are not limited to, cirrhosis and liver cancer.

"A1ATD associated pulmonary disease" or "alpha-1 antitrypsin deficiency associated pulmonary disease" means pulmonary dysfunction associated with alpha-1 antitrypsin deficiency. Symptoms and outcomes of A1ATD associated pulmonary disease include chronic cough, fatigue, respiratory infections, shortness of breath (dyspnea), wheezing, pulmonary hypertension, heart disease, and death. Although not limited by mechanism, it is theorized that A1ATD is caused by a mutant form of A1AT which forms protein aggregates that are retained in a patient's lungs. The presence of such aggregates interferes with proper function of the lungs resulting in lung dysfunction. Examples of A1ATD associated pulmonary diseases include, but are not limited to, chronic obstructive pulmonary diseases (COPD) such as chronic bronchitis or emphysema.

"About" means within ±7% of a value. For example, if it is stated, "the compounds affected at least about 70% inhibition of A1AT", it is implied that the A1AT levels are inhibited within a range of 63% and 77%.

"Active pharmaceutical agent" means the substance or substances in a pharmaceutical composition that provide a therapeutic benefit when administered to an individual. For example, in certain embodiments an antisense oligonucleotide targeted to A1AT is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Amelioration" or "ameliorate" or "ameliorating" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include, but are not limited to, single-stranded and double-stranded compounds, such as, antisense oligonucleotides, siRNAs and shRNAs.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases. "Bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

"Bicyclic nucleic acid" or "BNA" or "BNA nucleosides" means nucleic acid monomers having a bridge connecting two carbon atoms between the 4' and 2' position of the nucleoside sugar unit, thereby forming a bicyclic sugar. Examples of such bicyclic sugar include, but are not limited to A) α-L-Methyleneoxy (4'-CH$_2$—O-2') LNA, (B) β-D-Methyleneoxy (4'-CH$_2$—O-2') LNA, (C) Ethyleneoxy (4'-(CH$_2$)$_2$—O-2') LNA, (D) Aminooxy (4'-CH$_2$—O—N(R)-2') LNA and (E) Oxyamino (4'-CH$_2$—N(R)—O-2') LNA, as depicted below.

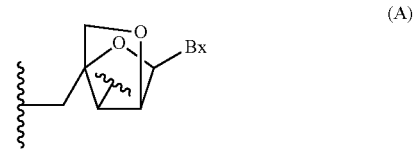

(A)

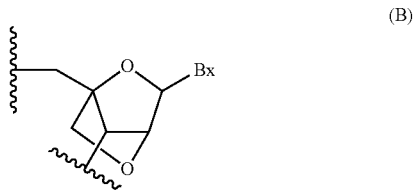

(B)

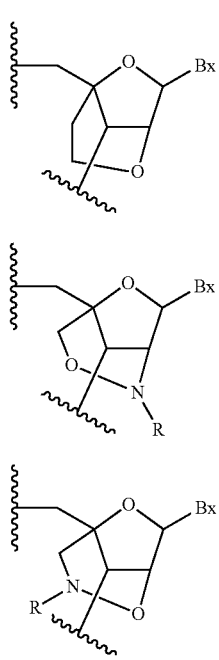

As used herein, LNA compounds include, but are not limited to, compounds having at least one bridge between the 4' and the 2' position of the sugar wherein each of the bridges independently comprises 1 or from 2 to 4 linked groups independently selected from —[C($R_1$)($R_2$)]$_n$—, —C($R_1$)=C($R_2$)—, —C($R_1$)=N—, —C(=N$R_1$)—, —C(=O)—, —C(=S)—, —O—, —Si($R_1$)$_2$—, —S(=O)$_x$— and —N($R_1$)—; wherein: x is 0, 1, or 2; n is 1, 2, 3, or 4; each $R_1$ and $R_2$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, O$J_1$, N$J_1J_2$, S$J_1$, $N_3$, COO$J_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

Examples of 4'-2' bridging groups encompassed within the definition of LNA include, but are not limited to one of formulae: —[C($R_1$)($R_2$)]$_n$—, —[C($R_1$)($R_2$)]$_n$—O—, —C($R_1R_2$)—N($R_1$)—O— or —C($R_1R_2$)—O—N($R_1$)—. Furthermore, other bridging groups encompassed with the definition of LNA are 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N($R_1$)-2' and 4'-CH$_2$—N($R_1$)—O-2'-bridges, wherein each $R_1$ and $R_2$ is, independently, H, a protecting group or $C_1$-$C_{12}$ alkyl.

Also included within the definition of LNA are LNAs in which the 2'-hydroxyl group of the ribosyl sugar ring is connected to the 4' carbon atom of the sugar ring, thereby forming a methyleneoxy (4'-CH$_2$—O-2') bridge to form the bicyclic sugar moiety. The bridge can also be a methylene (—CH$_2$—) group connecting the 2' oxygen atom and the 4' carbon atom, for which the term methyleneoxy (4'-CH$_2$—O-2') LNA is used. Furthermore; in the case of the bicylic sugar moiety having an ethylene bridging group in this position, the term ethyleneoxy (4'-CH$_2$CH$_2$—O-2') LNA is used. α-L-methyleneoxy (4'-CH$_2$—O-2'), an isomer of methyleneoxy (4'-CH$_2$—O-2') LNA is also encompassed within the definition of LNA, as used herein.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Comprise," "comprises" and "comprising" will be understood to imply the inclusion of a stated step or element or group of steps or elements but not the exclusion of any other step or element or group of steps or elements.

"Complementarity" means the capacity for base pairing between nucleobases of a first nucleic acid and a second nucleic acid. "Contiguous nucleobases" means nucleobases immediately adjacent to each other.

"Deoxyribonucleotide" means a nucleotide having a hydrogen at the 2' position of the sugar portion of the nucleotide. Deoxyribonucleotides may be modified with any of a variety of substituents.

"Designing" or "Designed to" refer to the process of designing an oligomeric compound that specifically hybridizes with a selected nucleic acid molecule.

"Downstream" refers to the relative direction toward the 3' end or C-terminal end of a nucleic acid.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to the products of transcription and translation.

"Fibrosis" refers to the formation of fibrous tissue. Excess fibrosis in an organ or tissue can lead to a thickening of the affected area and scar formation. Fibrosis can lead to organ or tissue damage and a decrease in the function of the organ or tissue. Examples of fibrosis include, but is not limited to, cirrhosis (fibrosis of the liver) and pulmonary fibrosis (fibrosis of the lung).

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Gap-widened" means a chimeric antisense compound having a gap segment of 12 or more contiguous 2'-deoxyribonucleosides positioned between and immediately adjacent to 5' and 3' wing segments having from one to six nucleosides.

"Hybridization" means the annealing of complementary nucleic acid molecules. In certain embodiments, complementary nucleic acid molecules include an antisense compound and a target nucleic acid.

"Identifying an animal at risk for developing A1ATD associated liver disease" means identifying an animal having been diagnosed with A1ATD associated liver disease or identifying an animal predisposed to develop A1ATD associated liver disease. Individuals predisposed to develop an A1ATD associated liver disease include those having one or more risk factors for A1ATD associated liver disease, including, having a personal or family history of A1ATD or A1ATD associated liver disease. Such identification may be accomplished by any method including evaluating an individual's medical history and standard clinical tests or assessments, such as genetic testing.

"Identifying an animal at risk for developing A1ATD associated pulmonary disease" means identifying an animal having been diagnosed with A1ATD associated pulmonary disease or identifying an animal predisposed to develop A1ATD associated pulmonary disease. Individuals predisposed to develop an A1ATD associated pulmonary disease include those having one or more risk factors for A1ATD associated pulmonary disease, including, having a personal or family history of A1ATD or A1ATD associated pulmonary disease. Such identification may be accomplished by any method including evaluating an individual's medical history and standard clinical tests or assessments, such as genetic testing.

"Immediately adjacent" means there are no intervening elements between the immediately adjacent elements.

"Individual" means a human or non-human animal selected for treatment or therapy.

"Induce", "inhibit", "potentiate", "elevate", "increase", "decrease", upregulate", "downregulate", or the like, generally denote quantitative differences between two states.

"Inhibiting A1AT" means reducing expression of A1AT mRNA and/or protein levels in the presence of an A1AT specific inhibitor, including an A1AT antisense oligonucleotide, as compared to expression of A1AT mRNA and/or protein levels in the absence of an A1AT specific inhibitor, such as an A1AT antisense oligonucleotide.

"Internucleoside linkage" refers to the chemical bond between nucleosides.

"ISIS number" refers to an A1AT specific inhibitor that is a modified antisense oligonucleotide having the nucleobase sequence specified by the associated SEQ ID NO and the chemistry and motif associated in the related example section. For example, "ISIS 487660" means an A1AT specific inhibitor that is a modified antisense oligonucleotide having the nucleobase sequence (from 5' to 3') "CCAGCTCAAC-CCTTCTTTAA", incorporated herein as SEQ ID NO: 38, a 5-10-5 MOE gapmer, wherein each internucleoside linkage is a phosphorothioate internucleoside linkage and each cytosine is a 5-methylcytosine, and each of nucleosides 1-5 and 16-20 comprise a 2'-O-methoxyethyl sugar moiety. For example, "ISIS 496407" means an A1AT specific inhibitor that is a modified antisense oligonucleotide having the nucleobase sequence (from 5' to 3') "CTTCTTTAATGT-CATCCAGG", incorporated herein as SEQ ID NO: 29, a 5-10-5 MOE gapmer, wherein each internucleoside linkage is a phosphorothioate internucleoside linkage and each cytosine is a 5-methylcytosine, and each of nucleosides 1-5 and 16-20 comprise a 2'-O-methoxyethyl sugar moiety.

"Linked deoxynucleoside" means a nucleic acid base (A, G, C, T, U) substituted by deoxyribose linked by a phosphate ester to form a nucleotide.

"Linked nucleosides" means adjacent nucleosides which are bonded together.

"Mismatch" or "non-complementary nucleobase" refers to the case when a nucleobase of a first nucleic acid is not capable of base pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising a modified internucleoside linkage, a modified sugar, or a modified nucleobase.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of base pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Nucleotide" means a nucleoside having a phosphate group covalently linked to the sugar portion of the nucleoside.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage (P=S) is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Pulmonary administration" means administration topical to the surface of the respiratory tract. Pulmonary administration includes nebulization, inhalation, or insufflation of powders or aerosols, by mouth and/or nose.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Segments" are defined as smaller or sub-portions of regions within a target nucleic acid.

"Sites," as used herein, are defined as unique nucleobase positions within a target nucleic acid. "Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Subject" means a human or non-human animal selected for treatment or therapy.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" or "treating" refers to administering a pharmaceutical composition to effect an alteration or improvement of a disease, disorder, or condition.

"Unmodified" nucleobases mean the purine bases adenine (A) and guanine (G), and the pyrimidine bases thymine (T), cytosine (C) and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Upstream" refers to the relative direction toward the 5' end or N-terminal end of a nucleic acid.

Certain Embodiments

Certain embodiments provide methods for decreasing A1AT mRNA and protein expression.

Certain embodiments provide methods for the treatment, amelioration, or prevention of diseases, disorders, and conditions associated with A1AT in an individual in need thereof. Also contemplated are methods for the preparation of a medicament for the treatment, amelioration, or prevention of a disease, disorder, or condition associated with A1AT. In certain embodiments, A1AT associated diseases, disorders, and conditions include liver disease, such as, A1ATD associated liver disease. In certain embodiments, A1AT associated diseases, disorders, and conditions include pulmonary diseases, such as, A1ATD associated pulmonary disease, COPD, or emphysema.

Such diseases, disorders, and conditions may have one or more risk factors, causes, or outcomes in common. Certain risk factors and causes for development of diseases, disorders, and conditions associated with A1ATD include genetic predisposition to alpha-1 antitrypsin deficiency. In certain embodiments, a defect in an individual's genetic code for alpha-1 antitrypsin (A1AT) is responsible for diseases, disorders, and conditions associated with A1ATD, such as, liver diseases and pulmonary diseases. In certain embodiments, genetic mutations lead to expression of mutant A1AT. In certain embodiments, mutant A1AT forms aggregates which are retained in the liver, causing liver dysfunction or hepatic toxicity. Certain outcomes associated with liver disease, including A1ATD associated liver disease, include abdominal swelling or pain, bruising easily, dark urine, light colored stools, itching all over the body, vomiting blood, passing bloody or black stools, jaundice, lack of normal weight and height gain in children, liver cirrhosis, and death. In certain embodiments, mutant A1AT forms aggregates which are retained in the lung, causing pulmonary dysfunction or pulmonary disease. Certain outcomes associated with pulmonary disease, including A1ATD associated pulmonary disease, include chronic cough, fatigue, respiratory infections, shortness of breath (dyspnea), wheezing, pulmonary hypertension, heart disease, and death.

Certain embodiments provide for the use of an A1AT specific inhibitor for treating, ameliorating, preventing, slowing progression, or stopping progression of an A1AT associated disease. In certain embodiments, A1AT specific inhibitors are nucleic acids (including antisense compounds), peptides, antibodies, small molecules, and other agents capable of inhibiting the expression of A1AT mRNA and/or A1AT protein.

In certain embodiments, methods of treatment include administering an A1AT specific inhibitor to an individual in need thereof. In certain embodiments, A1AT specific inhibitors are antisense compounds. In certain embodiments, the antisense compound is a modified oligonucleotide targeting A1AT.

Certain embodiments provide a method of reducing A1AT in an animal comprising administering to the animal a modified oligonucleotide targeting an A1AT nucleic acid sequence as shown in SEQ ID NO: 1. In certain embodiments, the modified oligonucleotide targeting A1AT consists of 12 to 30 linked nucleosides and is at least 90% complementary to the A1AT nucleic acid.

Certain embodiments provide a method of treating, ameliorating and/or preventing an A1ATD associated liver disease in an animal at risk for the A1ATD associated liver disease comprising: (a) identifying the animal at risk for developing the A1ATD associated liver disease; and (b) administering to the at risk animal a therapeutically effective amount of a modified oligonucleotide consisting of 12 to 30 linked nucleosides, wherein the modified oligonucleotide is at least 90% complementary to an A1AT nucleic acid.

Certain embodiments provide a method of treating, ameliorating and/or preventing an A1ATD associated pulmonary disease in an animal at risk for the A1ATD associated pulmonary disease comprising: (a) identifying the animal at risk for developing the A1ATD associated pulmonary disease; and (b) administering to the at risk animal a therapeutically effective amount of a modified oligonucleotide consisting of 12 to 30 linked nucleosides, wherein the modified oligonucleotide is at least 90% complementary to an A1AT nucleic acid.

Certain embodiments provide a method of halting progression of an A1ATD associated liver disease comprising: (a) identifying an animal with the A1ATD associated liver disease; and (b) administering to the animal a therapeutically effective amount of a modified oligonucleotide consisting of 12 to 30 linked nucleosides, wherein the modified oligonucleotide is at least 90% complementary to an A1AT nucleic acid.

Certain embodiments provide a method of lowering the risk for developing an A1ATD associated liver disease comprising: (a) identifying an animal at risk for developing A1ATD associated liver disease; and (b) administering to the at risk animal a therapeutically effective amount of a modified oligonucleotide consisting of 12 to 30 linked nucleosides, wherein the modified oligonucleotide is at least 90% complementary to an A1AT nucleic acid.

Certain embodiments provide a method of reducing fibrosis in an animal comprising: (a) identifying the animal at risk for developing fibrosis; and (b) administering to the at risk animal a therapeutically effective amount of a modified oligonucleotide consisting of 12 to 30 linked nucleosides, wherein the modified oligonucleotide is at least 90% complementary to an A1AT nucleic acid.

Certain embodiments provide a method of preventing organ damage, decreasing organ damage and/or improving organ function in an animal comprising: (a) identifying the animal at risk for organ damage or decrease organ function; and (b) administering to the at risk animal a therapeutically effective amount of a modified oligonucleotide consisting of 12 to 30 linked nucleosides, wherein the modified oligonucleotide is at least 90% complementary to an A1AT nucleic acid.

In certain embodiments, accumulation of A1AT aggregates is forestalled, prevented or delayed in an animal by the methods provided herein. In certain embodiments, the accumulation of A1AT aggregates is in a lung, liver or other organ or tissue.

In certain embodiments, the methods provided herein decreases TIMP1, collagen type 1, collagen type IV, collagen type III, MMP13, SMA, ALT and/or AST expression.

Embodiments described herein provide the use of an A1AT specific inhibitor, as described herein, for use in treating, ameliorating, preventing, slowing progression, or stopping progression of a liver disease, such as A1ATD associated liver disease, as described herein, by combination therapy with an additional agent or therapy, as described herein. Agents or therapies can be co-administered or administered concomitantly. In certain embodiments, A1AT specific inhibitors are antisense compounds.

Embodiments described herein provide the use of an A1AT specific inhibitor, as described herein, for use in treating, ameliorating, preventing, slowing progression, or stopping progression of a pulmonary disease, such as A1ATD associated pulmonary disease, as described herein, by combination therapy with an additional agent or therapy, as described herein. Agents or therapies can be co-administered or administered concomitantly. In certain embodiments, A1AT specific inhibitors are antisense compounds.

In certain embodiments, A1AT specific inhibitors are peptides or proteins (Chang, Y. P. et al., Am. J. Respir. Cell Mol. Biol. 2006. 35: 540-548) or ribozymes (Zern, M. A. et al., Gene Ther. 1999. 6: 114-120), and FLEAIG peptide (US 20110280863). In certain embodiments, A1AT specific inhibitors are antibodies (Miranda, E. et al., Hepatology. 2010. 52: 1078-1088; Piotrowska, U. et al., Thyroid. 2002. 12: 563-570).

In certain embodiments, A1AT specific inhibitors are small molecules, such as, but not limited to, rapamycin (Kaushal, S. et al., Exp. Biol. Med. 2010. 235: 700-709), 4-phenylbutyric acid, which prevents misfolding of A1AT (Burrows, J. A. et al., Proc. Natl. Acad. Sci. U.S.A. 2000. 97: 1796-1801), nafamostat mesilate (Sundaram, S. et al., Thromb. Haemost. 1996. 75: 76-82), trimethylamine N-oxide (US 20110280863), 1-deoxynojirimycin (Tan, A. et al., J. Biol. Chem. 1991. 266: 14504-14510), and D-galactosamine (Gross, V. et al., Biochim. Biophys. Acta. 1990. 1036: 143-150).

In certain embodiments, provided herein are compounds comprising a modified oligonucleotide consisting of 12 to 30 linked nucleosides and comprising a nucleobase sequence comprising a portion of at least 8, at least 10, at least 12, at least 14, at least 15, at least 16, at least 17, at least 18, at least 19, or at least 20 contiguous nucleobases complementary to an equal length portion of nucleobases 1575 to 1594 of SEQ ID NO: 1, wherein the nucleobase sequence of the modified oligonucleotide is at least 90% complementary to SEQ ID NO: 1.

In certain embodiments, provided herein are compounds comprising a modified oligonucleotide consisting of 12 to 30 linked nucleosides and comprising a nucleobase sequence comprising a portion of at least 8, at least 10, at least 12, at least 14, at least 15, at least 16, at least 17, at least 18, at least 19, or at least 20 contiguous nucleobases complementary to an equal length portion of nucleobases 1564 to 1583 of SEQ ID NO: 1, wherein the nucleobase sequence of the modified oligonucleotide is at least 90% complementary to SEQ ID NO: 1.

In certain embodiments, provided herein are compounds comprising a modified oligonucleotide consisting of 12 to 30 linked nucleosides and comprising a nucleobase sequence comprising a portion of at least 8, at least 10, at least 12, at least 14, at least 15, at least 16, at least 17, at least 18, at least 19, or at least 20 contiguous nucleobases complementary to an equal length portion of nucleobases 1561 to 1597 of SEQ ID NO: 1, wherein the nucleobase sequence of the modified oligonucleotide is at least 90% complementary to SEQ ID NO: 1.

In certain embodiments, provided herein are compounds comprising a modified oligonucleotide consisting of 12 to 30 linked nucleosides and comprising a nucleobase sequence comprising a portion of at least 8, at least 10, at least 12, at least 14, at least 15, at least 16, at least 17, at least 18, at least 19, or at least 20 contiguous nucleobases complementary to an equal length portion of nucleobases 1349 to 1597 of SEQ ID NO: 1, wherein the nucleobase sequence of the modified oligonucleotide is at least 90% complementary to SEQ ID NO: 1.

In certain embodiments, provided herein are compounds comprising a modified oligonucleotide consisting of 12 to 30 linked nucleosides and comprising a nucleobase sequence comprising a portion of at least 8, at least 10, at least 12, at least 14, at least 15, at least 16, at least 17, at least 18, at least 19, or at least 20 contiguous nucleobases complementary to an equal length portion of nucleobases 459 to 513 of SEQ ID NO: 1, wherein the nucleobase sequence of the modified oligonucleotide is at least 90% complementary to SEQ ID NO: 1.

In certain embodiments, provided herein are compounds comprising a modified oligonucleotide consisting of 12 to 30 linked nucleosides and having a nucleobase sequence comprising at least 8, at least 10, at least 12, at least 14, at least 16, at least 17, at least 18, at least 19, or 20 contiguous nucleobases of the nucleobase sequence of SEQ ID NO: 38.

In certain embodiments, provided herein are compounds comprising a modified oligonucleotide consisting of 12 to 30 linked nucleosides and having a nucleobase sequence comprising at least 8, at least 10, at least 12, at least 14, at least 16, at least 17, at least 18, at least 19, or 20 contiguous nucleobases of the nucleobase sequence of SEQ ID NO: 29.

In certain embodiments, provided herein are compounds comprising a modified oligonucleotide consisting of 12 to 30 linked nucleosides and having a nucleobase sequence comprising at least 8, at least 10, at least 12, at least 14, at least 16, at least 17, at least 18, at least 19, or 20 contiguous nucleobases of the nucleobase sequences of SEQ ID NO: 20-41.

In certain embodiments, the modified oligonucleotide consists of 15 to 30, 18 to 24, 19 to 22, or 20 linked nucleosides.

In certain embodiments, the nucleobase sequence of the modified oligonucleotide is at least 91%, at least 92%, at least 93%, at least 94%, at least 95%, at least 96%, at least 97%, at least 98%, at least 99%, or 100% complementary to SEQ ID NO: 1.

In certain embodiments, the modified oligonucleotide consists of a single-stranded modified oligonucleotide.

In certain embodiments, at least one internucleoside linkage of the modified oligonucleotide is a modified internucleoside linkage. In certain embodiments, at least one modified oligonucleotide is a phosphorothioate internucleoside linkage. In certain embodiments, each internucleoside linkage is a phosphorothioate internucleoside linkage.

In certain embodiments, at least one nucleoside of the modified oligonucleotide comprises a modified nucleobase. In certain embodiments, the modified nucleobase is a 5-methylcytosine.

In certain embodiments, the modified oligonucleotide comprises at least one modified sugar. In certain embodiments, the modified sugar is a 2'-O-methoxyethyl.

In certain embodiments, the modified oligonucleotide comprises at least one 2'-O-methoxyethyl nucleoside.

In certain embodiments, the modified sugar is a bicyclic sugar. In certain embodiments, the bicyclic sugar comprises a 4'-CH(CH$_3$)—O-2' bridge.

In certain embodiments, the modified oligonucleotide comprises:
a gap segment consisting of linked deoxynucleosides;
a 5' wing segment consisting of linked nucleosides;
a 3' wing segment consisting of linked nucleosides;
wherein the gap segment is positioned between the 5' wing segment and the 3' wing segment and wherein each nucleoside of each wing segment comprises a modified sugar.

In certain embodiments, the modified oligonucleotide comprises:
a gap segment consisting often linked deoxynucleosides;
a 5' wing segment consisting of five linked nucleosides;
a 3' wing segment consisting of five linked nucleosides;
wherein the gap segment is positioned between the 5' wing segment and the 3' wing segment, wherein each nucleoside of each wing segment comprises a 2'-O-methoxyethyl sugar; wherein each internucleoside linkage is a phosphorothioate linkage; and wherein each cytosine is a 5'-methylcytosine.

In certain embodiments, the modified oligonucleotide consists of 15 to 24 linked nucleosides and comprises a nucleobase sequence comprising a portion of at least 15 contiguous nucleobases complementary to an equal length portion of nucleobases 1575 to 1594 of SEQ ID NO: 1, and wherein the nucleobase sequence of the modified oligonucleotide is 100% complementary to SEQ ID NO: 1.

In certain embodiments, the modified oligonucleotide consists of 15 to 24 linked nucleosides and comprises a nucleobase sequence comprising a portion of at least 15 contiguous nucleobases complementary to an equal length portion of nucleobases 1564 to 1583 of SEQ ID NO: 1, and wherein the nucleobase sequence of the modified oligonucleotide is 100% complementary to SEQ ID NO: 1.

In certain embodiments, the modified oligonucleotide consists of 15 to 24 linked nucleosides and comprises a nucleobase sequence comprising a portion of at least 15 contiguous nucleobases complementary to an equal length portion of nucleobases 1561 to 1597 of SEQ ID NO: 1, and wherein the nucleobase sequence of the modified oligonucleotide is 100% complementary to SEQ ID NO: 1.

In certain embodiments, the modified oligonucleotide consists of 15 to 24 linked nucleosides and comprises a nucleobase sequence comprising a portion of at least 15 contiguous nucleobases complementary to an equal length portion of nucleobases 1349 to 1597 of SEQ ID NO: 1, and wherein the nucleobase sequence of the modified oligonucleotide is 100% complementary to SEQ ID NO: 1.

In certain embodiments, the modified oligonucleotide consists of 15 to 24 linked nucleosides and comprises a nucleobase sequence comprising a portion of at least 15 contiguous nucleobases complementary to an equal length portion of nucleobases 459 to 513 of SEQ ID NO: 1, and wherein the nucleobase sequence of the modified oligonucleotide is 100% complementary to SEQ ID NO: 1.

In certain embodiments, the modified oligonucleotide consists of 18 to 24 linked nucleosides and comprises a nucleobase sequence comprising a portion of at least 18 contiguous nucleobases complementary to an equal length portion of nucleobases 1575 to 1594 of SEQ ID NO: 1, and wherein the nucleobase sequence of the modified oligonucleotide is 100% complementary to SEQ ID NO: 1.

In certain embodiments, the modified oligonucleotide consists of 18 to 24 linked nucleosides and comprises a nucleobase sequence comprising a portion of at least 18 contiguous nucleobases complementary to an equal length portion of nucleobases 1564 to 1583 of SEQ ID NO: 1, and wherein the nucleobase sequence of the modified oligonucleotide is 100% complementary to SEQ ID NO: 1.

In certain embodiments, the modified oligonucleotide consists of 18 to 24 linked nucleosides and comprises a nucleobase sequence comprising a portion of at least 18 contiguous nucleobases complementary to an equal length portion of nucleobases 1561 to 1597 of SEQ ID NO: 1, and wherein the nucleobase sequence of the modified oligonucleotide is 100% complementary to SEQ ID NO: 1.

In certain embodiments, the modified oligonucleotide consists of 18 to 24 linked nucleosides and comprises a nucleobase sequence comprising a portion of at least 18 contiguous nucleobases complementary to an equal length portion of nucleobases 1349 to 1597 of SEQ ID NO: 1, and wherein the nucleobase sequence of the modified oligonucleotide is 100% complementary to SEQ ID NO: 1.

In certain embodiments, the modified oligonucleotide consists of 18 to 24 linked nucleosides and comprises a nucleobase sequence comprising a portion of at least 18 contiguous nucleobases complementary to an equal length portion of nucleobases 459 to 513 of SEQ ID NO: 1, and wherein the nucleobase sequence of the modified oligonucleotide is 100% complementary to SEQ ID NO: 1.

In certain embodiments, provided herein are compositions comprising a compound as described herein or a salt thereof and a pharmaceutically acceptable carrier or diluent.

In certain embodiments, provided herein are compositions as described herein for use in therapy.

In certain embodiments, provided herein are compositions as described herein for use in treating, ameliorating, or preventing an A1AT deficiency (A1ATD).

In certain embodiments, provided herein are compositions as described herein for use in treating an individual with a genetic predisposition to an A1ATD.

In certain embodiments, the compounds and compositions described herein are for use in treating, ameliorating, or preventing A1ATD associated liver disease.

In certain embodiments, the compounds and compositions described herein are for preventing or delaying A1AT aggregation in the liver.

In certain embodiments, the compounds and compositions described herein are for use in treating, ameliorating, or preventing A1ATD associated liver dysfunction.

In certain embodiments, the compounds and compositions described herein are for use in treating, ameliorating, or preventing A1ATD associated hepatic toxicity.

In certain embodiments, the compounds and compositions described herein are for use in treating, ameliorating, or preventing A1ATD associated pulmonary disease, COPD, and/or emphysema.

In certain embodiments, the compounds and compositions described herein are for preventing or delaying A1AT aggregation in the lungs.

In certain embodiments, the compounds and compositions described herein are for use in treating, ameliorating, or preventing A1ATD associated pulmonary dysfunction.

In certain embodiments, the compounds and compositions described herein are for use in treating, ameliorating, or preventing A1ATD associated pulmonary toxicity.

In certain embodiments, provided herein are methods comprising, identifying an animal at risk for developing A1ATD associated liver disease; and administering to the at risk animal a therapeutically effective amount of a modified oligonucleotide consisting of 12 to 30 linked nucleosides, wherein the modified oligonucleotide is at least 90% complementary to an A1AT nucleic acid.

In certain embodiments, provided herein are methods comprising, identifying an animal at risk for developing A1ATD associated pulmonary disease; and administering to the at risk animal a therapeutically effective amount of a modified oligonucleotide consisting of 12 to 30 linked nucleosides, wherein the modified oligonucleotide is at least 90% complementary to an A1AT nucleic acid.

Certain embodiments describe a method of slowing or halting progression of A1ATD associated liver disease by administering a compound or composition described herein. In certain embodiments, provided is a method comprising administering a modified oligonucleotide consisting of 12 to 30 linked nucleosides, wherein the modified oligonucleotide is at least 90% complementary to an A1AT nucleic acid, and wherein the progression of the A1ATD associated liver disease is slowed or halted. In certain embodiments, provided is a method comprising identifying an animal having an A1ATD-associated liver disease and administering to the animal a therapeutically effective amount of a modified oligonucleotide consisting of 12 to 30 linked nucleosides, wherein the modified oligonucleotide is at least 90% complementary to an A1AT nucleic acid, and wherein the progression of the A1ATD associated liver disease is slowed or halted. In certain embodiments, the nucleobase sequence of the modified oligonucleotide is at least 91%, at least 92%, at least 93%, at least 94%, at least 95%, at least 96%, at least 97%, at least 98%, at least 99%, or 100% complementary to an A1AT nucleic acid.

Certain embodiments describe a method of preventing or stopping or delaying or forestalling the accumulation or onset of accumulation of A1AT globules in the liver. In certain embodiments, the risk of A1ATD-associated liver disease is lowered or reduced. In certain embodiments, the development or onset of A1ATD-associated liver disease is prevented, delayed or forestalled. In certain embodiments, provided is a method comprising administering a modified oligonucleotide consisting of 12 to 30 linked nucleosides, wherein the modified oligonucleotide is at least 90% complementary to an A1AT nucleic acid, and wherein accumulation of A1AT globules in the liver is stopped, delayed or forestalled. In certain embodiments, provided is a method comprising administering a modified oligonucleotide consisting of 12 to 30 linked nucleosides, wherein the modified oligonucleotide is at least 90% complementary to an A1AT nucleic acid, and wherein the development or onset of A1ATD-associated liver disease is prevented, delayed or forestalled. In certain embodiments, provided is a method comprising identifying an animal at risk for developing A1ATD-associated liver disease and administering to the at risk animal a therapeutically effective amount of a modified oligonucleotide consisting of 12 to 30 linked nucleosides, wherein the modified oligonucleotide is at least 90% complementary to an A1AT nucleic acid, and wherein the risk of A1ATD associated liver disease is lowered or reduced. In certain embodiments, provided is a method comprising identifying an animal at risk for developing A1ATD-associated liver disease and administering to the at risk animal a therapeutically effective amount of a modified oligonucleotide consisting of 12 to 30 linked nucleosides, wherein the modified oligonucleotide is at least 90% complementary to an A1AT nucleic acid, and wherein accumulation of A1AT globules or aggregates in the liver is stopped, delayed or forestalled thereby reducing or lowering the risk of A1ATD associated liver disease. In certain embodiments, the nucleobase sequence of the modified oligonucleotide is at least 91%, at least 92%, at least 93%, at least 94%, at least 95%, at least 96%, at least 97%, at least 98%, at least 99%, or 100% complementary to an A1AT nucleic acid.

In certain embodiments, the modified oligonucleotide consists of 12 to 30 linked nucleosides and has a nucleobase sequence comprising at least 12, at least 14, at least 16, at least 17, at least 18, at least 19, or at least 20 contiguous nucleobases of the nucleobase sequences of SEQ ID NO: 20-41.

In certain embodiments, expression of A1AT mRNA is reduced.

In certain embodiments, expression of A1AT protein is reduced.

In certain embodiments, A1ATD associated liver disease is treated, ameliorated, or prevented.

In certain embodiments, A1AT aggregation in the liver is prevented or delayed.

In certain embodiments, A1ATD associated pulmonary disease is treated, ameliorated, or prevented.

In certain embodiments, A1AT aggregation in the lung is prevented or delayed.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that it is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to an A1AT nucleic acid is 12 to 30 subunits in length. In other words, such antisense compounds are from 12 to 30 linked subunits. In other embodiments, the antisense compound is 8 to 80, 12 to 50, 15 to 30, 18 to 24, 19 to 22, or 20 linked subunits. In certain such embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleosides.

In certain embodiments antisense oligonucleotides targeted to an A1AT nucleic acid may be shortened or truncated. For example, a single subunit may be deleted from the 5' end (5' truncation), or alternatively from the 3' end (3' truncation). A shortened or truncated antisense compound targeted to a A1AT nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Certain Antisense Compound Motifs and Mechanisms

In certain embodiments, antisense compounds have chemically modified subunits arranged in patterns, or motifs, to confer to the antisense compounds properties such as enhanced inhibitory activity, increased binding affinity for a target nucleic acid, or resistance to degradation by in vivo nucleases. Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may confer another desired property e.g., serve as a substrate for the cellular endonuclease RNase H, which cleaves the RNA strand of an RNA:DNA duplex.

Antisense activity may result from any mechanism involving the hybridization of the antisense compound (e.g., oligonucleotide) with a target nucleic acid, wherein the hybridization ultimately results in a biological effect. In certain embodiments, the amount and/or activity of the target nucleic acid is modulated. In certain embodiments, the amount and/or activity of the target nucleic acid is reduced. In certain embodiments, hybridization of the antisense compound to the target nucleic acid ultimately results in target nucleic acid degradation. In certain embodiments, hybridization of the antisense compound to the target nucleic acid does not result in target nucleic acid degradation. In certain such embodiments, the presence of the antisense compound hybridized with the target nucleic acid (occupancy) results in a modulation of antisense activity. In certain embodiments, antisense compounds having a particular chemical motif or pattern of chemical modifications are particularly suited to exploit one or more mechanisms. In certain embodiments, antisense compounds function through more than one mechanism and/or through mechanisms that have not been elucidated. Accordingly, the antisense compounds described herein are not limited by particular mechanism.

Antisense mechanisms include, without limitation, RNase H mediated antisense; RNAi mechanisms, which utilize the $R_1SC$ pathway and include, without limitation, siRNA, ssRNA and microRNA mechanisms; and occupancy based mechanisms. Certain antisense compounds may act through more than one such mechanism and/or through additional mechanisms.

RNase H-Mediated Antisense

In certain embodiments, antisense activity results at least in part from degradation of target RNA by RNase H. RNase H is a cellular endonuclease that cleaves the RNA strand of an RNA:DNA duplex. It is known in the art that single-stranded antisense compounds which are "DNA-like" elicit RNase H activity in mammalian cells. Accordingly, antisense compounds comprising at least a portion of DNA or DNA-like nucleosides may activate RNase H, resulting in cleavage of the target nucleic acid. In certain embodiments, antisense compounds that utilize RNase H comprise one or more modified nucleosides. In certain embodiments, such antisense compounds comprise at least one block of 1-8 modified nucleosides. In certain such embodiments, the modified nucleosides do not support RNase H activity. In certain embodiments, such antisense compounds are gapmers, as described herein. In certain such embodiments, the gap of the gapmer comprises DNA nucleosides. In certain such embodiments, the gap of the gapmer comprises DNA-like nucleosides. In certain such embodiments, the gap of the gapmer comprises DNA nucleosides and DNA-like nucleosides.

Certain antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—CH$_3$, among others), and bicyclic sugar modified nucleosides (such bicyclic sugar modified nucleosides may include those having a constrained ethyl). In certain embodiments, nucleosides in the wings may include several modified sugar moieties, including, for example 2'-MOE and bicyclic sugar moieties such as constrained ethyl or LNA. In certain embodiments, wings may include several modified and unmodified sugar moieties. In certain embodiments, wings may include various combinations of 2'-MOE nucleosides, bicyclic sugar moieties such as constrained ethyl nucleosides or LNA nucleosides, and 2'-deoxynucleosides.

Each distinct region may comprise uniform sugar moieties, variant, or alternating sugar moieties. The wing-gap-wing motif is frequently described as "X-Y-Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same; in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, the antisense compound has a gapmer motif in which the gap consists of 6, 7, 8, 9, 10, 11, 12, 13, 14, 15, or 16 linked nucleosides.

In certain embodiments, the antisense oligonucleotide has a sugar motif described by Formula A as follows:
$(J)_m$-$(B)_n$-$(J)_p$-$(B)_r$-$(A)_t$-$(D)_g$-$(A)_v$-$(B)_w$-$(J)_x$-$(B)_y$-$(J)_z$ wherein:
each A is independently a 2'-substituted nucleoside;
each B is independently a bicyclic nucleoside;
each J is independently either a 2'-substituted nucleoside or a 2'-deoxynucleoside;
each D is a 2'-deoxynucleoside;
m is 0-4; n is 0-2; p is 0-2; r is 0-2; t is 0-2; v is 0-2; w is 0-4; x is 0-2; y is 0-2; z is 0-4; g is 6-14; provided that:
at least one of m, n, and r is other than 0;
at least one of w and y is other than 0;
the sum of m, n, p, r, and t is from 2 to 5; and
the sum of v, w, x, y, and z is from 2 to 5.

RNAi Compounds

In certain embodiments, antisense compounds are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). In certain embodiments, antisense compounds comprise modifications that make them particularly suited for such mechanisms.

i. ssRNA Compounds

In certain embodiments, antisense compounds including those particularly suited for use as single-stranded RNAi compounds (ssRNA) comprise a modified 5'-terminal end. In certain such embodiments, the 5'-terminal end comprises a modified phosphate moiety. In certain embodiments, such modified phosphate is stabilized (e.g., resistant to degradation/cleavage compared to unmodified 5'-phosphate). In certain embodiments, such 5'-terminal nucleosides stabilize the 5'-phosphorous moiety. Certain modified 5'-terminal nucleosides may be found in the art, for example in WO/2011/139702.

In certain embodiments, the 5'-nucleoside of an ssRNA compound has Formula IIc:

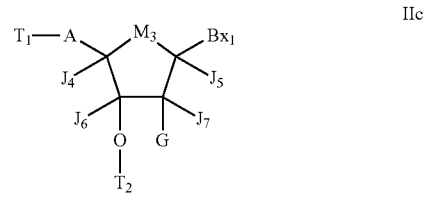

wherein:
T$_1$ is an optionally protected phosphorus moiety;
T$_2$ is an internucleoside linking group linking the compound of Formula IIc to the oligomeric compound;
A has one of the formulas:

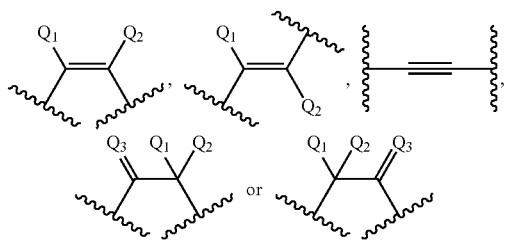

Q$_1$ and Q$_2$ are each, independently, H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl, substituted C$_2$-C$_6$ alkynyl or N(R$_3$)(R$_4$);
Q$_3$ is O, S, N(R$_5$) or C(R$_6$)(R$_7$);
each R$_3$, R$_4$, R$_5$, R$_6$ and R$_7$ is, independently, H, C$_1$-C$_6$ alkyl, substituted C$_1$-C$_6$ alkyl or C$_1$-C$_6$ alkoxy;
M$_3$ is O, S, NR$_{14}$, C(R$_{15}$)(R$_{16}$), C(R$_{15}$)(R$_{16}$)C(R$_{17}$)(R$_{18}$), C(R$_{15}$)=C(R$_{17}$), OC(R$_{15}$)(R$_{16}$) or OC(R$_{15}$)(Bx$_2$);
R$_{14}$ is H, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;
R$_{15}$, R$_{16}$, R$_{17}$ and R$_{18}$ are each, independently, H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;
Bx$_1$ is a heterocyclic base moiety;
or if Bx$_2$ is present then Bx$_2$ is a heterocyclic base moiety and Bx$_1$ is H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;

$J_4$, $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

or $J_4$ forms a bridge with one of $J_5$ or $J_7$ wherein said bridge comprises from 1 to 3 linked biradical groups selected from O, S, $NR_{19}$, $C(R_{20})(R_{21})$, $C(R_{20})=C(R_{21})$, $C[=C(R_{20})(R_{21})]$ and $C(=O)$ and the other two of $J_5$, $J_6$ and $J_7$ are each, independently, H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

each $R_{19}$, $R_{20}$ and $R_{21}$ is, independently, H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;

G is H, OH, halogen or $O-[C(R_8)(R_9)]_n-[(C=O)_m-X_1]_j-Z$;

each $R_8$ and $R_9$ is, independently, H, halogen, $C_1$-$C_6$ alkyl or substituted $C_1$-$C_6$ alkyl;

$X_1$ is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=X_2)J_1$, $OC(=X_2)N(J_1)(J_2)$ and $C(=X_2)N(J_1)(J_2)$;

$X_2$ is O, S or $NJ_3$;

each $J_1$, $J_2$ and $J_3$ is, independently, H or $C_1$-$C_6$ alkyl;

when j is 1 then Z is other than halogen or $N(E_2)(E_3)$; and wherein said oligomeric compound comprises from 8 to 40 monomeric subunits and is hybridizable to at least a portion of a target nucleic acid.

In certain embodiments, $M_3$ is O, CH=CH, $OCH_2$ or $OC(H)(Bx_2)$. In certain embodiments, $M_3$ is O.

In certain embodiments, $J_4$, $J_5$, $J_6$ and $J_7$ are each H. In certain embodiments, $J_4$ forms a bridge with one of $J_5$ or $J_7$.

In certain embodiments, A has one of the formulas:

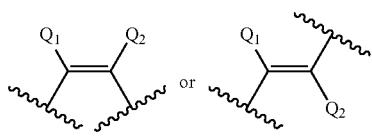

wherein:

$Q_1$ and $Q_2$ are each, independently, H, halogen, $C_1$-$C_6$ alkyl, substituted $C_1$-$C_6$ alkyl, $C_1$-$C_6$ alkoxy or substituted $C_1$-$C_6$ alkoxy. In certain embodiments, $Q_1$ and $Q_2$ are each H. In certain embodiments, $Q_1$ and $Q_2$ are each, independently, H or halogen. In certain embodiments, $Q_1$ and $Q_2$ is H and the other of $Q_1$ and $Q_2$ is F, $CH_3$ or $OCH_3$.

In certain embodiments, $T_1$ has the formula:

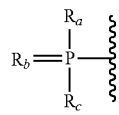

wherein:

$R_a$ and $R_c$ are each, independently, protected hydroxyl, protected thiol, $C_1$-$C_6$ alkyl, substituted $C_1$-$C_6$ alkyl, $C_1$-$C_6$ alkoxy, substituted $C_1$-$C_6$ alkoxy, protected amino or substituted amino; and $R_b$ is O or S. In certain embodiments, $R_b$ is O and $R_a$ and $R_c$ are each, independently, $OCH_3$, $OCH_2CH_3$ or $CH(CH_3)_2$.

In certain embodiments, G is halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2-CH=CH_2$, $O(CH_2)_2-OCH_3$, $O(CH_2)_2-SCH_3$, $O(CH_2)_2-OCF_3$, $O(CH_2)_3-N(R_{10})(R_{11})$, $O(CH_2)_2-ON(R_{10})(R_{11})$, $O(CH_2)_2-O(CH_2)_2-N(R_{10})(R_{11})$, $OCH_2C(=O)-N(R_{10})(R_{11})$, $OCH_2C(=O)-N(R_{12})-(CH_2)_2-N(R_{10})(R_{11})$ or $O(CH_2)_2-N(R_{12})-C(=NR_{13})[N(R_{10})(R_{11})]$ wherein $R_{10}$, $R_{11}$, $R_{12}$ and $R_{13}$ are each, independently, H or $C_1$-$C_6$ alkyl. In certain embodiments, G is halogen, $OCH_3$, $OCF_3$, $OCH_2CH_3$, $OCH_2CF_3$, $OCH_2-CH=CH_2$, $O(CH_2)_2-OCH_3$, $O(CH_2)_2-O(CH_2)_2-N(CH_3)_2$, $OCH_2C(=O)-N(H)CH_3$, $OCH_2C(=O)-N(H)-(CH_2)_2-N(CH_3)_2$ or $OCH_2-N(H)-C(=NH)NH_2$. In certain embodiments, G is F, $OCH_3$ or $O(CH_2)_2-OCH_3$. In certain embodiments, G is $O(CH_2)_2-OCH_3$.

In certain embodiments, the 5'-terminal nucleoside has Formula IIe:

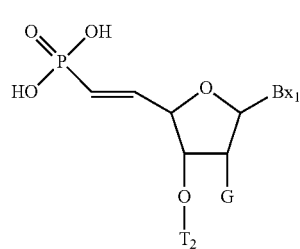

In certain embodiments, antisense compounds, including those particularly suitable for ssRNA comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides comprise one or more regions of alternating sugar modifications, wherein the nucleosides alternate between nucleotides having a sugar modification of a first type and nucleotides having a sugar modification of a second type. In certain embodiments, nucleosides of both types are RNA-like nucleosides. In certain embodiments the alternating nucleosides are selected from: 2'-OMe, 2'-F, 2'-MOE, LNA, and cEt. In certain embodiments, the alternating modifications are 2'-F and 2'-OMe. Such regions may be contiguous or may be interrupted by differently modified nucleosides or conjugated nucleosides.

In certain embodiments, the alternating region of alternating modifications each consist of a single nucleoside (i.e., the pattern is $(AB)_xA_y$ wherein A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides may include one or more regions of any of the following nucleoside motifs:

AABBAA;

ABBABB;

AABAAB;

ABBABAABB;

ABABAA;

AABABAB;

ABABAA;

ABBAABBABABAA;

BABBAABBABABAA;
or

ABABBAABBABABAA;

wherein A is a nucleoside of a first type and B is a nucleoside of a second type. In certain embodiments, A and B are each selected from 2'-F, 2'-OMe, BNA, and MOE.

In certain embodiments, oligonucleotides having such an alternating motif also comprise a modified 5' terminal nucleoside, such as those of formula IIc or IIe.

In certain embodiments, oligonucleotides comprise a region having a 2-2-3 motif. Such regions comprises the following motif:

-$(A)_2$-$(B)_x$-$(A)_2$-$(C)_y$-$(A)_3$- wherein: A is a first type of modified nucleoside;

B and C, are nucleosides that are differently modified than A, however, B and C may have the same or different modifications as one another;

x and y are from 1 to 15.

In certain embodiments, A is a 2'-OMe modified nucleoside. In certain embodiments, B and C are both 2'-F modified nucleosides. In certain embodiments, A is a 2'-OMe modified nucleoside and B and C are both 2'-F modified nucleosides.

In certain embodiments, oligonucleosides have the following sugar motif:

5'-(Q)-$(AB)_xA_y$-$(D)_z$ wherein:

Q is a nucleoside comprising a stabilized phosphate moiety. In certain embodiments, Q is a nucleoside having Formula IIc or IIe;

A is a first type of modifed nucleoside;

B is a second type of modified nucleoside;

D is a modified nucleoside comprising a modification different from the nucleoside adjacent to it. Thus, if y is 0, then D must be differently modified than B and if y is 1, then D must be differently modified than A. In certain embodiments, D differs from both A and B.

X is 5-15;

Y is 0 or 1;

Z is 0-4.

In certain embodiments, oligonucleosides have the following sugar motif:

5'-(Q)-$(A)_x$-$(D)_z$ wherein:

Q is a nucleoside comprising a stabilized phosphate moiety. In certain embodiments, Q is a nucleoside having Formula IIc or IIe;

A is a first type of modified nucleoside;

D is a modified nucleoside comprising a modification different from A.

X is 11-30;

Z is 0-4.

In certain embodiments A, B, C, and D in the above motifs are selected from: 2'-OMe, 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine.

In certain embodiments, antisense compounds, including those particularly suited for use as ssRNA comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region | 3'-region |
|---|---|---|
| PS | Alternating PO/PS | 6 PS |
| PS | Alternating PO/PS | 7 PS |
| PS | Alternating PO/PS | 8 PS | ii. siRNA Compounds

In certain embodiments, antisense compounds are double-stranded RNAi compounds (siRNA). In such embodiments, one or both strands may comprise any modification motif described above for ssRNA. In certain embodiments, ssRNA compounds may be unmodified RNA. In certain embodiments, siRNA compounds may comprise unmodified RNA nucleosides, but modified internucleoside linkages.

Several embodiments relate to double-stranded compositions wherein each strand comprises a motif defined by the location of one or more modified or unmodified nucleosides. In certain embodiments, compositions are provided comprising a first and a second oligomeric compound that are fully or at least partially hybridized to form a duplex region and further comprising a region that is complementary to and hybridizes to a nucleic acid target. It is suitable that such a composition comprise a first oligomeric compound that is an antisense strand having full or partial complementarity to a nucleic acid target and a second oligomeric compound that is a sense strand having one or more regions of complementarity to and forming at least one duplex region with the first oligomeric compound.

The compositions of several embodiments modulate gene expression by hybridizing to a nucleic acid target resulting in loss of its normal function. In certain embodiment, the degradation of the targeted nucleic acid is facilitated by an activated RISC complex that is formed with compositions of the invention.

Several embodiments are directed to double-stranded compositions wherein one of the strands is useful in, for example, influencing the preferential loading of the opposite strand into the RISC (or cleavage) complex. The compositions are useful for targeting selected nucleic acid molecules and modulating the expression of one or more genes. In some embodiments, the compositions of the present invention hybridize to a portion of a target RNA resulting in loss of normal function of the target RNA.

Certain embodiments are drawn to double-stranded compositions wherein both the strands comprises a hemimer motif, a fully modified motif, a positionally modified motif or an alternating motif. Each strand of the compositions of the present invention can be modified to fulfil a particular role in for example the siRNA pathway. Using a different motif in each strand or the same motif with different chemical modifications in each strand permits targeting the antisense strand for the RISC complex while inhibiting the incorporation of the sense strand. Within this model, each strand can be independently modified such that it is enhanced for its particular role. The antisense strand can be modified at the 5'-end to enhance its role in one region of the RISC while the 3'-end can be modified differentially to enhance its role in a different region of the RISC.

The double-stranded oligonucleotide molecules can be a double-stranded polynucleotide molecule comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof. The double-stranded oligonucleotide molecules can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double-stranded structure, for example wherein the double-stranded region is about 15 to about 30, e.g., about 15, 16, 17, 18, 19, 20, 21, 22, 23, 24, 25, 26, 27, 28, 29 or 30 base pairs; the antisense strand comprises nucleotide sequence that is complementary to nucleotide sequence in a target nucleic acid molecule or a portion thereof and the sense strand comprises nucleotide sequence corresponding to the target nucleic acid sequence or a portion thereof (e.g., about 15 to about 25 or more nucleotides of the double-stranded oligonucleotide molecule are complementary to the target nucleic acid or a portion thereof). Alternatively, the double-stranded oligonucleotide is assembled from a single oligonucleotide, where the self-complementary sense and antisense regions of the siRNA are linked by means of a nucleic acid based or non-nucleic acid-based linker(s).

The double-stranded oligonucleotide can be a polynucleotide with a duplex, asymmetric duplex, hairpin or asymmetric hairpin secondary structure, having self-complementary sense and antisense regions, wherein the antisense region comprises nucleotide sequence that is complementary to nucleotide sequence in a separate target nucleic acid molecule or a portion thereof and the sense region having nucleotide sequence corresponding to the target nucleic acid sequence or a portion thereof. The double-stranded oligonucleotide can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNAi.

In certain embodiments, the double-stranded oligonucleotide comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, van der waals interactions, hydrophobic interactions, and/or stacking interactions. In certain embodiments, the double-stranded oligonucleotide comprises nucleotide sequence that is complementary to nucleotide sequence of a target gene. In another embodiment, the double-stranded oligonucleotide interacts with nucleotide sequence of a target gene in a manner that causes inhibition of expression of the target gene.

As used herein, double-stranded oligonucleotides need not be limited to those molecules containing only RNA, but further encompasses chemically modified nucleotides and non-nucleotides. In certain embodiments, the short interfering nucleic acid molecules lack 2'-hydroxy (2'-OH) containing nucleotides. In certain embodiments short interfering nucleic acids optionally do not include any ribonucleotides (e.g., nucleotides having a 2'-OH group). Such double-stranded oligonucleotides that do not require the presence of ribonucleotides within the molecule to support RNAi can however have an attached linker or linkers or other attached or associated groups, moieties, or chains containing one or more nucleotides with 2'-OH groups. Optionally, double-stranded oligonucleotides can comprise ribonucleotides at about 5, 10, 20, 30, 40, or 50% of the nucleotide positions. As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics. For example, double-stranded oligonucleotides can be used to epigenetically silence genes at both the post-transcriptional level and the pre-transcriptional level. In a non-limiting example, epigenetic regulation of gene expression by siRNA molecules of the invention can result from siRNA mediated modification of chromatin structure or methylation pattern to alter gene expression (see, for example, Verdel et al., 2004, Science, 303, 672-676; Pal-Bhadra et al., 2004, Science, 303, 669-672; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237).

It is contemplated that compounds and compositions of several embodiments provided herein can target by a dsRNA-mediated gene silencing or RNAi mechanism, including, e.g., "hairpin" or stem-loop double-stranded RNA effector molecules in which a single RNA strand with self-complementary sequences is capable of assuming a double-stranded conformation, or duplex dsRNA effector molecules comprising two separate strands of RNA. In various embodiments, the dsRNA consists entirely of ribonucleotides or consists of a mixture of ribonucleotides and deoxynucleotides, such as the RNA/DNA hybrids disclosed, for example, by WO 00/63364, filed Apr. 19, 2000, or U.S. Ser. No. 60/130,377, filed Apr. 21, 1999. The dsRNA or dsRNA effector molecule may be a single molecule with a region of self-complementarity such that nucleotides in one segment of the molecule base pair with nucleotides in another segment of the molecule. In various embodiments, a dsRNA that consists of a single molecule consists entirely of ribonucleotides or includes a region of ribonucleotides that is complementary to a region of deoxyribonucleotides. Alternatively, the dsRNA may include two different strands that have a region of complementarity to each other.

In various embodiments, both strands consist entirely of ribonucleotides, one strand consists entirely of ribonucleotides and one strand consists entirely of deoxyribonucleotides, or one or both strands contain a mixture of ribonucleotides and deoxyribonucleotides. In certain embodiments, the regions of complementarity are at least 70, 80, 90, 95, 98, or 100% complementary to each other and to a target nucleic acid sequence. In certain embodiments, the region of the dsRNA that is present in a double-stranded conformation includes at least 19, 20, 21, 22, 23, 24, 25, 26, 27, 28, 29, 30, 50, 75, 100, 200, 500, 1000, 2000 or 5000 nucleotides or includes all of the nucleotides in a cDNA or other target nucleic acid sequence being represented in the dsRNA. In some embodiments, the dsRNA does not contain any single stranded regions, such as single stranded ends, or the dsRNA is a hairpin. In other embodiments, the dsRNA has one or more single stranded regions or overhangs. In certain embodiments, RNA/DNA hybrids include a DNA strand or region that is an antisense strand or region (e.g, has at least 70, 80, 90, 95, 98, or 100% complementarity to a target nucleic acid) and an RNA strand or region that is a sense strand or region (e.g, has at least 70, 80, 90, 95, 98, or 100% identity to a target nucleic acid), and vice versa.

In various embodiments, the RNA/DNA hybrid is made in vitro using enzymatic or chemical synthetic methods such as those described herein or those described in WO 00/63364, filed Apr. 19, 2000, or U.S. Ser. No. 60/130,377, filed Apr. 21, 1999. In other embodiments, a DNA strand synthesized in vitro is complexed with an RNA strand made in vivo or in vitro before, after, or concurrent with the transformation of the DNA strand into the cell. In yet other embodiments, the dsRNA is a single circular nucleic acid containing a sense and an antisense region, or the dsRNA includes a circular nucleic acid and either a second circular nucleic acid or a linear nucleic acid (see, for example, WO 00/63364, filed Apr. 19, 2000, or U.S. Ser. No. 60/130,377, filed Apr. 21, 1999.) Exemplary circular nucleic acids include lariat structures in which the free 5' phosphoryl group of a nucleotide becomes linked to the 2' hydroxyl group of another nucleotide in a loop back fashion.

In other embodiments, the dsRNA includes one or more modified nucleotides in which the 2' position in the sugar contains a halogen (such as fluorine group) or contains an alkoxy group (such as a methoxy group) which increases the half-life of the dsRNA in vitro or in vivo compared to the corresponding dsRNA in which the corresponding 2' position contains a hydrogen or an hydroxyl group. In yet other embodiments, the dsRNA includes one or more linkages between adjacent nucleotides other than a naturally-occurring phosphodiester linkage. Examples of such linkages include phosphoramide, phosphorothioate, and phosphorodithioate linkages. The dsRNAs may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000, or U.S. Ser. No. 60/130,377, filed Apr. 21, 1999.

In other embodiments, the dsRNA can be any of the at least partially dsRNA molecules disclosed in WO 00/63364, as well as any of the dsRNA molecules described in U.S. Provisional Application 60/399,998; and U.S. Provisional Application 60/419,532, and PCT/US2003/033466, the teaching of which is hereby incorporated by reference. Any of the dsRNAs may be expressed in vitro or in vivo using the methods described herein or standard methods, such as those described in WO 00/63364.

Occupancy

In certain embodiments, antisense compounds are not expected to result in cleavage or the target nucleic acid via RNase H or to result in cleavage or sequestration through the $R_1SC$ pathway. In certain such embodiments, antisense activity may result from occupancy, wherein the presence of the hybridized antisense compound disrupts the activity of the target nucleic acid. In certain such embodiments, the antisense compound may be uniformly modified or may comprise a mix of modifications and/or modified and unmodified nucleosides.

Target Nucleic Acids, Target Regions and Nucleotide Sequences

Nucleotide sequences that encode A1AT include, without limitation, the following: GENBANK Accession No. NM_000295.4 (incorporated herein as SEQ ID NO: 1), the complement of GENBANK Accession No. NT_026437.12 truncated from nucleosides 75840001 to 75860000 (incorporated herein as SEQ ID NO: 2), a variant sequence at the site of the PiZ mutation (incorporated herein as SEQ ID NO: 3), GENBANK Accession No. NM_001002235.2 (incorporated herein as SEQ ID NO: 4), GENBANK Accession No. NM_001002236.2 (incorporated herein as SEQ ID NO: 5), GENBANK Accession No. NM_001127700.1 (incorporated herein at SEQ ID NO: 6), GENBANK Accession No. NM_001127701.1 (incorporated herein as SEQ ID NO: 7), GENBANK Accession No. NM_001127702.1 (incorporated herein as SEQ ID NO: 8), GENBANK Accession No. NM_001127703.1 (incorporated herein as SEQ ID NO: 9), GENBANK Accession No. NM_001127704.1 (incorporated herein as SEQ ID NO: 10), GENBANK Accession No. NM_001127705.1 (incorporated herein as SEQ ID NO: 11), GENBANK Accession No. NM_001127706.1 (incorporated herein as SEQ ID NO: 12), GENBANK Accession No. NM_001127707.1 (incorporated herein as SEQ ID NO: 13), and GENBANK Accession No. NW_001121215.1 truncated from nucleotides 7483001 to U.S. Pat. No. 7,503,000 (incorporated herein as SEQ ID NO: 14).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for A1AT can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, 10, 9, 8, 7, 6, 5, 4, 3, 2, or 1 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifcally exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in A1AT mRNA levels are indicative of inhibition of A1AT expression. Reductions in levels of an A1AT protein are also indicative of inhibition of target mRNA expression. Further, phenotypic changes are indicative of inhibition of A1AT expression. For example, reduced or prevented A1AT protein aggregates can be indicative of inhibition of A1AT expression. In another example, prevented liver dysfunction can be indicative of inhibition of A1AT expression. In another example, restored liver function can be indicative of inhibition of A1AT expression. In another example, prevented or reduced hepatic toxicity can be indicative of A1AT expression. In another example, prevented pulmonary dysfunction can be indicative of inhibition of A1AT expression. In another example, restored pulmonary function can be indicative of inhibition of A1AT expression. In another example, prevented or reduced pulmonary toxicity can be indicative of A1AT expression.

Hybridization

In some embodiments, hybridization occurs between an antisense compound disclosed herein and an A1AT nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with an A1AT nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as an A1AT nucleic acid).

Non-complementary nucleobases between an antisense compound and an A1AT nucleic acid may be tolerated provided that the antisense compound remains able to specifically hybridize to a target nucleic acid. Moreover, an antisense compound may hybridize over one or more segments of an A1AT nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to an A1AT nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to an A1AT nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as an A1AT nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as an A1AT nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. In certain embodiments, the antisense compounds are complementary to at least an 18 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occuring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to an A1AT nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified.

Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'-OCH$_2$CH$_3$, 2'-OCH$_2$CH$_2$F and 2'-O(CH$_2$)$_2$OCH$_3$ substituent groups. The substituent at the 2' position can also be selected from allyl, amino, azido, thio, O-allyl, O—$C_1$-$C_{10}$ alkyl, OCF$_3$, OCH$_2$F, O(CH$_2$)$_2$SCH$_3$, O(CH$_2$)$_2$—O—N(R$_m$)(R$_n$), O—CH$_2$—C(=O)—N(R$_m$)(R$_n$), and O—CH$_2$—C(=O)—N(R$_l$)—(CH$_2$)$_2$—N(R$_m$)(R$_n$), where each R$_l$, R$_m$ and R$_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' (also referred to as constrained ethyl or cEt) and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, $C_1$-$C_{12}$ alkyl, or a protecting group (see U.S. Pat. No. 7,427,672, issued on Sep. 23, 2008); 4'-CH$_2$—C(H)(CH$_3$)-2' (see Chattopadhyaya et al., *J. Org. Chem.*, 2009, 74, 118-134); and 4'-CH$_2$—C(=CH$_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr.*

Opinion Invest. Drugs, 2001, 2, 558-561; Braasch et al., Chem. Biol., 2001, 8, 1-7; and Orum et al., Curr. Opinion Mol. Ther., 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. No. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C($R_a$)($R_b$)]$_n$—, —C($R_a$)=C($R_b$)—, —C($R_a$)=N—, —C(=O)—, —C(=N$R_a$)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —[C($R_a$)($R_b$)]$_n$—, —[C($R_a$)($R_b$)]$_n$—O—, —C($R_aR_b$)—N(R)—O— or —C($R_aR_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the 3-D configuration. Previously, α-L-methyleneoxy (4'-CH$_2$—O-2') BNA's have been incorporated into antisense oligonucleotides that showed antisense activity (Frieden et al., Nucleic Acids Research, 2003, 21, 6365-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, (J) propylene carbocyclic (4'-(CH$_2$)$_3$-2') BNA and (K) vinyl BNA as depicted below:

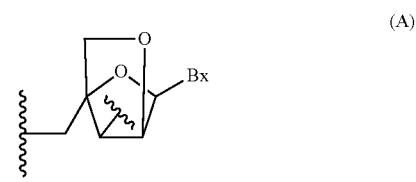

(A)

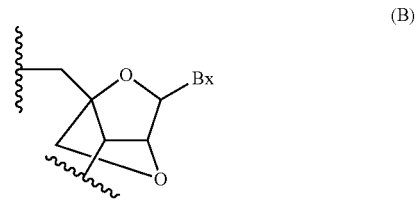

(B)

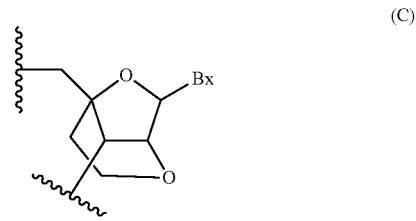

(C)

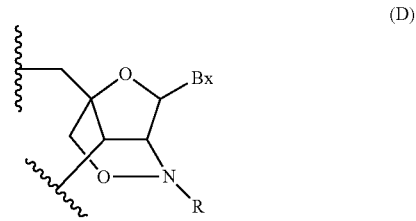

(D)

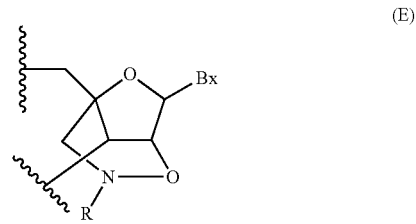

(E)

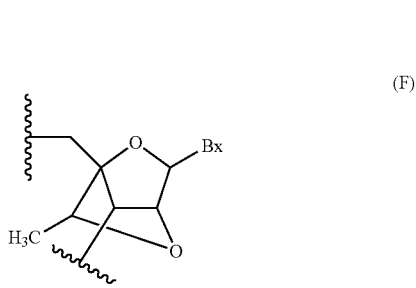

(F)

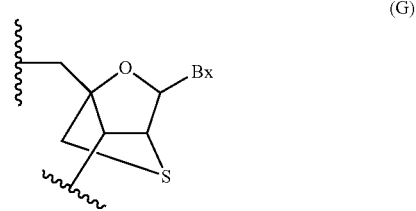

(G)

-continued

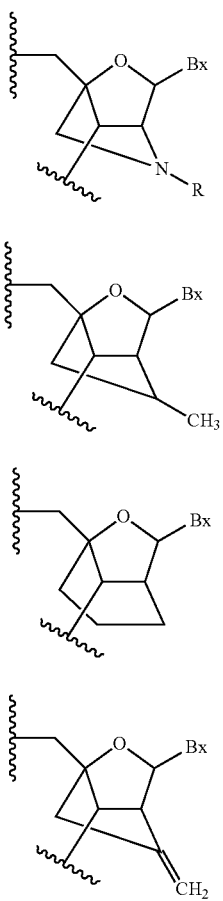

(H)

(I)

(J)

(K)

wherein Bx is the base moiety and R is independently H, a protecting group, $C_1$-$C_{12}$ alkyl or $C_1$-$C_{12}$ alkoxy.

In certain embodiments, bicyclic nucleosides are provided having Formula I:

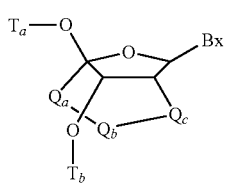

I wherein:

Bx is a heterocyclic base moiety;

-$Q_a$-$Q_b$-$Q_c$- is —$CH_2$—N(R)—$CH_2$—, —C(=O)—N($R_c$)—$CH_2$—, —$CH_2$—O—N($R_c$)—, —$CH_2$—N($R_c$)—O— or —N($R_c$)—O—$CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

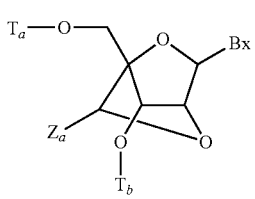

II wherein:

Bx is a heterocyclic base moiety;

$T_a$ and $T_b$ are each, independently, H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

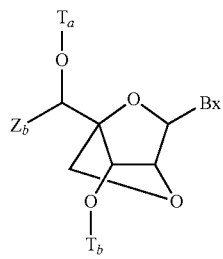

III wherein:

Bx is a heterocyclic base moiety;

$T_a$ and $T_b$ are each, independently, H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

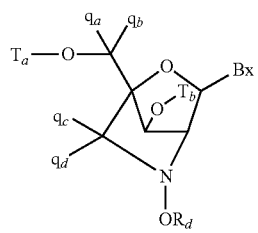

IV wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

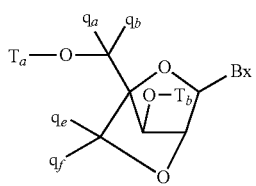

V wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C($=$O)$OJ_j$, C($=$O)$NJ_jJ_k$, C($=$O)$J_j$, O—C($=$O)$NJ_jJ_k$, N(H)C($=$NH)$NJ_jJ_k$, N(H)C($=$O)$NJ_jJ_k$ or N(H)C($=$S)$NJ_jJ_k$;

or $q_e$ and $q_f$ together are $=$C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

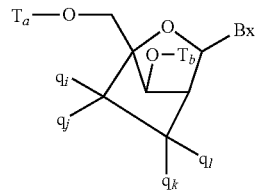

VI wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C($=$O)$OJ_j$, C($=$O)$NJ_jJ_k$, C($=$O)$J_j$, O—C($=$O)$NJ_jJ_k$, N(H)C($=$NH)$NJ_jJ_k$, N(H)C($=$O)$NJ_jJ_k$ or N(H)C($=$S)$NJ_jJ_k$; and $q_i$ and $q_j$ or $q_l$ and $q_k$ together are $=$C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-($CH_2$)$_3$-2' bridge and the alkenyl analog bridge 4'-CH$=$CH—$CH_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[($CH_2$)$_n$O]$_m$$CH_3$, O($CH_2$)$_n$$NH_2$, O($CH_2$)$_n$$CH_3$, O($CH_2$)$_n$F, O($CH_2$)$_n$$ONH_2$, $OCH_2$C($=$O)N(H)$CH_3$, and O($CH_2$)$_n$ON[($CH_2$)$_n$$CH_3$]$_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modifed nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.,* 2002, 10, 841-854) or fluoro HNA (F-HNA) having a tetrahydropyran ring system as illustrated below:

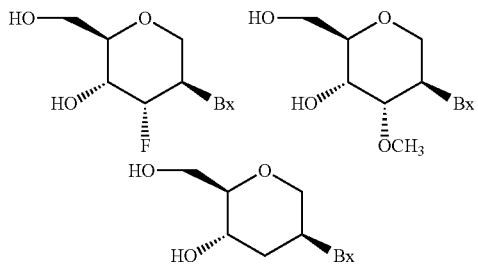

In certain embodiments, sugar surrogates are selected having Formula VII:

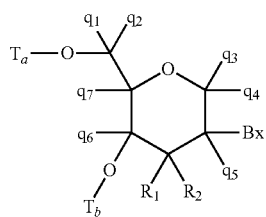

wherein independently for each of said at least one tetrahydropyran nucleoside analog of Formula VII:
Bx is a heterocyclic base moiety;
$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;
$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., *Biochemistry,* 2002, 41, 4503-4510; and U.S. Pat. Nos. 5,698,685; 5,166, 315; 5,185,444; and 5,034,506). As used here, the term "morpholino" means a sugar surrogate having the following formula:

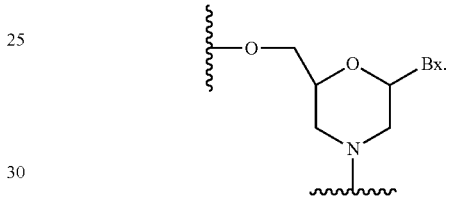

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.,* 2008, 130(6), 1979-1984; Horváth et al., *Tetrahedron Letters,* 2007, 48, 3621-3623; Nauwelaerts et al., *J. Am. Chem. Soc.,* 2007, 129(30), 9340-9348; Gu et al., *Nucleosides, Nucleotides & Nucleic Acids,* 2005, 24(5-7), 993-998; Nauwelaerts et al., *Nucleic Acids Research,* 2005, 33(8), 2452-2463; Robeyns et al., *Acta Crystallographica, Section F: Structural Biology and Crystallization Commu-* nications, 2005, F61(6), 585-586; Gu et al., *Tetrahedron*, 2004, 60(9), 2111-2123; Gu et al., *Oligonucleotides*, 2003, 13(6), 479-489; Wang et al., *J. Org. Chem.*, 2003, 68, 4499-4505; Verbeure et al., *Nucleic Acids Research*, 2001, 29(24), 4941-4947; Wang et al., *J. Org. Chem.*, 2001, 66, 8478-82; Wang et al., *Nucleosides, Nucleotides & Nucleic Acids*, 2001, 20(4-7), 785-788; Wang et al., *J Am. Chem.*, 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

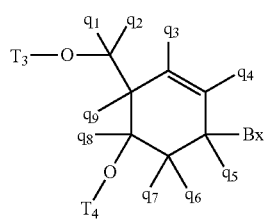

X wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—$N(R_m)(R_n)$, or O—$CH_2$—$C(=O)$—$N(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854). Such ring systems can undergo various additional substitutions to enhance activity.

Methods for the preparations of modified sugars are well known to those skilled in the art. Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH($CH_3$)—O-2') bridging group. In certain embodiments, the (4'-CH($CH_3$)—O-2') modified nucleosides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional modified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties can also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds comprise one or more modified nucleobases. In certain embodiments, shortened or gap-widened antisense oligonucleotides comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to an A1AT nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally or by inhalation. Accordingly, in one embodiment, employed in the methods described herein is a pharmaceutical composition comprising an antisense compound targeted to an A1AT nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

In certain embodiments, antisense compounds, including, but not limited to those particularly suited for use as ssRNA, are modified by attachment of one or more conjugate groups. In general, conjugate groups modify one or more properties of the attached oligonucleotide, including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligonucleotide. Conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylamino-carbonyl-oxycholesterol moiety (Crooke et al., J. Pharmacol. Exp. Ther., 1996, 277, 923-937). For additional conjugates including those useful for ssRNA and their placement within antisense compounds, see e.g., U.S. Application No. 61/583,963.

Cell Culture and Antisense Compounds Treatment

The effects of antisense compounds on the level, activity or expression of A1AT nucleic acids can be tested in vitro in a variety of cell types. Cell types used for such analyses are available from commerical vendors (e.g. American Type Culture Collection, Manassas, Va.; Zen-Bio, Inc., Research Triangle Park, N.C.; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HepG2 cells, Hep3B cells, and transgenic mouse primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides are mixed with LIPOFECTIN in OPTI-MEM 1 (Invitrogen, Carlsbad, Calif.) to achieve the desired final concentration of antisense oligonucleotide and a LIPOFECTIN concentration that typically ranges 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of an A1AT nucleic acid can be assayed in a variety of ways known in the art. For example, target nucleic acid levels can be quantitated by, e.g., Northern blot analysis, competitive polymerase chain reaction (PCR), or quantitaive real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to an A1AT nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of A1AT nucleic acids can be assessed by measuring A1AT protein levels. Protein levels of A1AT can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of mouse, rat, monkey, and human A1AT are commercially available.

In Vivo Testing of Antisense Compounds

Antisense compounds, for example, antisense oligonucleotides, are tested in animals to assess their ability to inhibit expression of A1AT and produce phenotypic changes, such as, reduced or prevented A1AT protein aggregation, prevented liver and/or pulmonary dysfunction, restored liver and/or pulmonary function, prevented or reduced hepatic and/or pulmonary toxicity. Such parameters may be indicative of A1AT expression. In certain embodiments, A1ATD associated liver dysfunction or hepatic toxicity is determined by measuring A1AT aggregates in liver tissue, measuring transaminases (including ALT and AST), measuring bilirubin, and serum albumin. In certain embodiments, A1ATD associated pulmonary dysfunction or pulmonary toxicity is determined by measuring ATAT aggregates in pulmonary tissue or by spirometry to measure $FEV_1$ and FVC. Testing may be performed in normal animals, or in experimental disease models. For administration to animals, antisense oligonucleotides are formulated in a pharmaceutically acceptable diluent, such as phosphate-buffered saline.

Administration includes parenteral routes of administration, such as intraperitoneal, intravenous, and subcutaneous. Administration also includes pulmonary routes of administration, such as nebulization, inhalation, and insufflation. Calculation of antisense oligonucleotide dosage and dosing frequency depends upon factors such as route of administration and animal body weight. Following a period of treatment with antisense oligonucleotides, RNA is isolated from liver tissue and/or pulmonary tissue and changes in A1AT nucleic acid expression are measured.

Certain Indications

In certain embodiments, provided herein are methods of treating an individual comprising administering one or more pharmaceutical compositions described herein. In certain embodiments, the individual has a liver disease, such as A1ATD associated liver disease. In certain embodiments, the individual is at risk for developing A1ATD associated liver disease. This includes individuals with a genetic predisposition to developing A1ATD. In certain embodiments, the individual has been identified as in need of therapy. Examples of such individuals include, but are not limited to those having a mutation in the genetic code for A1AT. In certain embodiments, provided herein are methods for prophylactically reducing A1AT expression in an individual. Certain embodiments include treating an individual in need thereof by administering to an individual a therapeutically effective amount of an antisense compound targeted to an A1AT nucleic acid.

In one embodiment, administration of a therapeutically effective amount of an antisense compound targeted to an A1AT nucleic acid is accompanied by monitoring of A1AT levels in the individual, to determine an individual's response to administration of the antisense compound. An individual's response to administration of the antisense compound is used by a physician to determine the amount and duration of therapeutic intervention.

In certain embodiments, administration of an antisense compound targeted to an A1AT nucleic acid results in reduction of A1AT expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to an A1AT nucleic acid results in a change in a measure of A1AT aggregates retained in the liver, liver function, and hepatic toxicity. In certain embodiments, administration of an A1AT antisense compound decreases the measure by at least 15, 20, 25, 30, 35, 40, 45, 50, 55, 60, 65, 70, 75, 80, 85, 90, 95 or 99%, or a range defined by any two of these values. In some embodiments, administration of an A1AT antisense compound increases the measure by at least 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to A1AT are used for the preparation of a medicament for treating a patient suffering or susceptible to a liver disease, such as, A1ATD associated liver disease.

Certain Combination Therapies

In certain embodiments, one or more pharmaceutical compositions described herein are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions described herein. In certain embodiments, one or more pharmaceutical compositions described herein are co-administered with another pharmaceutical agent to treat an undesired effect of that other pharmaceutical agent. In certain embodiments, one or more pharmaceutical compositions described herein are co-administered with another pharmaceutical agent to produce a combinational effect. In certain embodiments, one or more pharmaceutical compositions described herein are co-administered with another pharmaceutical agent to produce a synergistic effect.

In certain embodiments, one or more pharmaceutical compositions described herein and one or more other pharmaceutical agents are administered at the same time. In certain embodiments, one or more pharmaceutical compositions described herein and one or more other pharmaceutical agents are administered at different times. In certain embodiments, one or more pharmaceutical compositions described herein and one or more other pharmaceutical agents are prepared together in a single formulation. In certain embodiments, one or more pharmaceutical compositions described herein and one or more other pharmaceutical agents are prepared separately.

In certain embodiments, pharmaceutical agents that may be co-administered with a pharmaceutical composition described herein include carbamazepine, A1AT replacement therapy, antiviral therapy, lipid lowering therapy, steroids and COPD therapies. In certain embodiments, antiviral therapy includes interferon alpha-2b, interferon alpha-2a, and interferon alphacon-1 (pegylated and unpegylated); ribavirin; penciclovir (Denavir); foscarnet (Foscavir); Ascoxal; Acyclovir; Valacyclovir; Famciclovir; a viral RNA replication inhibitor; a second antisense oligomer; a viral therapeutic vaccine; a viral prophylactic vaccine; lamivudine (3TC); entecavir (ETV); tenofovir diisoproxil fumarate (TDF); telbivudine (LdT); adefovir; or an anti-virus antibody therapy (monoclonal or polyclonal). In certain embodiments, lipid lowering therapy includes, but is not limited to, bile salt sequestering resins (e.g., cholestyramine, colestipol, and colesevelam hydrochloride), cholesterol biosynthesis inhibitors, especially HMG CoA reductase inhibitors (such as atorvastatin, pravastatin, simvastatin, lovastatin, fluvastatin, cerivastatin, rosuvastatin, and pitivastatin (itavastatin/risivastatin)), nicotinic acid, fibric acid derivatives (e.g., clofibrate, gemfibrozil, fenofibrate, bezafibrate, and ciprofibrate), probucol, neomycin, dextrothyroxine, plant-stanol esters, cholesterol absorption inhibitors (e.g., ezetimibe and pamaqueside), CETP inhibitors (e.g. torcetrapib, and JTT-705) MTP inhibitors (e.g., implitapide), squalene synthetase inhibitors, bile acid sequestrants such as cholestyramine, inhibitors of bile acid transporters (apical sodium-dependent bile acid transporters), regulators of hepatic CYP7a, ACAT inhibitors (e.g. Avasimibe), estrogen replacement therapeutics (e.g., tamoxigen), synthetic HDL (e.g. ETC-216), anti-inflammatories (e.g., glucocorticoids) and antisense compounds targeting cardiovascular targets (e.g., Apo B targeting compounds and ApoC-III targeting compounds). In certain embodiments, COPD therapies include, for example, anti-inflammation drugs; bronchodilators, such as ipratropium (Atrovent), tiotropium (Spiriva), salmeterol (Serevent), formoterol (Foradil), or albuterol; or oxygen therapy. Anti-inflammatory drugs can include steroids, NSAIDS (non-steroidal anti-inflammatory drugs), COX inhibitors, montelukast (Singulair), roflimulast, antihistamines and the like. In certain embodiments, the second agent can be an asthma drug such as an anti-inflammatory drug, a bronchodilator (e.g., beta-2 agonists (LABA2), theophylline, ipratropium), a leukotriene modifier, Cromolyn, nedocromil, a decongestant and immunotherapy. In certain embodiments, such co-administration is for the treatment of liver disease. In certain embodiments, such co-administration is for the treatment of pulmonary disease.

In certain embodiments, pharmaceutical agents that may be co-administered with an A1AT specific inhibitor as described herein include, but are not limited to, an additional A1AT inhibitor. In certain embodiments, the co-adminstered pharmaceutical agent is administered prior to administration of a pharmaceutical composition described herein. In certain embodiments, the co-administered pharmaceutical agent is administered following administration of a pharmaceutical composition described herein. In certain embodiments the co-administered pharmaceutical agent is administered at the same time as a pharmaceutical composition described herein. In certain embodiments the dose of a co-administered pharmaceutical agent is the same as the dose that would be administered if the co-administered pharmaceutical agent was administered alone. In certain embodiments the dose of a co-administered pharmaceutical agent is lower than the dose that would be administered if the co-administered pharmaceutical agent was administered alone. In certain embodiments the dose of a co-administered pharmaceutical agent is greater than the dose that would be administered if the co-administered pharmaceutical agent was administered alone.

In certain embodiments, the co-administration of a second compound enhances the effect of a first compound, such that co-administration of the compounds results in an effect that is greater than the effect of administering the first compound alone. In other embodiments, the co-administration results in an effect that is additive of the effects of the compounds when administered alone. In certain embodiments, the co-administration results an effect that is supra-additive of the effect of the compounds when administered alone. In certain embodiments, the first compound is an antisense compound. In certain embodiments, the second compound is an antisense compound.

Certain Compounds

Approximately 700 modified antisense oligonucleotides were tested for their effect on human A1AT mRNA in vitro in several cell types. Of the approximately 700 modified antisense oligonucleotides, twenty-three compounds were selected for further in vitro studies based on in vitro activity to test their potency in dose response studies in PiZ transgenic mice primary hepatocytes, HepG2 cells, Hep3B cells. Of the twenty-three compound, fifteen compounds were tested in CD1 mice and Sprague-Dawley rats for tolerability, and in PiZ transgenic mice for efficacy and tolerability. A final selection of seven compounds was made for further study in cynomolgous monkeys based on systemic tolerability and activity in the rodent studies. These seven compounds were selected because they are highly tolerable and very active in transgenic PiZ mice. The compounds are complementary to the regions 1421-1440, 1561-1580, 1564-1583, 1565-1584, 1571-1590, 1575-1594, and 1577-1596 of SEQ ID NO: 1. In certain embodiments, the compounds targeting the listed regions comprise a modified oligonucleotide having some nucleobase portion of the sequence recited in SEQ ID NOs: 23, 26, 29, 30, 34, 38, and 40. In certain embodiments, the compounds targeting the listed regions or having a nucleobase portion of a sequence recited in the listed SEQ ID NOs can be various lengths and may have one of various motifs. In certain embodiments, a compound targeting a region or having a nucleobase portion of a sequence recited in the listed SEQ ID NOs has the specific length and motif as indicated by the ISIS NOs: 487660, 487662, 496386, 496392, 496393, 496404, and 496407. Compounds described above as being highly tolerable and active in transgenic PiZ mice were tested in cynomologous monkeys to assess tolerability in a primate.

In certain embodiments, the compounds as described herein are efficacious by virtue of having at least one of an in vitro $IC_{50}$ of less than 10 µM, less than 9 µM, less than 8 µM, less than 7 µM, less than 6 µM, less than 5 µM, less than 4 µM, less than 3 µM, less than 2 µM, less than 1 µM when delivered to a human cell line as described herein. In certain embodiments, the compounds as described herein are highly tolerable as demonstrated by having at least one of an increase an ALT or AST value of no more than 4 fold, 3 fold, or 2 fold over saline treated animals or an increase in liver, spleen or kidney weight of no more than 30%, 20%, 15%, 12%, 10%, 5% or 2%.

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Human Alpha-1 Antitrypsin in HepG2 Cells

Antisense oligonucleotides were designed targeting a human alpha-1 antitrypsin (A1AT) nucleic acid and were tested for their effects on A1AT mRNA in vitro. Cultured human HepG2 cells at a density of 20,000 cells per well were transfected using electroporation with 4,500 nM antisense oligonucleotide. After a treatment period of approximately 24 hours, RNA was isolated from the cells and A1AT mRNA levels were measured by quantitative real-time PCR using human primer probe set RTS3320 (forward sequence GGAGATGCTGCCCAGAAGAC, designated herein as SEQ ID NO: 45; reverse sequence GCTGGCGGTATAG-GCTGAAG, designated herein as SEQ ID NO: 46; probe sequence ATCAGGATCACCCAACCT-TCAACAAGATCA, designated herein as SEQ ID NO: 47). A1AT mRNA levels were adjusted according to total RNA content, as measured by RIBOGREEN®. Results are presented as percent inhibition of A1AT, relative to untreated control cells. Of the 695 oligonucleotides tested, only those selected for further study are presented.

The modified antisense oligonucleotides in Table 1 were designed as 5-10-5 MOE gapmers. The gainers are 20 nucleosides in length, wherein the central gap segment comprises ten 2'-deoxynucleosides and is flanked on both sides (in the 5' and 3' directions) by wings comprising five nucleosides each. Each nucleoside in the 5' wing segment and each nucleoside in the 3' wing segment has a 2'MOE sugar modification. The internucleoside linkages throughout each gapmer are phosphorothioate (P=S) linkages. All cytosine residues throughout each gapmer are 5-methylcytosines. "Human Target start site" indicates the 5'-most nucleoside to which the gapmer is targeted in the human gene sequence. The gapmers of Table 1 are targeted to SEQ ID NO: 1 (GENBANK Accession No. NM_000295.4) and SEQ ID NO: 2 (the complement of GENBANK Accession No. NT_026437.12 truncated from nucleosides 75840001 to 75860000).

TABLE 1

Inhibition of human A1AT mRNA levels by modified antisense oligonucleotides targeted to SEQ ID NOs: 1 and 2

| Start Site on SEQ ID NO: 1 | Stop Site on SEQ ID NO: 1 | Start Site on SEQ ID NO: 2 | Stop Site on SEQ ID NO: 2 | Motif | Sequence | ISIS No | % inhibition | SEQ ID NO |
|---|---|---|---|---|---|---|---|---|
| 459 | 478 | 10624 | 10643 | 5-10-5 | TGGTGCTGTTGGACTGGTGT | 489009 | 36 | 20 |
| 464 | 483 | 10629 | 10648 | 5-10-5 | GATATTGGTGCTGTTGGACT | 489010 | 30 | 21 |
| 494 | 513 | 10659 | 10678 | 5-10-5 | GGCTGTAGCGATGCTCACTG | 489013 | 61 | 22 |
| 1421 | 1440 | 15118 | 15137 | 5-10-5 | GGGTTTGTTGAACTTGACCT | 496393 | 38 | 23 |
| 1479 | 1498 | 15176 | 15195 | 5-10-5 | CCACTTTTCCCATGAAGAGG | 496346 | 51 | 24 |
| 1493 | 1512 | 15190 | 15209 | 5-10-5 | TTGGGTGGGATTCACCACTT | 496360 | 42 | 25 |
| 1561 | 1580 | 15258 | 15277 | 5-10-5 | CTTTAATGTCATCCAGGGAG | 496404 | 90 | 26 |
| 1562 | 1581 | 15259 | 15278 | 5-10-5 | TCTTTAATGTCATCCAGGGA | 496405 | 86 | 27 |
| 1563 | 1582 | 15260 | 15279 | 5-10-5 | TTCTTTAATGTCATCCAGGG | 496406 | 89 | 28 |
| 1564 | 1583 | 15261 | 15280 | 5-10-5 | CTTCTTTAATGTCATCCAGG | 496407 | 94 | 29 |
| 1565 | 1584 | 15262 | 15281 | 5-10-5 | CCTTCTTTAATGTCATCCAG | 496386 | 95 | 30 |
| 1566 | 1585 | 15263 | 15282 | 5-10-5 | CCCTTCTTTAATGTCATCCA | 496387 | 97 | 31 |
| 1567 | 1586 | 15264 | 15283 | 5-10-5 | ACCCTTCTTTAATGTCATCC | 496388 | 95 | 32 |
| 1570 | 1589 | 15267 | 15286 | 5-10-5 | TCAACCCTTCTTTAATGTCA | 496391 | 83 | 33 |
| 1571 | 1590 | 15268 | 15287 | 5-10-5 | CTCAACCCTTCTTTAATGTC | 496392 | 74 | 34 |
| 1572 | 1591 | 15269 | 15288 | 5-10-5 | GCTCAACCCTTCTTTAATGT | 487657 | 79 | 35 |
| 1573 | 1592 | 15270 | 15289 | 5-10-5 | AGCTCAACCCTTCTTTAATG | 487658 | 77 | 36 |
| 1574 | 1593 | 15271 | 15290 | 5-10-5 | CAGCTCAACCCTTCTTTAAT | 487659 | 77 | 37 |
| 1575 | 1594 | 15272 | 15291 | 5-10-5 | CCAGCTCAACCCTTCTTTAA | 487660 | 87 | 38 |
| 1576 | 1595 | 15273 | 15292 | 5-10-5 | ACCAGCTCAACCCTTCTTTA | 487661 | 83 | 39 |
| 1577 | 1596 | 15274 | 15293 | 5-10-5 | GACCAGCTCAACCCTTCTTT | 487662 | 79 | 40 |
| 1578 | 1597 | 15275 | 15294 | 5-10-5 | GGACCAGCTCAACCCTTCTT | 474061 | 84 | 41 |

Example 2: Antisense Inhibition of Human Alpha-1 Antitrypsin in Transgenic Mouse Primary Hepatocytes Transgenic mouse primary hepatocytes are from PiZ mice, originally generated by Sifers et al (Nucl. Acids Res. 15: 1459-1457, 1987) by introducing a 14.4 kb DNA fragment containing the entire A1AT gene plus 2 kb of 5' and 3' flanking genomic DNA sequences into the germ line. Primary hepatocytes were isolated from the mice and cultured for in vitro screening.

Additional antisense oligonucleotides were designed targeting a human alpha-1 antitrypsin (A1AT) nucleic acid and were tested for their effects on A1AT mRNA in vitro. Antisense oligonucleotides from the study described in Example 1 were also included in the assay and are presented in Table 2. Cultured transgenic mouse primary hepatocytes at a density of 10,000 cells per well were transfected using Cytofectin reagent with 150 nM antisense oligonucleotide. After a treatment period of approximately 24 hours, RNA was isolated from the cells and A1AT mRNA levels were measured by quantitative real-time PCR using human primer probe set RTS3320. A1AT mRNA levels were adjusted according to total RNA content, as measured by RIBOGREEN®. Results are presented as percent inhibition of A1AT, relative to untreated control cells. Of the 311 oligonucleotides tested, only those only those selected for further study are presented.

The modified antisense oligonucleotides presented in Table 2 were designed as 5-10-5 MOE gapmers or 5-9-5 MOE gapmers. The 5-10-5 gapmer is 20 nucleosides in length, wherein the central gap segment comprises often 2'-deoxynucleosides and is flanked on both sides (in the 5' and 3' directions) by wings comprising five nucleosides each. The 5-9-5 gapmer is 19 nucleosides in length, wherein the central gap segment comprises nine 2'-deoxynucleosides and is flanked on both sides (in the 5' and 3' directions) by wings comprising five nucleosides each. Each nucleoside in the 5' wing segment and each nucleoside in the 3' wing segment has a 2'MOE sugar modification. The internucleoside linkages throughout the gapmer are phosphorothioate (P=S) linkages. All cytosine residues throughout the gapmer are 5-methylcytosines. "Human Target start site" indicates the 5'-most nucleoside to which the gapmer is targeted in the human gene sequence. The gapmers of Table 2 are targeted to SEQ ID NO: 2 or a variant sequence, designated herein as SEQ ID NO: 3.

TABLE 2

Inhibition of human A1AT mRNA levels by modified antisense oligonucleotides targeted to SEQ ID NO: 2

| Start Site on SEQ ID NO: 2 | Stop Site on SEQ ID NO: 2 | Start Site on SEQ ID NO: 3 | Stop Site on SEQ ID NO: 3 | ISIS No | Sequence | Motif | % inhibition | SEQ ID NO |
| --- | --- | --- | --- | --- | --- | --- | --- | --- |
| 15275 | 15294 | n/a | n/a | 474061 | GGACCAGCTCAACCCTTCTT | 5-10-5 | 96 | 41 |
| 15269 | 15288 | n/a | n/a | 487657 | GCTCAACCCTTCTTTAATGT | 5-10-5 | 96 | 35 |
| 15270 | 15289 | n/a | n/a | 487658 | AGCTCAACCCTTCTTTAATG | 5-10-5 | 95 | 36 |
| 15271 | 15290 | n/a | n/a | 487659 | CAGCTCAACCCTTCTTTAAT | 5-10-5 | 96 | 37 |
| 15272 | 15291 | n/a | n/a | 487660 | CCAGCTCAACCCTTCTTTAA | 5-10-5 | 95 | 38 |
| 15273 | 15292 | n/a | n/a | 487661 | ACCAGCTCAACCCTTCTTTA | 5-10-5 | 95 | 39 |
| 15274 | 15293 | n/a | n/a | 487662 | GACCAGCTCAACCCTTCTTT | 5-10-5 | 95 | 40 |
| 10624 | 10643 | n/a | n/a | 489009 | TGGTGCTGTTGGACTGGTGT | 5-10-5 | 93 | 20 |
| 10629 | 10648 | n/a | n/a | 489010 | GATATTGGTGCTGTTGGACT | 5-10-5 | 90 | 21 |
| 10659 | 10678 | n/a | n/a | 489013 | GGCTGTAGCGATGCTCACTG | 5-10-5 | 94 | 22 |
| 15176 | 15195 | n/a | n/a | 496346 | CCACTTTTCCCATGAAGAGG | 5-10-5 | 95 | 24 |
| 15190 | 15209 | n/a | n/a | 496360 | TTGGGTGGGATTCACCACTT | 5-10-5 | 96 | 25 |
| 15262 | 15281 | n/a | n/a | 496386 | CCTTCTTTAATGTCATCCAG | 5-10-5 | 97 | 30 |
| 15263 | 15282 | n/a | n/a | 496387 | CCCTTCTTTAATGTCATCCA | 5-10-5 | 97 | 31 |
| 15264 | 15283 | n/a | n/a | 496388 | ACCCTTCTTTAATGTCATCC | 5-10-5 | 97 | 32 |
| 15267 | 15286 | n/a | n/a | 496391 | TCAACCCTTCTTTAATGTCA | 5-10-5 | 96 | 33 |
| 15268 | 15287 | n/a | n/a | 496392 | CTCAACCCTTCTTTAATGTC | 5-10-5 | 96 | 34 |
| 15118 | 15137 | n/a | n/a | 496393 | GGGTTTGTTGAACTTGACCT | 5-10-5 | 96 | 23 |
| 15258 | 15277 | n/a | n/a | 496404 | CTTTAATGTCATCCAGGGAG | 5-10-5 | 99 | 26 |
| 15259 | 15278 | n/a | n/a | 496405 | TCTTTAATGTCATCCAGGGA | 5-10-5 | 97 | 27 |

TABLE 2-continued

Inhibition of human A1AT mRNA levels by modified antisense oligonucleotides targeted to SEQ ID NO: 2

| Start Site on SEQ ID NO: 2 | Stop Site on SEQ ID NO: 2 | Start Site on SEQ ID NO: 3 | Stop Site on SEQ ID NO: 3 | ISIS No | Sequence | Motif | % inhibition | SEQ ID NO |
|---|---|---|---|---|---|---|---|---|
| 15260 | 15279 | n/a | n/a | 496406 | TTCTTTAATGTCATCCAGGG | 5-10-5 | 98 | 28 |
| 15261 | 15280 | n/a | n/a | 496407 | CTTCTTTAATGTCATCCAGG | 5-10-5 | 98 | 29 |
| n/a | n/a | 19 | 37 | 489112 | GTCCCTTTCTTGTCGATGG | 5-9-5 | 56 | 42 |

Example 3: Dose-Dependent Antisense Inhibition of Human A1AT in Transgenic Mouse Primary Hepatocytes Transgenic mouse primary hepatocytes are from PiZ mice, originally generated by Sifers et al (Nucl. Acids Res. 15: 1459-1457, 1987) by introducing a 14.4 kb DNA fragment containing the entire A1AT gene plus 2 kb of 5' and 3' flanking genomic DNA sequences into the germ line. Primary hepatocytes were isolated from the mice and cultured for in vitro screening.

Gapmers from Examples 1 and 2 exhibiting in vitro inhibition of human A1AT were tested at various doses in transgenic mouse primary hepatocytes. Cells were plated at a density of 10,000 cells per well and transfected using Cytofectin reagent with 4.69 nM, 9.38 nM, 18.75 nM, 37.50 nM, 75.00 nM, and 150.00 nM concentrations of antisense oligonucleotide, as specified in Table 3. After a treatment period of approximately 16 hours, RNA was isolated from the cells and A1AT mRNA levels were measured by quantitative real-time PCR. Human A1AT primer probe set RTS3320 was used to measure mRNA levels. A1AT mRNA levels were adjusted according to total RNA content, as measured by RIBOGREEN®. Results are presented as percent inhibition of A1AT, relative to untreated control cells.

The half maximal inhibitory concentration (IC$_{50}$) of each oligonucleotide is also presented in Table 3. A1AT mRNA levels were reduced in a dose-dependent manner in some of the antisense oligonucleotide treated cells. 'n.d.' indicates that the IC$_{50}$ for that compound was not calculated.

TABLE 3

Dose-dependent antisense inhibition of human A1AT in transgenic mouse primary hepatocytes

| ISIS No | 4.69 nM | 9.38 nM | 18.75 nM | 37.5 nM | 75.0 nM | 150.0 nM | IC$_{50}$ (nM) |
|---|---|---|---|---|---|---|---|
| 474061 | 3 | 11 | 15 | 36 | 56 | 86 | 54 |
| 487657 | 24 | 55 | 75 | 93 | 98 | 98 | 9 |
| 487658 | 23 | 42 | 59 | 89 | 95 | 97 | 12 |
| 487659 | 30 | 22 | 56 | 81 | 94 | 96 | 15 |
| 487660 | 23 | 39 | 70 | 85 | 96 | 98 | 12 |
| 487661 | 19 | 39 | 57 | 85 | 95 | 97 | 14 |
| 487662 | 22 | 27 | 49 | 85 | 92 | 95 | 17 |
| 489009 | 7 | 18 | 46 | 79 | 97 | 99 | 21 |
| 489010 | 25 | 24 | 46 | 79 | 96 | 99 | 17 |
| 489013 | 26 | 53 | 77 | 87 | 99 | 100 | 9 |
| 489112 | 2 | 11 | 11 | 0 | 18 | 43 | n.d. |
| 496346 | 1 | 29 | 53 | 85 | 95 | 99 | 19 |
| 496360 | 25 | 37 | 51 | 82 | 96 | 99 | 14 |
| 496386 | 19 | 26 | 57 | 83 | 95 | 99 | 16 |
| 496387 | 24 | 48 | 78 | 92 | 98 | 99 | 9 |
| 496388 | 12 | 23 | 57 | 78 | 96 | 99 | 18 |
| 496391 | 0 | 9 | 54 | 69 | 94 | 98 | 24 |
| 496392 | 2 | 27 | 47 | 79 | 96 | 98 | 20 |
| 496393 | 34 | 24 | 60 | 83 | 96 | 99 | 13 |
| 496404 | 17 | 39 | 51 | 78 | 96 | 98 | 16 |
| 496405 | 15 | 18 | 35 | 72 | 94 | 99 | 22 |
| 496406 | 14 | 25 | 60 | 88 | 98 | 99 | 16 |
| 496407 | 26 | 39 | 62 | 88 | 97 | 99 | 12 |

Example 4: Dose-Dependent Antisense Inhibition of Human A1AT in HepG2 Cells

Gapmers from of the study described in Example 3 were also tested at various doses in HepG2 cells. Cells were plated at a density of 20,000 cells per well and transfected using electroporation with 0.31 µM, 0.63 µM, 1.25 µM, 2.50 µM, 5.00 µM, and 10.00 µM concentrations of antisense oligonucleotide, as specified in Table 4. After a treatment period of approximately 16 hours, RNA was isolated from the cells and A1AT mRNA levels were measured by quantitative real-time PCR. Human A1AT primer probe set RTS3320 was used to measure mRNA levels. A1AT mRNA levels were adjusted according to total RNA content, as measured by RIBOGREEN®. Results are presented as percent inhibition of A1AT, relative to untreated control cells.

The half maximal inhibitory concentration (IC$_{50}$) of each oligonucleotide is also presented in Table 4. A1AT mRNA levels were reduced in a dose-dependent manner in some of the antisense oligonucleotide treated cells. 'n.d.' indicates that the IC$_{50}$ for that compound was not calculated.

TABLE 4

Dose-dependent antisense inhibition of human A1AT in HepG2 cells

| ISIS No | 0.31 µM | 0.63 µM | 1.25 µM | 2.50 µM | 5.00 µM | 10.00 µM | IC$_{50}$ (µM) |
|---|---|---|---|---|---|---|---|
| 474061 | 25 | 21 | 18 | 12 | 22 | 39 | n.d. |
| 487657 | 37 | 25 | 58 | 71 | 82 | 90 | 1 |
| 487658 | 13 | 29 | 55 | 66 | 77 | 87 | 1.4 |
| 487659 | 12 | 27 | 38 | 60 | 79 | 84 | 1.8 |
| 487660 | 55 | 77 | 85 | 91 | 92 | 89 | <0.3 |
| 487661 | 47 | 63 | 69 | 85 | 88 | 86 | <0.3 |

TABLE 4-continued

Dose-dependent antisense inhibition of human A1AT in HepG2 cells

| ISIS No | 0.31 μM | 0.63 μM | 1.25 μM | 2.50 μM | 5.00 μM | 10.00 μM | IC$_{50}$ (μM) |
|---|---|---|---|---|---|---|---|
| 487662 | 36 | 55 | 76 | 81 | 85 | 86 | 0.4 |
| 489009 | 0 | 9 | 14 | 31 | 51 | 64 | 5.4 |
| 489010 | 19 | 21 | 23 | 37 | 46 | 50 | 9.8 |
| 489013 | 16 | 8 | 50 | 55 | 73 | 82 | 2 |
| 489112 | 26 | 0 | 15 | 14 | 12 | 23 | n.d. |
| 496346 | 0 | 20 | 39 | 49 | 38 | 48 | 6.8 |
| 496360 | 10 | 12 | 19 | 54 | 60 | 66 | 3.5 |
| 496386 | 50 | 66 | 88 | 96 | 97 | 98 | <0.3 |
| 496387 | 52 | 72 | 90 | 96 | 98 | 99 | <0.3 |
| 496388 | 56 | 67 | 86 | 93 | 97 | 98 | <0.3 |
| 496391 | 17 | 29 | 56 | 77 | 87 | 95 | 1.2 |
| 496392 | 10 | 32 | 58 | 77 | 91 | 94 | 1.2 |
| 496393 | 34 | 22 | 22 | 43 | 50 | 61 | 5.7 |
| 496404 | 22 | 60 | 82 | 90 | 95 | 97 | 0.5 |
| 496405 | 33 | 37 | 67 | 80 | 92 | 96 | 0.7 |
| 496406 | 40 | 57 | 80 | 90 | 95 | 98 | 0.4 |
| 496407 | 51 | 50 | 77 | 88 | 94 | 98 | 0.3 |

Example 5: Dose-Dependent Antisense Inhibition of Human A1AT in Hep3B Cells

Gapmers selected from of the studies described in Examples 3 and 4 were also tested at various doses in Hep3B cells. Cells were plated at a density of 20,000 cells per well and transfected using electroporation with 0.31 μM, 0.63 μM, 1.25 μM, 2.50 μM, 5.00 μM, and 10.00 μM concentrations of antisense oligonucleotide, as specified in Table 5. After a treatment period of approximately 16 hours, RNA was isolated from the cells and A1AT mRNA levels were measured by quantitative real-time PCR. Human A1AT primer probe set RTS3320 was used to measure mRNA levels. A1AT mRNA levels were adjusted according to total RNA content, as measured by RIBOGREEN®. Results are presented as percent inhibition of A1AT, relative to untreated control cells.

The half maximal inhibitory concentration (IC$_{50}$) of each oligonucleotide is also presented in Table 5. A1AT mRNA levels were reduced in a dose-dependent manner in some of the antisense oligonucleotide treated cells. 'n.d.' indicates that the IC$_{50}$ for that compound was not calculated.

TABLE 5

Dose-dependent antisense inhibition of human A1AT in Hep3B cells

| ISIS NO | 0.31 μM | 0.63 μM | 1.25 μM | 2.50 μM | 5.00 μM | 10.00 μM | IC$_{50}$ (μM) |
|---|---|---|---|---|---|---|---|
| 474061 | 0 | 12 | 52 | 69 | 89 | 93 | 2.0 |
| 487657 | 15 | 30 | 45 | 53 | 72 | 88 | 2.0 |
| 489009 | 9 | 9 | 10 | 8 | 32 | 56 | n.d. |
| 489010 | 0 | 0 | 11 | 9 | 36 | 40 | n.d. |
| 489013 | 50 | 25 | 39 | 51 | 55 | 65 | n.d. |
| 489112 | 0 | 0 | 0 | 0 | 2 | 8 | n.d. |
| 496346 | 0 | 16 | 31 | 23 | 45 | 49 | n.d. |
| 496360 | 0 | 15 | 10 | 32 | 38 | 56 | 9.0 |
| 496387 | 29 | 63 | 79 | 92 | 98 | 99 | 0.4 |
| 496393 | 0 | 2 | 11 | 15 | 42 | 55 | 8.0 |
| 496406 | 9 | 20 | 63 | 72 | 90 | 96 | 1.0 |
| 496407 | 18 | 16 | 71 | 82 | 95 | 98 | 1.0 |

Example 6: Tolerability of Antisense Oligonucleotides Targeting Human A1AT in CD1 Mice CD1® mice (Charles River, Mass.) are a multipurpose model of mice frequently utilized for testing safety and efficacy. The mice were treated with ISIS antisense oligonucleotides selected from the studies described above, and evaluated for changes in the levels of various markers.

Treatment

Six to seven-week old male CD1 mice were maintained at a 12-hour light/dark cycle and fed Purina mouse chow 5001 ad libitum. The mice were acclimated for at least 7 days in the research facility before initiation of the experiment. Groups of four CD1 mice each were injected subcutaneously twice a week for 6 weeks with 50 mg/kg of ISIS 474061, ISIS 487657, ISIS 487658, ISIS 487659, ISIS 487660, ISIS 487661, ISIS 487662, ISIS 487663, ISIS 487664, and ISIS 489013. A group of four CD1 mice were injected subcutaneously twice a week for 6 weeks with PBS and served as the control group. Three days after the last dose at each time point, mice were euthanized and organs and plasma were harvested for further analysis.

Body and Organ Weights

To evaluate the effect of ISIS oligonucleotides on body and organ weights, body weight and liver, spleen, and kidney weights were measured at the end of the study. The body weights at the end of the study were compared with body weight at pre-dose. The organ weights of the mice treated with antisense oligonucleotides were compared with the corresponding organ weights of the PBS control. The results are presented in Tables 6 and 7. Treatment with ISIS oligonucleotides did not cause any changes outside the expected range.

TABLE 6

Fold body weight change of CD1 mice compared to pre-dose weights

|  | Body weight change |
|---|---|
| PBS | 1.32 |
| ISIS 474061 | 1.31 |
| ISIS 487657 | 1.26 |
| ISIS 487658 | 1.29 |
| ISIS 487659 | 1.30 |
| ISIS 487660 | 1.37 |
| ISIS 487661 | 1.39 |
| ISIS 487662 | 1.35 |
| ISIS 487663 | 1.28 |
| ISIS 487664 | 1.42 |
| ISIS 489013 | 1.34 |

TABLE 7

Fold organ weight change of CD1 mice compared to the PBS control

| ISIS No | Liver | Kidney | Spleen |
|---|---|---|---|
| 474061 | 1.1 | 0.9 | 1.1 |
| 487657 | 1.4 | 1.0 | 2.2 |
| 487658 | 1.1 | 1.0 | 1.5 |
| 487659 | 1.1 | 1.0 | 1.5 |
| 487660 | 1.2 | 1.0 | 1.7 |
| 487661 | 1.3 | 0.9 | 1.6 |
| 487662 | 1.3 | 1.0 | 1.1 |
| 487663 | 1.0 | 1.0 | 1.0 |
| 487664 | 1.3 | 0.9 | 1.3 |
| 489013 | 1.2 | 1.0 | 1.5 |

Plasma Chemistry

To evaluate the effect of ISIS oligonucleotides on liver and kidney function, plasma levels of transaminases were measured using an automated clinical chemistry analyzer (Hitachi Olympus AU400e, Melville, N.Y.). Plasma levels of ALT (alanine transaminase) and AST (aspartate transaminase) were measured at the time of sacrifice, and the results are presented in Table 8 in IU/L. Plasma levels of total bilirubin, creatinine, BUN, and albumin were also measured using the same clinical chemistry analyzer and are presented in Table 9.

Mice treated with all oligonucleotides except 487664 did not demonstrate any changes in plasma markers outside the expected range.

TABLE 8

ALT and AST levels (IU/L) of CD1 mice

|  | ALT | AST |
|---|---|---|
| PBS | 44 | 59 |
| ISIS 474061 | 146 | 142 |
| ISIS 487657 | 172 | 242 |
| ISIS 487658 | 90 | 139 |
| ISIS 487659 | 91 | 97 |
| ISIS 487660 | 124 | 97 |
| ISIS 487661 | 259 | 182 |
| ISIS 487662 | 221 | 143 |
| ISIS 487663 | 53 | 61 |
| ISIS 487664 | 508 | 279 |
| ISIS 489013 | 79 | 97 |

TABLE 9

Plasma bilirubin, creatinine, BUN, and albumin levels of CD1 mice

|  | Bilirubin (mg/dL) | Creatinine (mg/dL) | BUN (mg/dL) | Albumin (g/dL) |
|---|---|---|---|---|
| PBS | 0.12 | 0.13 | 26.5 | 2.9 |
| ISIS 474061 | 0.15 | 0.12 | 27.7 | 2.9 |
| ISIS 487657 | 0.15 | 0.11 | 24.2 | 3.0 |
| ISIS 487658 | 0.14 | 0.12 | 28.0 | 2.9 |
| ISIS 487659 | 0.15 | 0.13 | 27.1 | 2.9 |
| ISIS 487660 | 0.14 | 0.12 | 25.4 | 2.9 |
| ISIS 487661 | 0.12 | 0.14 | 29.4 | 2.8 |
| ISIS 487662 | 0.11 | 0.12 | 24.8 | 2.8 |
| ISIS 487663 | 0.18 | 0.11 | 28.1 | 3.0 |
| ISIS 487664 | 0.16 | 0.11 | 26.0 | 2.7 |
| ISIS 489013 | 0.13 | 0.13 | 27.2 | 2.8 |

Example 7: Efficacy and Tolerability of Antisense Oligonucleotides Targeting Human A1AT in Transgenic PiZ Mice Transgenic PiZ mice were originally generated by Sifers et al (Nucl. Acids Res. 15: 1459-1457, 1987) by introducing a 14.4 kb DNA fragment containing the entire A1AT gene plus 2 kb of 5' and 3' flanking genomic DNA sequences into the germline. The mice were treated with ISIS antisense oligonucleotides selected from the studies described above, and the efficacy and tolerability of the antisense oligonucleotides was evaluated.

Treatment

Five to six-week old male and female PiZ mice were maintained at a 12-hour light/dark cycle and fed Purina mouse chow 5001 ad libitum. The mice were acclimated for at least 7 days in the research facility before initiation of the experiment. Groups of four PiZ mice each, consisting of two males and two females, were injected subcutaneously twice a week for 4 weeks with 25 mg/kg (50 mg/kg/week) of ISIS 474061, ISIS 487657, ISIS 487658, ISIS 487659, ISIS 487660, ISIS 487661, ISIS 487662, ISIS 487663, and ISIS 489013. One group of mice was injected subcutaneously twice a week for 4 weeks with 25 mg/kg (50 mg/kg/week) of control oligonucleotide, ISIS 141923 (CCTTCCCTGAAGGTTCCTCC, 5-10-5 MOE gapmer with no known murine target, SEQ ID NO: 43). One group of mice was injected subcutaneously twice a week for 4 weeks with PBS and served as the control group. Blood samples were collected via tail snip prior to dosing and at week 2 and week 4 after dosing. Two days after the last dose, mice were euthanized and organs and plasma were harvested for further analysis.

RNA Analysis

At the end of the study, RNA was extracted from liver tissue for real-time PCR analysis of human A1AT levels using primer probe set RTS3320. Results are presented as percent inhibition of A1AT, relative to PBS control, normalized to the house-keeping gene, Cyclophilin. As shown in Table 10, treatment with some of the ISIS oligonucleotides reduced A1AT mRNA levels. Specifically, treatment with ISIS 487660 reduced A1AT mRNA expression levels. Treatment with the control oligonucleotide, ISIS 141923, did not affect A1AT levels, as expected.

TABLE 10

Percent inhibition of human A1AT mRNA relative to the PBS control

| ISIS No | % inhibition |
|---|---|
| 474061 | 36 |
| 487657 | 29 |
| 487658 | 18 |
| 487659 | 20 |
| 487660 | 76 |
| 487661 | 52 |
| 487662 | 53 |
| 487663 | 23 |
| 489013 | 13 |
| 141923 | 6 |

Protein Analysis

Plasma levels of A1AT were measured with an ELISA kit (Alpco A1AT kit, #30-6752). Results are presented as percent inhibition of A1AT, relative to the PBS control. As shown in Table 11, treatment with some of the ISIS oligonucleotides reduced A1AT plasma levels. Specifically, treatment with ISIS 487660 reduced A1AT levels. Treatment with the control oligonucleotide, ISIS 141923, did not affect A1AT levels, as expected.

TABLE 11

Percent inhibition in human A1AT plasma levels relative to the PBS control

| ISIS No. | week 2 | week 4 |
|---|---|---|
| 474061 | 12 | 18 |
| 487657 | 14 | 18 |
| 487658 | 10 | 17 |
| 487659 | 12 | 16 |
| 487660 | 49 | 61 |
| 487661 | 35 | 41 |
| 487662 | 32 | 50 |
| 487663 | 25 | 41 |
| 489013 | 14 | 29 |

Example 8: Tolerability of Antisense Oligonucleotides Targeting Human A1AT in CD1 Mice CD1 ® mice were treated with ISIS antisense oligonucleotides selected from the studies described above, and evaluated for changes in the levels of various markers.

Treatment

Six to seven-week old male CD1 mice were maintained at a 12-hour light/dark cycle and fed Purina mouse chow 5001 ad libitum. The mice were acclimated for at least 7 days in the research facility before initiation of the experiment. Groups of four CD1 mice each were injected subcutaneously twice a week for 6 weeks with 50 mg/kg (100 mg/kg/week) of ISIS 489009, ISIS 489010, ISIS 496346, ISIS 496360, ISIS 496386, ISIS 496387, ISIS 496388, ISIS 496391, ISIS 493692, ISIS 496393, ISIS 496404, ISIS 496405, ISIS 496406, and ISIS 496407. Blood samples were collected via tail snip prior to dosing and at weeks 2, 3, and 4 after dosing. Three days after the last dose at each time point, mice were euthanized and organs and plasma were harvested for further analysis.

Plasma Chemistry

To evaluate the effect of ISIS oligonucleotides on liver and kidney function, plasma levels of transaminases, bilirubin, BUN, albumin, and creatinine were measured using an automated clinical chemistry analyzer (Hitachi Olympus AU400e, Melville, N.Y.). Plasma levels were measured at the time of sacrifice, and the results are presented in Table 12.

Mice treated with all oligonucleotides except 489009 and ISIS 496388 did not demonstrate any changes in plasma chemistry markers outside the expected range and, therefore, met tolerability requirements. Specifically, treatment with ISIS 496407 was deemed tolerable.

TABLE 12

Levels of plasma chemistry markers of CD1 mice

|  | ALT (IU/L) | AST (IU/L) | Bilirubin (mg/dL) | BUN (mg/dL) | Albumin (g/dL) | Creatinine (mg/dL) |
| --- | --- | --- | --- | --- | --- | --- |
| PBS | 48 | 65 | 0.15 | 22.6 | 2.9 | 0.17 |
| ISIS 489009 | 695 | 412 | 0.19 | 23.8 | 2.8 | 0.16 |
| ISIS 489010 | 166 | 225 | 0.19 | 21.1 | 2.9 | 0.15 |
| ISIS 496346 | 131 | 111 | 0.17 | 25.4 | 2.8 | 0.18 |
| ISIS 496360 | 55 | 71 | 0.15 | 25.5 | 3.0 | 0.16 |
| ISIS 496386 | 53 | 79 | 0.16 | 21.3 | 2.9 | 0.17 |
| ISIS 496387 | 84 | 134 | 0.12 | 22.4 | 2.7 | 0.18 |
| ISIS 496388 | 528 | 419 | 0.11 | 23.6 | 2.4 | 0.16 |
| ISIS 496391 | 107 | 149 | 0.14 | 22.4 | 2.8 | 0.16 |
| ISIS 496392 | 64 | 116 | 0.11 | 24.3 | 2.6 | 0.13 |
| ISIS 496393 | 130 | 115 | 0.10 | 26.6 | 3.0 | 0.17 |
| ISIS 496404 | 74 | 91 | 0.18 | 21.6 | 3.0 | 0.13 |
| ISIS 496405 | 79 | 103 | 0.12 | 23.6 | 2.8 | 0.14 |
| ISIS 496406 | 81 | 99 | 0.14 | 21.3 | 2.8 | 0.15 |
| ISIS 496407 | 71 | 102 | 0.19 | 18.2 | 2.7 | 0.14 |

Example 9: Efficacy and Tolerability of Antisense Oligonucleotides Targeting Human A1AT in PiZ Mice PiZ mice were treated with ISIS antisense oligonucleotides selected from the studies described above and evaluated for changes in the levels of various markers.

Treatment

Female and male PiZ mice were maintained at a 12-hour light/dark cycle and fed Purina mouse chow 5001 ad libitum. The mice were acclimated for at least 7 days in the research facility before initiation of the experiment. Groups of four PiZ mice each were injected subcutaneously twice a week for 4 weeks with 25 mg/kg (50 mg/kg/week) of ISIS 487660, ISIS 487661, ISIS 487662, ISIS 489010, ISIS 496346, ISIS 496360, ISIS 496386, ISIS 496387, ISIS 496391, ISIS 496392, ISIS 496393, ISIS 496404, ISIS 496405, ISIS 496406, and ISIS 496407. A group of four PiZ mice was injected subcutaneously twice a week for 4 weeks with PBS and served as the control group. Blood samples were collected via tail snip prior to dosing and at days 12 and 27 after dosing. Three days after the last dose at each time point, mice were euthanized and organs and plasma were harvested for further analysis.

RNA Analysis

At the end of the study, RNA was extracted from liver tissue for real-time PCR analysis of A1AT using human primer probe set RTS3320. Results are presented as percent inhibition of human A1AT, relative to PBS control, normalized to RIBOGREEN®. As shown in Table 13, treatment with some of the ISIS oligonucleotides reduced A1AT mRNA levels. Specifically, ISIS 487660, ISIS 487662, ISIS 496386, ISIS 496387, ISIS 496392, ISIS 496404, and ISIS 496407 reduced A1AT mRNA levels.

TABLE 13

Percent inhibition of human A1AT mRNA relative to the PBS control

| ISIS No | % |
| --- | --- |
| 487660 | 72 |
| 487661 | 54 |
| 487662 | 75 |
| 489010 | 49 |
| 496346 | 36 |
| 496360 | 24 |
| 496386 | 87 |
| 496387 | 86 |
| 496391 | 69 |
| 496392 | 73 |
| 496393 | 49 |
| 496404 | 70 |
| 496405 | 49 |
| 496406 | 74 |
| 496407 | 89 |

Example 10: Tolerability of Antisense Oligonucleotides Targeting Human A1AT in Sprague-Dawley Rats Sprague-Dawley rats are a multipurpose model of rats frequently utilized for safety and efficacy testing. The rats were treated with ISIS antisense oligonucleotides selected from the studies described in Examples 8 and 9, and evaluated for changes in the levels of various markers.

Treatment

Groups of four Sprague-Dawley rats each were injected subcutaneously twice a week for 6 weeks with 50 mg/kg (100 mg/kg/week) of ISIS 487660, ISIS 487662, ISIS 496386, ISIS 496387, ISIS 496392, ISIS 496406, and ISIS 496407. A group of four Sprague-Dawley rats was injected subcutaneously twice a week for 6 weeks with PBS and served as the control group. Three days after the last dose at each time point, the rats were euthanized and organs and plasma were harvested for further analysis.

Plasma Chemistry

To evaluate the effect of ISIS oligonucleotides on liver and kidney function, plasma levels of transaminases, BUN, albumin, and creatinine were measured using an automated clinical chemistry analyzer (Hitachi Olympus AU400e, Melville, N.Y.). Plasma levels were measured at the time of sacrifice, and the results are presented in Table 14.

Rats treated with ISIS oligonucleotides did not demonstrate changes in plasma chemistry markers outside the expected range and, therefore, were deemed tolerable in this regard.

TABLE 14

Levels of plasma chemistry markers of Sprague-Dawley rats

|  | ALT (IU/L) | AST (IU/L) | BUN (mg/dL) | Albumin (g/dL) | Creatinine (mg/dL) |
|---|---|---|---|---|---|
| PBS | 51 | 64 | 20 | 4.4 | 0.20 |
| ISIS 487660 | 42 | 70 | 22 | 3.3 | 0.28 |
| ISIS 487662 | 48 | 104 | 29 | 3.0 | 0.26 |
| ISIS 496386 | 43 | 85 | 23 | 3.3 | 0.29 |
| ISIS 496387 | 42 | 74 | 23 | 3.0 | 0.28 |
| ISIS 496392 | 42 | 78 | 21 | 3.3 | 0.28 |
| ISIS 496406 | 70 | 159 | 24 | 2.8 | 0.23 |
| ISIS 496407 | 45 | 82 | 21 | 3.1 | 0.26 |

Body and Organ Weights

To evaluate the effect of ISIS oligonucleotides on body and organ weights, body weight and liver, spleen, and kidney weights were measured two days before the rats were euthanized and organ weights were measured at the end of the study. The results are presented in Table 15. Treatment with ISIS oligonucleotides, except ISIS 496406, did not cause any changes outside the expected range and, therefore, were deemed tolerable in this regard.

TABLE 15

Body and organ weights (in grams) of Sprague-Dawley rats

|  | Body weight | Liver | Kidney | Spleen |
|---|---|---|---|---|
| PBS | 473 | 1.0 | 1.0 | 1.0 |
| ISIS 487660 | 392 | 1.3 | 1.1 | 4.1 |
| ISIS 487662 | 376 | 1.3 | 1.3 | 3.7 |
| ISIS 496386 | 385 | 1.2 | 1.1 | 4.4 |
| ISIS 496387 | 409 | 1.1 | 1.1 | 4.1 |
| ISIS 496392 | 368 | 1.2 | 1.1 | 3.0 |
| ISIS 496406 | 340 | 1.3 | 1.2 | 7.0 |
| ISIS 496407 | 377 | 1.1 | 1.1 | 3.9 |

Example 11: Dose Response of Antisense Oligonucleotides Targeting Human A1AT in PiZ Mice PiZ mice were treated with ISIS antisense oligonucleotides selected from the studies described above and evaluated for changes in the levels of various markers.

Treatment

Female and male PiZ mice were maintained at a 12-hour light/dark cycle and fed Purina mouse chow 5001 ad libitum. The mice were acclimated for at least 7 days in the research facility before initiation of the experiment. Groups of four PiZ mice each were injected subcutaneously twice a week for 4 weeks with 12.5 mg/kg, 25 mg/kg, or 37.5 mg/kg of ISIS 487660, ISIS 487662, ISIS 489010, ISIS 496386, ISIS 496392, ISIS 496393, ISIS 496404, and ISIS 496407 (weekly doses of 25 mg/kg, 50 mg/kg, and 75 mg/kg). One group of four PiZ mice was injected subcutaneously twice a week for 4 weeks with 37.5 mg/kg (75 mg/kg/week) of ISIS 141923. One group of four PiZ mice was injected subcutaneously twice a week for 4 weeks with PBS and served as the control group. Blood samples were collected via tail snip prior to dosing and at week 4 after dosing. Three days after the last dose at each time point, mice were euthanized and organs and plasma were harvested for further analysis.

RNA Analysis

At the end of the study, RNA was extracted from liver tissue for real-time PCR analysis of A1AT using human primer probe set RTS3320 (forward sequence GGAGAT-GCTGCCCAGAAGAC, designated herein as SEQ ID NO: 48; reverse sequence GCTGGCGGTATAGGCTGAAG, designated herein as SEQ ID NO: 49; probe sequence ATCAGGATCACCCAACCTTCAACAAGATCA, designated herein as SEQ ID NO: 50). Results are presented as percent inhibition of human A1AT, relative to PBS control, normalized to RIBOGREEN®. As shown in Table 16, treatment with ISIS 487660, ISIS 496386, and ISIS 496407 reduced A1AT mRNA levels. Treatment with the control oligonucleotide, ISIS 141923, did not affect A1AT mRNA expression, as expected.

TABLE 16

Percent inhibition of human A1AT mRNA relative to the PBS control

| ISIS No | 25 mg/kg | 50 mg/kg | 75 mg/kg |
|---|---|---|---|
| 487660 | 40 | 61 | 58 |
| 487662 | 19 | 52 | 51 |
| 489010 | 0 | 4 | 9 |
| 496386 | 47 | 71 | 84 |
| 496392 | 10 | 26 | 39 |
| 496393 | 0 | 0 | 0 |
| 496404 | 0 | 3 | 27 |
| 496407 | 22 | 51 | 76 |

Protein Analysis

Plasma levels of A1AT were measured at week 4 with an ELISA kit (Alpco A1AT kit, #30-6752). Results are presented as percent inhibition of A1AT, relative to pre-dose levels. As shown in Table 17, treatment with most of the ISIS oligonucleotides reduced A1AT plasma levels. Specifically, treatment with ISIS 487660, ISIS 487662, ISIS 496386, and ISIS 496407 reduced A1AT plasma levels. Treatment with the control oligonucleotide, ISIS 141923, did not affect A1AT levels, as expected.

TABLE 17

Percent change in human A1AT plasma levels relative to pre-dose levels

| ISIS No | 25 mg/kg | 50 mg/kg | 75 mg/kg |
|---|---|---|---|
| 487660 | 66 | 76 | 83 |
| 487662 | 42 | 68 | 73 |
| 489010 | 24 | 22 | 36 |
| 496386 | 67 | 82 | 88 |
| 496392 | 28 | 48 | 62 |
| 496393 | 12 | 34 | 32 |
| 496404 | 47 | 58 | 56 |
| 496407 | 46 | 65 | 88 |

Example 12: Dose-Dependent Antisense Inhibition of Human A1AT in PiZ Mouse Primary Hepatocytes Gapmers from the study described in Example 11 were also tested at various doses in PiZ mouse primary hepatocytes. Cells were plated at a density of 25,000 cells per well and transfected using electroporation with 0.63 µM, 2.00 µM, 6.32 µM, 20.00 µM, 63.2 µM, and 200.0 µM concentrations of antisense oligonucleotide, as specified in Table 18. After a treatment period of approximately 16 hours, RNA was isolated from the cells and A1AT mRNA levels were measured by quantitative real-time PCR. Human A1AT primer probe set RTS3335_MGB (forward sequence GACCACCGTGAAGGTGCCTAT, designated herein as SEQ ID NO: 51; reverse sequence GGACAGCTTCTTACAGTGCTGGAT, designated as SEQ ID NO: 52; probe sequence ATGAAGCGTTTAGGCATGTT, designated herein as SEQ ID NO: 53) was used to measure mRNA levels. A1AT mRNA levels were adjusted according to total RNA content, as measured by RIBOGREEN®. Results are presented as percent inhibition of A1AT, relative to untreated control cells.

The half maximal inhibitory concentration ($IC_{50}$) of each oligonucleotide is also presented in Table 18. A1AT mRNA levels were reduced in a dose-dependent manner in antisense oligonucleotide treated cells.

Example 13: Effect of ISIS Antisense Oligonucleotides Targeting Human A1AT in Cynomolgus Monkeys Cynomolgus monkeys were treated with ISIS antisense oligonucleotides selected from studies described above. Antisense oligonucleotide efficacy and tolerability were evaluated. The human antisense oligonucleotides tested are also cross-reactive with the complement of the rhesus genomic sequence NW_001121215.1 truncated from nucleotides 7483001 to 7503000 (designated herein as SEQ ID NO: 14). The greater the complementarity between the human oligonucleotide and the rhesus monkey sequence, the more likely the human oligonucleotide can cross-react with the rhesus monkey sequence. The start and stop sites of each oligonucleotide to SEQ ID NO: 1 and SEQ ID NO: 14 are presented in Table 19. "SEQ ID NO: 1 Start Site" indicates the 5'-most nucleotide to which the gapmer is targeted in the human sequence. "SEQ ID NO: 1 Stop Site" indicates the 3'-most nucleotide to which the gapmer is targeted in the human sequence. "SEQ ID NO: 14 Start Site" indicates the 5'-most nucleotide to which the gapmer is targeted in the rhesus monkey gene sequence. "SEQ ID NO: 14 Stop Site" indicates the 3'-most nucleotide to which the gapmer is targeted in the rhesus monkey gene sequence. "Mismatches to SEQ ID NO: 14" are the number of mismatches in nucleobases the human oligonucleotide has with the rhesus genomic sequence.

TABLE 19

Antisense oligonucleotides complementary to SEQ ID NO: 1 and SEQ ID NO: 14

| SEQ ID 1 Start Site | SEQ ID 1 Stop Site | SEQ ID 14 Start Site | SEQ ID 14 Start Site | Mismatches to SEQ ID 14 | Sequence | ISIS No | Motif | SEQ ID NO |
|---|---|---|---|---|---|---|---|---|
| 1575 | 1594 | 14921 | 14940 | 0 | CCAGCTCAACCCTTCTTTAA | 487660 | 5-10-5 | 38 |
| 1577 | 1596 | 14923 | 14942 | 0 | GACCAGCTCAACCCTTCTTT | 487662 | 5-10-5 | 40 |
| 1565 | 1584 | 14911 | 14930 | 1 | CCTTCTTTAATGTCATCCAG | 496386 | 5-10-5 | 30 |
| 1571 | 1590 | 14917 | 14936 | 0 | CTCAACCCTTCTTTAATGTC | 496392 | 5-10-5 | 34 |
| 1421 | 1440 | 14767 | 14786 | 0 | GGGTTTGTTGAACTTGACCT | 496393 | 5-10-5 | 23 |
| 1561 | 1580 | 14907 | 14926 | 1 | CTTTAATGTCATCCAGGGAG | 496404 | 5-10-5 | 26 |
| 1564 | 1583 | 14910 | 14929 | 1 | CTTCTTTAATGTCATCCAGG | 496407 | 5-10-5 | 29 |

TABLE 18

Dose-dependent antisense inhibition of human A1AT in PiZ mouse primary hepatocytes

| ISIS No | 0.63 µM | 2.00 µM | 6.32 µM | 20.0 µM | 63.2 µM | 200.0 µM | $IC_{50}$ (µM) |
|---|---|---|---|---|---|---|---|
| 487660 | 0 | 60 | 87 | 90 | 87 | 93 | 0.3 |
| 487662 | 0 | 27 | 77 | 86 | 85 | 93 | 0.4 |
| 489010 | 0 | 0 | 12 | 41 | 82 | 95 | 2.3 |
| 496392 | 0 | 22 | 81 | 96 | 95 | 96 | 0.4 |
| 496393 | 0 | 12 | 62 | 91 | 96 | 97 | 0.5 |
| 492404 | 0 | 10 | 76 | 95 | 97 | 97 | 0.4 |
| 492386 | 0 | 43 | 85 | 96 | 96 | 97 | 0.3 |
| 492407 | 0 | 30 | 74 | 96 | 96 | 97 | 0.4 |

Treatment

Prior to the study, 36 cynomolgus monkeys were kept in quarantine for a 5-week period, during which the animals were observed daily for general health. The monkeys were 2-3 years old and weighed between 2 and 5 kg. Groups of four randomly assigned male cynomolgus monkeys each were injected subcutaneously with ISIS oligonucleotide or PBS using a stainless steel dosing needle and syringe of appropriate size into the intracapsular region and outer thigh of the monkeys. Seven groups were dosed four times a week for the first week (days 1, 3, 5, and 7) as loading doses, and subsequently once a week for weeks 2-12, with 50 mg/kg of ISIS 487660, ISIS 487662, ISIS 496386, ISIS 496392, ISIS 496393, ISIS 496404, or ISIS 496407. One group was injected subcutaneously with 25 mg/kg of ISIS 496407 four times a week for the first week (days 1, 3, 5, and 7) as loading doses, and subsequently once a week for weeks 2-13. A control group of monkeys was injected with PBS subcutaneously four times a week for the first week (days 1, 3, 5, and 7), and subsequently once a week for weeks 2-13.

Hepatic Target Reduction
RNA Analysis

On day 86, RNA was extracted from liver tissue for real-time PCR analysis of A1AT using primer probe set rhSERPINA1_LTS00903 ((forward sequence TCTT-TAAAGGCAAATGGGAGAGA, designated herein as SEQ ID NO: 54; reverse sequence TGCCTAAACGCCTCAT-CATG, designated herein as SEQ ID NO: 55; probe sequence CCACGTGGACCAGGCGACCA, designated herein as SEQ ID NO: 56). Results are presented as percent inhibition of A1AT mRNA, relative to PBS control, normalized to the house keeping gene Cyclophilin. Similar results were obtained on normalization with RIBOGREEN®. As shown in Table 20, treatment with ISIS antisense oligonucleotides resulted in reduction of A1AT mRNA in comparison to the PBS control.

TABLE 20

Percent Inhibition of A1AT mRNA in the cynomolgus monkey liver relative to the PBS control

| ISIS No | Maintenance Dose (mg/kg/wk) | % inhibition (normalized RIBOGREEN) | % inhibition (normalized Cyclophilin) |
|---|---|---|---|
| 487660 | 50 | 83 | 87 |
| 487662 | 50 | 54 | 37 |
| 496386 | 50 | 51 | 38 |
| 496392 | 50 | 63 | 55 |
| 496393 | 50 | 33 | 8 |
| 496404 | 50 | 12 | 3 |
| 496407 | 50 | 45 | 34 |
| 496407 | 25 | 25 | 1 |

Protein Analysis

On day 85, monkeys in all groups were fasted overnight. The next day, approximately 1 mL of blood was collected into tubes containing the potassium salt of EDTA. The tubes were centrifuged at 3,000 rpm for 10 min at room temperature to obtain plasma. The plasma samples from all groups were assayed in an automated clinical chemistry analyzer (Hitachi Olympus AU400e, Melville, N.Y.) to measure A1AT protein levels using an antibody based assay designed by Olympus. As shown in Table 21, treatment with some of the ISIS antisense oligonucleotides resulted in reduction of A1AT protein levels in comparison to pre-dose levels on day −13.

TABLE 21

Percent Inhibition of plasma A1AT protein levels in cynomolgus monkey relative to the PBS control

| ISIS No | Maintenance Dose (mg/kg/wk) | % inhibition |
|---|---|---|
| 487660 | 50 | 83 |
| 487662 | 50 | 42 |
| 496386 | 50 | 30 |
| 496392 | 50 | 49 |
| 496393 | 50 | 7 |
| 496404 | 50 | 5 |
| 496407 | 50 | 27 |
| 496407 | 25 | 29 |

Tolerability Studies
Body and Organ Weight Measurements

To evaluate the effect of ISIS oligonucleotides on the overall health of the animals, body and organ weights were measured at day 86. Body weights were measured and are presented in Table 22, expressed relative to pre-dose levels on day 1. Organ weights were measured and the data is also presented in Table 22, expressed relative to the body weight. Body and organ weights after treatment with ISIS oligonucleotides were within the expected range.

TABLE 22

Body and organ weights in the cynomolgus monkey (expressed in relative terms)

| ISIS No | Dose (mg/kg/wk) | Body weight | Spleen | Kidney | Liver |
|---|---|---|---|---|---|
| PBS | — | 1.05 | 0.1 | 0.5 | 2.2 |
| 487660 | 50 | 1.07 | 0.2 | 0.8 | 3.0 |
| 487662 | 50 | 1.04 | 0.4 | 0.7 | 3.1 |
| 496386 | 50 | 1.00 | 0.4 | 1.8 | 3.8 |
| 496392 | 50 | 1.11 | 0.3 | 0.6 | 3.0 |
| 496393 | 50 | 1.10 | 0.3 | 0.6 | 3.0 |
| 496404 | 50 | 1.01 | 0.3 | 0.9 | 3.2 |
| 496407 | 50 | 1.01 | 0.3 | 0.9 | 3.5 |
| 496407 | 25 | 1.10 | 0.3 | 0.7 | 3.0 |

Liver Function

To evaluate the effect of ISIS oligonucleotides on hepatic function, approximately 1.5 mL of blood samples were collected from all the study groups. The monkeys were fasted overnight prior to blood collection. Blood was collected for serum separation in tubes without anticoagulant. The tubes were kept at room temperature for a minimum of 90 min and then centrifuged at 3,000 rpm for 10 min. Levels of various liver function markers were measured using a Toshiba 200FR NEO chemistry analyzer (Toshiba Co., Japan). Plasma levels of ALT and AST were measured and the results are presented in Table 23, expressed in IU/L. Bilirubin and albumin were similarly measured and are presented in Table 34. Liver function after treatment with ISIS oligonucleotides was within the expected range.

TABLE 23

Effect of antisense oligonucleotide treatment on liver function markers in cynomolgus monkey plasma

| ISIS No | Dose (mg/kg/wk) | ALT (IU/L) | AST (IU/L) | Albumin (g/dL) | Bilirubin (mg/dL) |
|---|---|---|---|---|---|
| PBS | — | 38 | 50 | 4.3 | 0.15 |
| 487660 | 50 | 52 | 78 | 4.1 | 0.13 |
| 487662 | 50 | 99 | 82 | 3.9 | 0.11 |
| 496386 | 50 | 71 | 77 | 3.3 | 0.10 |
| 496392 | 50 | 85 | 64 | 4.0 | 0.14 |
| 496393 | 50 | 68 | 62 | 4.2 | 0.16 |
| 496404 | 50 | 122 | 130 | 3.8 | 0.17 |
| 496407 | 50 | 56 | 64 | 3.6 | 0.13 |
| 496407 | 25 | 50 | 50 | 3.5 | 0.13 |

Kidney Function

To evaluate the effect of ISIS oligonucleotides on kidney function, blood samples were collected from all the study groups. The monkeys were fasted overnight prior to blood collection. Blood was collected for serum separation in tubes without anticoagulant. The tubes were kept at room temperature for a minimum of 90 min and then centrifuged at 3,000 rpm for 10 min. Levels of BUN and creatinine were measured using a Toshiba 200FR NEO chemistry analyzer (Toshiba Co., Japan). Results are presented in Table 24, expressed in mg/dL.

Fresh urine from all animals was collected for urine analysis using a clean cage pan on wet ice. The urine samples were analyzed by the Toshiba 200FR NEO chemistry analyzer (Toshiba Co., Japan) for their protein to creatinine (P/C) ratio. The data is presented in Table 25.

Kidney function after treatment with ISIS oligonucleotides was within the expected range.

TABLE 24

Effect of antisense oligonucleotide treatment on plasma BUN and creatinine levels in cynomolgus monkeys

| ISIS No | Dose (mg/kg/wk) | BUN (mg/dL) | Creatinine (mg/dL) |
|---|---|---|---|
| PBS | — | 25 | 0.9 |
| 487660 | 50 | 26 | 0.9 |
| 487662 | 50 | 26 | 1.0 |
| 496386 | 50 | 69 | 1.5 |
| 496392 | 50 | 28 | 1.0 |
| 496393 | 50 | 24 | 0.9 |
| 496404 | 50 | 28 | 1.0 |
| 496407 | 50 | 42 | 1.3 |
| 496407 | 25 | 36 | 1.1 |

TABLE 25

Effect of antisense oligonucleotide treatment on P/C ratio in the urine of cynomolgus monkeys

| ISIS No | Dose (mg/kg/wk) | P/C |
|---|---|---|
| PBS | — | 0.0 |
| 487660 | 50 | 0.1 |
| 487662 | 50 | 0.0 |
| 496386 | 50 | 5.9 |
| 496392 | 50 | 0.0 |
| 496393 | 50 | 0.1 |
| 496404 | 50 | 0.4 |
| 496407 | 50 | 0.1 |
| 496407 | 25 | 1.6 |

Hematology

To evaluate any effect of ISIS oligonucleotides in cynomolgus monkeys on hematologic parameters, approximately 0.5 mL of blood was collected on day 86 from each of the available study animals in tubes containing $K_2$-EDTA. The animals were fasted overnight prior to blood collection. Samples were analyzed for red blood cell (RBC) count, white blood cells (WBC) count, individual white blood cell counts, such as that of monocytes, neutrophils, lymphocytes, as well as for platelet count, hemoglobin content and hematocrit, using an ADVIA120 hematology analyzer (Bayer, USA). The data is presented in Tables 26 and 27.

Hematologic parameters after treatment with ISIS oligonucleotides were within the expected range.

TABLE 26

Effect of antisense oligonucleotide treatment on various blood cells in cynomolgus monkeys

| ISIS No | Dose (mg/kg/wk) | WBC ($\times 10^3/\mu L$) | RBC ($\times 10^6/\mu L$) | Platelets ($\times 10^3/\mu L$) | Neutrophils (%) | Lymphocytes (%) | Monocytes (%) |
|---|---|---|---|---|---|---|---|
| PBS | — | 13.2 | 6.1 | 490.5 | 30.8 | 62.9 | 3.6 |
| 487660 | 50 | 13.2 | 5.8 | 472.8 | 16.1 | 75.9 | 5.0 |
| 487662 | 50 | 11.0 | 5.5 | 413.0 | 19.0 | 65.7 | 8.5 |
| 496386 | 50 | 12.4 | 5.4 | 269.5 | 45.8 | 44.6 | 5.5 |
| 496392 | 50 | 12.9 | 5.9 | 339.5 | 37.4 | 52.5 | 5.4 |
| 496393 | 50 | 12.7 | 5.8 | 343.5 | 34.4 | 59.6 | 2.7 |
| 496404 | 50 | 13.8 | 6.0 | 445.0 | 38.1 | 53.8 | 4.9 |
| 496407 | 50 | 10.9 | 5.5 | 470.5 | 37.0 | 54.3 | 4.0 |
| 496407 | 25 | 12.8 | 5.4 | 489.8 | 35.9 | 56.5 | 4.2 |

TABLE 27

Effect of antisense oligonucleotide treatment on hematologic parameters in cynomolgus monkeys

| ISIS No | Dose (mg/kg/wk) | Hemoglobin (g/dL) | Hematocrit (%) |
|---|---|---|---|
| PBS | — | 13.0 | 41.9 |
| 487660 | 50 | 12.8 | 41.2 |
| 487662 | 50 | 12.1 | 39.2 |
| 496386 | 50 | 11.1 | 37.1 |
| 496392 | 50 | 13.4 | 42.7 |
| 496393 | 50 | 12.9 | 40.9 |
| 496404 | 50 | 13.5 | 42.0 |
| 496407 | 50 | 12.4 | 40.6 |
| 496407 | 25 | 11.7 | 38.5 |

Example 14: Efficacy of Antisense Oligonucleotides Targeting Human A1AT in Transgenic PiZ Mice Transgenic PiZ mice were treated with ISIS 496407 and its efficacy was evaluated.

Treatment

Six-week old male and female PiZ mice were maintained at a 12-hour light/dark cycle and fed Purina mouse chow 5001 ad libitum. The mice were acclimated for at least 7 days in the research facility before initiation of the experiment. One cohort of PiZ mice were injected subcutaneously twice a week for 8 weeks with 25 mg/kg (50 mg/kg/week) of ISIS 496407. One cohort of mice was injected subcutaneously twice a week for 8 weeks with PBS and served as the control. Two days after the last dose, mice were euthanized, and organs and plasma were harvested for further analysis.

RNA Analysis

At the end of the study, RNA was extracted from liver tissue for real-time PCR analysis of human A1AT levels using primer probe set RTS3320. Results are presented as percent inhibition of A1AT, relative to PBS control, normalized to the house-keeping gene, Cyclophilin. As shown in Table 28, treatment with ISIS 496407 reduced A1AT mRNA levels in both male and female mice relative to the PBS control.

TABLE 28

Percent inhibition of human A1AT mRNA relative to the PBS control

| | % |
|---|---|
| Male | 93 |
| Female | 81 |

Protein Analysis

Plasma levels of A1AT were measured once every two weeks with an ELISA kit (Alpco A1AT kit, #30-6752). Results are presented as percent inhibition of A1AT, relative to the values taken pre-dose. As shown in Table 29, treatment with ISIS 496407 reduced A1AT plasma levels.

TABLE 29

Percent inhibition in human A1AT plasma levels relative to the PBS control

|  | Week 2 | Week 4 | Week 6 | Week 8 |
| --- | --- | --- | --- | --- |
| Male | 60 | 80 | 90 | 90 |
| Female | 70 | 80 | 80 | 90 |

Analysis of Liver A1AT Protein Aggregates

For separation of soluble and insoluble A1AT protein, 10 mg of whole liver was placed in a buffer consisting of 50 mmol/L Tris HCl (pH 8.0), 150 mmol/L KCl, 5 mmol/L $MgCl_2$, 0.5% Triton X-100, and 80 µL Complete® protease inhibitor stock. The liver tissue was homogenized in a pre-chilled Dounce homogenizer with 30 repetitions and then the suspension was vortexed vigorously. A 1-mL aliquot of the suspension was passed through a 28-gauge needle 10 times to further homogenize the tissue. The total protein concentration of the aliquot was determined. A 5 µg liver sample aliquot was centrifuged at 10,000 g for 30 min at 4° C. The supernatant containing the soluble A1AT fraction was immediately removed into a fresh tube with extreme care being taken to avoid disturbing the cell pellet, or non-soluble fraction. The cell pellet containing the insoluble polymer of A1AT protein was denatured and solubilized by addition of 10 µL of chilled cell lysis buffer (1% Triton X-100, 0.05% deoxycholate and 10 mmol/L EDTA in PBS), vortexing for 30 sec, sonication on ice for 10 min and further vortexing. Both the soluble A1AT fraction and the solubilized A1AT polymer fraction were boiled in 2.5× sample buffer (5% sodium dodecyle sulfate, 50% glycerol, 0.5 mol/L Tris [pH 6.8], 10% beta-mercaptoethanol, 40% double distilled water). The samples were then loaded on an SDS-PAGE. Western analysis was subsequently conducted using goat anti-human alpha-1 antitrypsin Nephelometric serum (DiaSorin Inc, Cat#80502). The bands of the Western blot were quantified using a densitometer and analyzed using ImageJ software. The data indicated that both soluble and insoluble A1AT protein fractions were reduced after treatment with ISIS 496407. Table 30 presents the results for the A1AT polymer fraction, expressed as percentage reduction of the polymer relative to the PBS control.

TABLE 30

Percent inhibition in human A1AT polymer relative to the PBS control

|  | % |
| --- | --- |
| Male | 32 |
| Female | 38 |

Example 15: Effect of Antisense Inhibition of A1AT in Halting Progression of A1AT Deficiency Liver Disease in PiZ Mice The effect of inhibition of A1AT mRNA expression with antisense oligonucleotides on halting the progression of A1AT deficiency liver disease was examined in PiZ mice.

Treatment

Male PiZ mice, 6-8 weeks in age, were randomly divided into treatment groups of 4 mice each. Three treatment groups were injected with 25 mg/kg of ISIS 487660 (SEQ ID NO: 38), administered subcutaneously twice a week for 4, 8, or 12 weeks. Another three groups were injected with PBS, administered subcutaneously twice a week for 4, 8, or 12 weeks. Two PiZ mice with no treatment administered were included to provide baseline measurements. At the end of each treatment period, the mice were euthanized with isoflurane followed by cervical dislocation. Liver tissue was collected and processed for further analysis.

RNA Analysis

RNA isolation was performed using the Invitrogen PureLink™ Total RNA Purification Kit, according to the manufacturer's protocol. RT-PCR was performed and A1AT RNA expression was measured using primer probe set RTS3320 and normalized to RIBOGREEN®.

A1AT mRNA expression was assessed in the liver. As shown in Table 31, A1AT mRNA expression in mice treated with ISIS 487660 was inhibited compared to the control group in all treatment groups. The mRNA expression levels are expressed as percent inhibition of expression levels compared to that in the PBS control.

TABLE 31

Percent inhibition of A1AT mRNA levels (%) compared to the PBS control

| Weeks of treatment | Liver |
| --- | --- |
| 4 | 76 |
| 8 | 89 |
| 12 | 80 |

Protein Analysis

Plasma levels of A1AT were measured once every two weeks with a clinical analyzer and Diasorin antibody to A1AT protein. Results are presented as percent inhibition of A1AT, relative to the values taken pre-dose. As shown in Table 32, treatment with ISIS 487660 reduced A1AT plasma levels in all treatment groups.

TABLE 32

Percent inhibition in human A1AT plasma levels relative to the PBS control

| Weeks of treatment | % inhibition |
| --- | --- |
| 4 | 63 |
| 8 | 65 |
| 12 | 68 |

Quantification of A1AT Globules in the Liver

A well-known characteristic of the A1AT deficiency liver disease is the presence of PAS-positive globules in hepatocytes (Teckman, J. H. et al., Am. J. Physiol. Gastrointest. Liver Physiol. 2002. 283: G1156-G1165). Analysis was performed on a total tissue area of 2,250,000 µm² using Spectrum software system (Aperio, Calif.). Hepatocytes were stained with Period acid-Schiff stain after diastase treatment of the liver sections.

The average diameters of the globules in each treatment group were measured and are presented in Table 33. The total globule area was calculated and is presented in Table 34. The results indicate that treatment with ISIS 487660 reduced or halted globule formation in hepatocytes in all treatment groups.

TABLE 33

Average globule diameter (μM) in PiZ mice

| Weeks of treatment | Treatment groups | Diameter |
|---|---|---|
| — | Baseline | 0.42 |
| 4 | PBS | 1.76 |
|   | ISIS 487660 | 0.31 |
| 8 | PBS | 2.54 |
|   | ISIS 487660 | 0.40 |
| 12 | PBS | 3.33 |
|   | ISIS 487660 | 0.48 |

TABLE 34

Total globule area (μm$^2$) in PiZ mice

| Weeks of treatment | Treatment groups | Area |
|---|---|---|
| — | Baseline | 41,392 |
| 4 | PBS | 95,948 |
|   | ISIS 487660 | 58,218 |
| 8 | PBS | 76,074 |
|   | ISIS 487660 | 61,260 |
| 12 | PBS | 147,753 |
|   | ISIS 487660 | 64,546 |

Analysis of Liver A1AT Protein Aggregates

For separation of soluble and insoluble A1AT protein, 10 mg of whole liver was placed in a buffer consisting of 50 mmol/L Tris HCl (pH 8.0), 150 mmol/L KCl, 5 mmol/L MgCl$_2$, 0.5% Triton X-100, and 80 μL Complete® protease inhibitor stock. The liver tissue was homogenized in a pre-chilled Dounce homogenizer with 30 repetitions and then the suspension was vortexed vigorously. A 1-mL aliquot of the suspension was passed through a 28-gauge needle 10 times to further homogenize the tissue. The total protein concentration of the aliquot was determined. A 5 μg liver sample aliquot was centrifuged at 10,000 g for 30 min at 4° C. The supernatant containing the soluble A1AT fraction was immediately removed into a fresh tube with extreme care being taken to avoid disturbing the cell pellet, or non-soluble fraction. The cell pellet containing the insoluble polymer of A1AT protein was denatured and solubilized by addition of 10 μL of chilled cell lysis buffer (1% Triton X-100, 0.05% deoxycholate and 10 mmol/L EDTA in PBS), vortexing for 30 sec, sonication on ice for 10 min and further vortexing. Both the soluble A1AT fraction and the solubilized A1AT polymer fraction were boiled in 2.5× sample buffer (5% sodium dodecyle sulfate, 50% glycerol, 0.5 mol/L Tris[pH 6.8], 10% beta-mercaptoethanol, 40% double distilled water). The samples were then loaded on an SDS-PAGE. Western analysis was subsequently conducted using goat anti-human alpha-1 antitrypsin Nephelometric serum (DiaSorin Inc, Cat#80502). The bands of the Western blot were quantified using a densitometer and analyzed using ImageJ software. The data indicated that both soluble and insoluble A1AT protein fractions were reduced after treatment with ISIS 496407. Table 35 presents the results for the A1AT polymer fraction, expressed in arbitrary units.

TABLE 35

Human A1AT monomer and polymer levels

| Weeks of treatment | Treatment groups | Monomer | Polymer |
|---|---|---|---|
| 4 | PBS | 238 | 2213 |
|   | ISIS 487660 | 26 | 1327 |
| 8 | PBS | 675 | 2598 |
|   | ISIS 487660 | 106 | 1517 |
| 12 | PBS | 159 | 2317 |
|   | ISIS 487660 | 45 | 1124 |

Example 16: Effect of Antisense Inhibition of A1AT in Preventing the Onset of A1AT Deficiency Liver Disease in PiZ Mice The effect of inhibition of A1AT mRNA expression with antisense oligonucleotides on preventing the onset of A1AT deficiency liver disease was examined in PiZ mice.

Treatment

Male and female PiZ mice, 2 weeks in age, were randomly divided into treatment groups of 4 mice each. One group was injected with 25 mg/kg of ISIS 487660 (SEQ ID NO: 38), administered subcutaneously twice a week for 8 weeks (50 mg/kg/week). Another group was injected with PBS, administered subcutaneously twice a week for 8 weeks. Two mice were kept in a separate group and served to establish baseline values or measurements of various parameters pre-dose. Two PiZ mice with no treatment administered were included to provide baseline measurements. At the end of each treatment period, the mice were euthanized with isoflurane followed by cervical dislocation. Liver tissue was collected and processed for further analysis.

RNA Analysis

RNA isolation was performed using the Invitrogen PureLink™ Total RNA Purification Kit, according to the manufacturer's protocol. RT-PCR was performed and A1AT RNA expression was measured using primer probe set RTS3320 and normalized to RIBOGREEN®.

A1AT mRNA expression was assessed in the liver. A1AT mRNA expression in mice treated with ISIS 487660 was inhibited by 71% compared to the control group in all treatment groups.

Protein Analysis

Plasma levels of A1AT were measured once every two weeks using a clinical analyzer and Diasorin antibody to A1AT protein. Results are presented as percent inhibition of A1AT, relative to the values taken pre-dose. As shown in Table 36, treatment with ISIS 487660 reduced A1AT plasma levels.

TABLE 36

Percent inhibition in human A1AT plasma levels relative to baseline values

| Week | % inhibition |
|---|---|
| 2 | 40 |
| 4 | 40 |
| 6 | 50 |
| 8 | 40 |

Quantification of A1AT Globules in the Liver

Hepatocytes were stained with PAS. Analysis was performed on a total tissue are of 2,250,000 μm$^2$ using Spectrum software system (Aperio, Calif.). Hepatocytes were stained with Periodic acid-Schiff stain after diastase treatment of the liver sections.

The average diameters of the globules in each treatment group were measured and are presented in Table 37. The total globule area in all the groups was calculated and is presented in Table 38. The results indicate that treatment with ISIS 487660 prevented globule formation in hepatocytes in all treatment groups.

TABLE 37

Average globule diameter (µM) in PiZ mice

| Mouse gender | Treatment groups | Diameter |
|---|---|---|
| Both | Baseline | 0.23 |
| Male | PBS | 2.1 |
|  | ISIS 487660 | 0.1 |
| Female | PBS | 2.3 |
|  | ISIS 487660 | 0.1 |

TABLE 38

Total globule area (µm$^2$) in PiZ mice

| Mouse gender | Treatment groups | Area |
|---|---|---|
| Both | Baseline | 31,856 |
| Male | PBS | 63,531 |
|  | ISIS 487660 | 33,053 |
| Female | PBS | 155,564 |
|  | ISIS 487660 | 26,084 |

Analysis of Liver A1AT Protein Aggregates

For separation of soluble and insoluble A1AT protein, 10 mg of whole liver was placed in a buffer consisting of 50 mmol/L Tris HCl (pH 8.0), 150 mmol/L KCl, 5 mmol/L MgCl$_2$, 0.5% Triton X-100, and 80 L Complete protease inhibitor stock. The liver tissue was homogenized in a pre-chilled Dounce homogenizer with 30 repetitions and then the suspension was vortexed vigorously. A 1-mL aliquot of the suspension was passed through a 28-gauge needle 10 times to further homogenize the tissue. The total protein concentration of the aliquot was determined. A 5 µg liver sample aliquot was centrifuged at 10,000 g for 30 min at 4° C. The supernatant containing the soluble A1AT fraction was immediately removed into a fresh tube with extreme care being taken to avoid disturbing the cell pellet, or non-soluble fraction. The cell pellet containing the insoluble polymer of A1AT protein was denatured and solubilized by addition of 10 µL of chilled cell lysis buffer (1% Triton X-100, 0.05% deoxycholate and 10 mmol/L EDTA in PBS), vortexing for 30 sec, sonication on ice for 10 min and further vortexing. Both the soluble A1AT fraction and the solubilized A1AT polymer fraction were boiled in 2.5× sample buffer (5% sodium dodecyle sulfate, 50% glycerol, 0.5 mol/L Tris[pH 6.8], 10% beta-mercaptoethanol, 40% double distilled water). The samples were then loaded on an SDS-PAGE. Western analysis was subsequently conducted using goat anti-human alpha-1 antitrypsin Nephelometric serum (DiaSorin Inc, Cat#80502). The bands of the Western blot were quantified using a densitometer and analyzed using ImageJ software. The data indicated that treatment with ISIS 487660 prevented formation of A1AT protein aggregates in PiZ mice when administered at 2 weeks of age.

Example 17: Effect of Antisense Inhibition of A1AT on Liver Fibrosis in the PiZZ Mice Model PiZZ mice contain the mutant piZ variant of the human A1AT gene. The mice have accumulation of the mutant human protein in the hepatocytes, similar to that in human patients, causing liver necrosis and inflammation (Carlson, J. A. et al., J. Clin. Invest. 1989. 83: 1183-90). The effect of inhibition of A1AT mRNA expression in ameliorating liver fibrosis was examined in PiZZ mice.

Study 1
Treatment

Eight week old PiZZ mice were randomly divided into treatment groups of 5 mice each. A group of mice was injected with 50 mg/kg/week of ISIS 496407, administered subcutaneously for 8 weeks. Another group of mice was injected with PBS, administered subcutaneously for 8 weeks. At the end of each treatment period, the mice were euthanized with isoflurane followed by cervical dislocation. Liver tissue and plasma was collected and processed for further analysis.

A1AT mRNA Analysis

RNA isolation from liver tissue was performed using the Invitrogen PureLink™ Total RNA Purification Kit, according to the manufacturer's protocol. RT-PCR was performed and A1AT RNA expression was measured using primer probe set RTS3320 and normalized to RIBOGREEN®. Hepatic A1AT levels were reduced by 91% in mice treated with ISIS 496407 compared to the PBS control.

Analysis of Liver Fibrosis Markers

Increased levels of TIMP1 play an important role in the pathogenesis of liver fibrosis (Arthur, M. J. et al., J. Gastroenterol. Hepatol. 1998. 13: S33-8). RNA analysis of TIMP-1 levels was conducted using the primer probe set mTimp1_LTS00190 (forward sequence TCATGGAAAGC-CTCTGTGGAT, designated herein as SEQ ID NO: 57; reverse sequence GCGGCCCGTGATGAGA, designated herein as SEQ ID NO: 58; probe sequence CCCACAAGTC-CCAGAACCGCAGTG, designated herein as SEQ ID NO: 59). A decrease in TIMP1 levels may lead to a decrease in fibrosis of an organ or tissue. TIMP1 levels can be used as a marker for fibrosis in an organ or tissue. TIMP1 levels were decreased by 82% in mice treated with ISIS 496407.

In addition, analysis of liver damage was conducted by histochemical staining. Fibrosis deposition was assessed by Sirius Red staining and quantification of the stain intensity and area. Liver sections from mice treated with ISIS 496407 demonstrated a decrease in staining by 76% (0.20 in arbitrary units vs. 0.83 of the PBS control) compared to staining of section of the PBS control.

The results indicate that treatment with ISIS 496407 resulted in decreased liver TIMP1 levels and decreased staining of the liver with Sirius Red. Hence, antisense inhibition of A1AT resulted in decreased fibrosis in this mice model.

Plasma Chemistry

To evaluate the effect of ISIS oligonucleotides on liver and kidney function, plasma levels of transaminases were measured using an automated clinical chemistry analyzer (Hitachi Olympus AU400e, Melville, N.Y.). Plasma levels of ALT (alanine transaminase) and AST (aspartate transaminase) were measured at the time of sacrifice, and the results are presented in Tables 39 and 40 in IU/L.

Mice treated with ISIS 496407 decreased transaminase levels compared to the control, which demonstrated increased levels of both ALT and AST with time. The decrease in transaminase levels indicate a prevention of organ damage, a decrease in organ damage and/or an improvement in organ function in the oligonucleotide treated mice.

TABLE 39

ALT levels (IU/L) of PiZZ mice

|  | Baseline | Week 2 | Week 4 | Week 6 | Week 8 |
| --- | --- | --- | --- | --- | --- |
| PBS | 57 | 73 | 172 | 153 | 101 |
| ISIS 496407 | 59 | 64 | 71 | 64 | 59 |

TABLE 40

AST levels (IU/L) of PiZZ mice

|  | Baseline | Week 2 | Week 4 | Week 6 | Week 8 |
| --- | --- | --- | --- | --- | --- |
| PBS | 95 | 119 | 234 | 166 | 134 |
| ISIS 496407 | 101 | 83 | 90 | 86 | 84 |

Study 2
Treatment

Five week old PiZZ mice were randomly divided into treatment groups of 6 mice each. A group of mice was injected with 50 mg/kg/week of ISIS 487660, administered subcutaneously for 8 weeks, then 25 mg/kg/week for three weeks. Another group of mice was injected with PBS, administered subcutaneously for 11 weeks. At the end of each treatment period, the mice were euthanized with isoflurane followed by cervical dislocation. Liver tissue and plasma was collected and processed for further analysis.

Analysis of Liver Fibrosis Markers

The expression of various genes can be used as markers for fibrosis formation in an organ or tissue. Expression of the following fibrosis markers in the liver were analyzed: collagen type 1, alpha 1; collagen type IV; collagen type III, alpha 1 (Du, W. D. et al., World Gastroenterol. 1999. 5: 397-403); MMP12; MMP13; and TIMP1 (Arthur, M. J. Am. J. Physiol. 2000. 279: G245-G249). The results are presented in Table 41. A decrease in the expression of one or more of these fibrosis markers may be correlative and/or causative of a decrease in fibrosis of an organ or tissue.

TABLE 41

Inhibition of levels of fibrosis markers in PiZZ mice

|  | % inhibition |
| --- | --- |
| Collagen type 1, alpha 1 | 75 |
| Collagen type III, alpha 1 | 57 |
| Collagen type IV | 21 |
| MMP12 | 0 |
| MMP13 | 31 |
| TIMP1 | 67 |

In addition, analysis of liver damage was conducted by histochemical staining. Fibrosis deposition was assessed by Sirius Red staining and quantification of the stain intensity and area. Liver sections from mice treated with ISIS 487660 demonstrated a decrease in staining by 69% (0.83 in arbitrary units vs. 2.65 of the PBS control) compared to staining of section of the PBS control. Levels of alpha-smooth muscle actin (SMA), a myofibroblast marker (Hinz, B. et al., Am. J. Pathol. 2001. 159: 1009-1020), were also assessed. SMA levels were measured in both groups. Liver sections from mice treated with ISIS 487660 demonstrated a decrease in levels by 40% (0.83 in arbitrary units vs. 1.38 of the PBS control) compared to levels in the sections of the PBS control.

The results indicate that treatment with an A1AT oligonucleotide, ISIS 487660, inhibited A1AT expression leading to a decrease in liver fibrosis as indicated by histochemical staining and the decrease of multiple liver fibrosis markers.

Plasma Chemistry

To evaluate the effect of ISIS oligonucleotides on liver and kidney function, plasma levels of transaminases were measured using an automated clinical chemistry analyzer (Hitachi Olympus AU400e, Melville, N.Y.). Plasma levels of ALT, and AST were measured at the time of sacrifice, and the results are presented in Tables 42 and 43 in IU/L.

Mice treated with ISIS 487660 decreased liver chemistry marker levels compared to the control with time. The decrease in transaminase levels indicate a prevention of organ damage, a decrease in organ damage and/or an improvement in organ function in the oligonucleotide treated mice.

TABLE 42

ALT levels (IU/L) of PiZZ mice

|  | Day 1 | Day 15 | Day 35 | Day 56 | Day 77 |
| --- | --- | --- | --- | --- | --- |
| PBS | 67 | 56 | 74 | 146 | 78 |
| ISIS 487660 | 73 | 34 | 42 | 48 | 58 |

TABLE 43

AST levels (IU/L) of PiZZ mice

|  | Day 1 | Day 15 | Day 35 | Day 56 | Day 77 |
| --- | --- | --- | --- | --- | --- |
| PBS | 102 | 105 | 128 | 188 | 106 |
| ISIS 487660 | 98 | 56 | 64 | 67 | 69 |

Example 18: Effect of Antisense Inhibition of A1AT on Reversal of Aggregate Formation in the PiZ Mice Model The effect of inhibition of A1AT mRNA expression with antisense oligonucleotides on reversing A1AT aggregate formation was examined in PiZ mice. PiZ mice, at 16 weeks of age, were monitored for 20 weeks for the effect of antisense inhibition in reversing aggregate formation.

Treatment

Male PiZ mice, 16 weeks in age, were randomly divided into treatment groups of 4 mice each. One group was injected with 25 mg/kg of ISIS 487660 (SEQ ID NO: 38), administered subcutaneously twice a week for 20 weeks (50 mg/kg/week). Another group was injected with PBS, administered subcutaneously twice a week for 20 weeks. At the end of each treatment period, the mice were euthanized. Liver tissue was collected and processed for further analysis.

Protein Analysis

PiZ mouse livers were homogenized and the soluble and insoluble human A1AT fractions were separated. Both fractions were separated on sodium dodecyl sulfate-polyacrylamide gel electrophoresis (SDS-PAGE) equal amounts of total liver protein were loaded per soluble-insoluble pair in quantitative experiments. A1AT protein was detected by a polyclonal antibodies against human A1AT purchased from DiaSorin, Inc. (Stillwater, Minn.) and the secondary antibody was HRP-conjugated rabbit anti-goat antibody (Jackson ImmunoResearch). Western blot was quantitated with ImageQuant. Results are presented as percent inhibition of A1AT, relative to the values taken pre-dose at 16 weeks (baseline). As shown in Table 1, treatment with ISIS 487660 reversed insoluble A1AT protein accumulation in the liver compared to the PBS control in older mice.

TABLE 44

Percentage of human A1AT liver protein levels relative to baseline values

|  | Levels of soluble A1AT | Levels of insoluble A1AT |
| --- | --- | --- |
| PBS | 58 | 107 |
| ISIS 487660 | 10 | 65 |

Analysis of Liver A1AT Protein Aggregates

Histochemical staining for total A 1AT protein and Periodic acid-Schiff with diastase treatment stain (PAS-D, for A1AT aggregates) of 16-week mice (the age of the mice at the start of the study, which is taken as baseline), PBS control-treated mice, and ISIS 487660 treated-mice was performed. Liver sections from mice treated with ISIS 487660 exhibited decreased staining of total A1AT, compared to compared to PBS control and baseline. Liver sections were also stained with PAS-D. Positive PAS-D staining in periportal hepatocytes indicate A1AT accumulation in the liver, which is associated with the A1AT deficiency disorder. Sections from mice treated with ISIS 487660 exhibited decreased staining of PAS-D compared to PBS control and baseline.

What is claimed is:

1. A compound comprising a modified oligonucleotide consisting of 12 to 30 linked nucleosides and having a nucleobase sequence comprising a portion of at least 12 contiguous nucleobases complementary to an equal length portion of nucleobases 1561 to 1597 of SEQ ID NO: 1, wherein the nucleobase sequence of the modified oligonucleotide is at least 90% complementary to SEQ ID NO: 1.

2. The compound of claim 1, wherein the nucleobase sequence comprises at least 20 contiguous nucleobases complementary to an equal length portion of nucleobases 1561-1597 of SEQ ID NO: 1.

3. The compound of claim 1, wherein the modified oligonucleotide consists of 18 to 24 linked nucleosides.

4. The compound of claim 1, wherein the nucleobase sequence of the modified oligonucleotide is at least 95% complementary to SEQ ID NO: 1.

5. The compound of claim 1, consisting of a single-stranded modified oligonucleotide.

6. The compound of claim 5, wherein at least one internucleoside linkage is a modified internucleoside linkage.

7. The compound of claim 6, wherein at least one modified internucleoside linkage is a phosphorothioate linkage.

8. The compound of claim 5, wherein at least one nucleoside comprises a modified nucleobase.

9. The compound of claim 8, wherein the modified nucleobase is a 5-methylcytosine.

10. The compound of claim 5, wherein the modified oligonucleotide comprises at least one modified sugar.

11. The compound of claim 10, wherein the modified sugar is a 2'-O-methoxyethyl.

12. The compound of claim 5, comprising at least one 2'-O-methoxyethyl nucleoside.

13. The compound of claim 10, wherein the modified sugar is a bicyclic sugar.

14. The compound of claim 13, wherein the bicyclic sugar comprises a 4'-CH(CH$_3$)—O-2' bridge.

15. A composition comprising a compound of claim 1 or a salt thereof and a pharmaceutically acceptable carrier or diluent.

16. A method of reducing alpha-1-antitrypsin in an animal comprising administering to the animal the compound of claim 1, thereby reducing alpha-1-antitrypsin in the animal.

17. A method of treating an alpha-1-antitrypsin deficiency-associated liver disease in an animal comprising administering to the animal the compound of claim 1, thereby treating the alpha-1-antitrypsin deficiency-associated liver disease in the animal.

18. The compound of claim 1, wherein the compound comprises a double-stranded oligonucleotide, wherein one strand of the double-stranded oligonucleotide is the oligonucleotide having a nucleobase sequence comprising at least 12 contiguous nucleobases complementary to an equal portion of the nucleobases 1561 to 1597 of SEQ ID NO: 1.

* * * * *

SEQUENCE LISTING

```
<160> NUMBER OF SEQ ID NOS: 59

<210> SEQ ID NO 1
<211> LENGTH: 3220
<212> TYPE: DNA
<213> ORGANISM: Homo sapien

<400> SEQUENCE: 1
acaatgactc ctttcggtaa gtgcagtgga agctgtacac tgcccaggca aagcgtccgg      60
gcagcgtagg cgggcgactc agatcccagc cagtggactt agccctgtt tgctcctccg     120 ataactgggg tgaccttggt taatattcac cagcagcctc ccccgttgcc cctctggatc     180
cactgcttaa atacggacga ggacagggcc ctgtctcctc agcttcaggc accaccactg     240
acctgggaca gtgaatcgac aatgccgtct tctgtctcgt ggggcatcct cctgctggca     300
ggcctgtgct gcctggtccc tgtctccctg gctgaggatc cccagggaga tgctgcccag     360
aagacagata catcccacca tgatcaggat cacccaacct tcaacaagat cacccccaac     420
ctggctgagt tcgccttcag cctataccgc cagctggcac accagtccaa cagcaccaat     480
atcttcttct ccccagtgag catcgctaca gcctttgcaa tgctctccct ggggaccaag     540
gctgacactc acgatgaaat cctggagggc ctgaatttca acctcacgga gattccggag     600
gctcagatcc atgaaggctt ccaggaactc ctccgtaccc tcaaccagcc agacagccag     660
ctccagctga ccaccggcaa tggcctgttc ctcagcgagg gctgaagct agtggataag     720 tttttggagg atgttaaaaa gttgtaccac tcagaagcct tcactgtcaa cttcggggac     780
accgaagagg ccaagaaaca gatcaacgat tacgtggaga agggtactca agggaaaatt     840
gtggatttgg tcaaggagct tgacagagac acagtttttg ctctggtgaa ttacatcttc     900
tttaaaggca aatgggagag acccttgaa gtcaaggaca ccgaggaaga ggacttccac     960
gtggaccagg tgaccaccgt gaaggtgcct atgatgaagc gtttaggcat gtttaacatc    1020
cagcactgta agaagctgtc cagctgggtg ctgctgatga aatacctggg caatgccacc    1080
gccatcttct tcctgcctga tgaggggaaa ctacagcacc tggaaaatga actcacccac    1140
gatatcatca ccaagttcct ggaaaatgaa gacagaaggt ctgccagctt acatttaccc    1200
aaactgtcca ttactggaac ctatgatctg aagagcgtcc tgggtcaact gggcatcact    1260
aaggtcttca gcaatgggc tgacctctcc gggtcacag aggaggcacc cctgaagctc    1320
tccaaggccg tgcataaggc tgtgctgacc atcgacgaga aagggactga agctgctggg    1380
gccatgtttt tagaggccat acccatgtct atccccccg aggtcaagtt caacaaaccc    1440
```

```
tttgtcttct taatgattga acaaaatacc aagtctcccc tcttcatggg aaaagtggtg    1500
aatcccaccc aaaaataact gcctctcgct cctcaacccc tccctccat ccctggcccc    1560 ctccctggat gacattaaag aagggttgag ctggtccctg cctgcatgtg actgtaaatc    1620
cctcccatgt tttctctgag tctcccttg cctgctgagg ctgtatgtgg gctccaggta    1680
acagtgctgt cttcgggccc cctgaactgt gttcatggag catctggctg ggtaggcaca    1740
tgctgggctt gaatccaggg gggactgaat cctcagctta cggacctggg cccatctgtt    1800
tctggagggc tccagtcttc cttgtcctgt cttggagtcc caagaagga atcacagggg    1860 aggaaccaga taccagccat gaccccaggc tccaccaagc atcttcatgt cccctgctc    1920 atcccccact ccccccacc cagagttgct catcctgcca gggctggctg tgcccacccc    1980
aaggctgccc tcctggggc ccagaactg cctgatcgtg ccgtggccca gttttgtggc    2040
atctgcagca acacaagaga gaggacaatg tcctcctctt gacccgctgt cacctaacca    2100
gactcgggcc ctgcacctct caggcacttc tggaaaatga ctgaggcaga ttcttcctga    2160
agcccattct ccatggggca acaaggacac ctattctgtc cttgtccttc catcgctgcc    2220
ccagaaagcc tcacatatct ccgtttagaa tcaggtccct tctccccaga tgaagaggag    2280
ggtctctgct ttgttttctc tatctcctcc tcagacttga ccaggcccag caggccccag    2340
aagaccatta ccctatatcc cttctcctcc ctagtcacat ggccataggc ctgctgatgg    2400
ctcaggaagg ccattgcaag gactcctcag ctatgggaga ggaagcacat cacccattga    2460
cccccgcaac ccctcccttt cctcctctga gtcccgactg gggccacatg cagcctgact    2520
tctttgtgcc tgttgctgtc cctgcagtct tcagagggcc accgcagctc cagtgccacg    2580
gcaggaggct gttcctgaat agccctgtg gtaaggccca ggagagtcct tccatcctcc    2640
aaggccctgc taaaggacac agcagccagg aagtcccctg ggccctagc tgaaggacag    2700 cctgctccct ccgtctctac caggaatggc cttgtcctat ggaaggcact gccccatccc    2760
aaactaatct aggaatcact gtctaaccac tcactgtcat gaatgtgtac ttaaaggatg    2820
aggttgagtc ataccaaata gtgatttcga tagttcaaaa tggtgaaatt agcaattcta    2880
catgattcag tctaatcaat ggataccgac tgtttcccac acaagtctcc tgttctctta    2940
agcttactca ctgacagcct ttcactctcc acaaatacat taaagatatg gccatcacca    3000 agcccctag gatgacacca gacctgagag tctgaagacc tggatccaag ttctgactt    3060 tccccctgac agctgtgtga ccttcgtgaa gtcgccaaac ctctctgagc cccagtcatt    3120
gctagtaaga cctgcctttg agttggtatg atgttcaagt tagataacaa aatgtttata    3180
cccattagaa cagagaataa atagaactac atttcttgca                           3220
```

<210> SEQ ID NO 2
<211> LENGTH: 20000
<212> TYPE: DNA
<213> ORGANISM: Homo sapien

<400> SEQUENCE: 2

```
tatctaagcc acccacgcag ggcatgtatt tctgaataat aagccctcaa gtcctgctgg      60
gtctcccata gtccccacgc aagggtgagt cttgcacgct cagccctgcc tgtggttccc     120
agaaggcctc tgtcactgcg tgcttgcttt ctctcccagg gaagataccc cagtgccatg     180 tcttgggca agagaaaatg aagacagacc tggaacatga acatggtggc cttgccagaa     240
agcaagtgtg tgttgctgaa acatcagcag agattgtcaa agggataaag agataactta     300
```

-continued

```
aaagggttcc tattgaccaa aatgcgacaa gttgaccatc taaaatcaaa tcataattat    360
agttcaatag gacacattga gtctcttaaa agcttccaat ccgtaatgac catcaaggcc    420
cataacctca aaagagtaaa gttaaaataa agttcagaaa aggttagctg caataaaaca    480
tgagttttag taattttaac aagaagggga tgaagctata gatgcatttt tattccttct    540
tttaactatg ttgccccttta taatgtatag ctttgcctta ttttctctg tctgagtaag    600 gataaagagt aaaggccagg cacagtggct cacacctgta attccagcac tttgggaggc    660
cgaggcgggc agataacttg aggccaggag tttgagacca gcctggccaa catggtgaaa    720
ccctgtcact actaaaaata caaaaattaa ctggaattgg tagcacatgc ctgtaatgcc    780
agctactctg gaggctgagg cacgagaatc gctcgtaatt ccagaattcg agaggtggag    840
tttgcagtaa gccaagattg cgccactgta ctccagcctg ggtgactgag tgagactctg    900
tctcaaaaaa aaaaaaaaaa agaagaagct gtgagtaggc cacatagttc cagaaaatgc    960
agaaatcccc cctcccctcc ccaacacaca ggaagtggct caggagatta cacacagaag   1020
gaaagtgtgt ctgctggggt tttgcaagtt ggctaatttg aaaggtgact ggaggaggtg   1080
aaaaaatggt gcaaacttca ttcattcatt aaatgagtta taagaagaca gacacaagtg   1140
tccattatgc taacagagct ctgtgttaaa caccccacca gcatcgcctc atctaagcct   1200
cagaagagct atgtgggaaa gaaactttta tccctatttt atagatgagg aaaccaaggc   1260
tcagagaact gagggcctcc cccggatcca agtccaccta gctgcagtca ccccacatcc   1320
tctgcatgtc acaggtgctc agaaagatgc tgaaggcacc tggcccttca ccttcggaaa   1380
gccaaaatga gcacggcccc taagaggggg attgacagcc ttttctggaa aaaatggaag   1440
tttgaatctg aggaggtgtc cctcaacaac aggtgctgct ccccaaatct ggggccaaac   1500
gcagcagttg ttcccccact tagaccctg agacccatct atatggtttt tcagagccag   1560
gacacatccc caaaggtcat ggcctttggt ggttagcatt gacttggggc ccatcacatg   1620
ccagaggctg cccgaagtgc ttaaatgtta ttatctcatt cgatcttcac agtcctgatg   1680
gaagtgactc ttcttagagt cttcctatct cacagatgag gaaaccgagg cacagagagg   1740
ttaagtggct tgtctaagag ctcacaaaaa gagcgatgga gctaaggctt ggccccagat   1800
attagatccc gaacccacgc cttaaccagt gacctgcact gactctcaaa gaaggaagct   1860
ggtgcctggg aaggagggtg catagtgagg gtgtgcatgg ggtgtgtgtg tttgtggggt   1920
ggccagcact ctccgggggc actttgccaa tgagttcagc tcccatgaag tccactgttg   1980
ttctcctgac cagccactca gtcttgattt acttggccca gggccactgg cacacctcac   2040 cccccttaccc gattccttgc tgcagacccc aaatctcgac tctcacatcc ctatccagcc   2100
cataccacga ggctcccatc tccaggcagg gccctgtggt ggggcagggc ctcccccaga   2160
tgccccttac tcatgaccag ctcacaggat cttcccatga tgcatttcct ctgggggat   2220 cagcccagat gctgcaatag acaattgtgg aagtaaccag gtggacaaga ctttccccct   2280
catgtcctgg ggttcctggg ggcacagtat ccttgtgaat ggccactgag tactcccacc   2340
cctcccacca caaccccccgg gattttgtcc tggtgcgttt ttccagatta tcctagccct   2400
tcctcccagg atggatgtcc agagcagggc ggggcctgag cctagagccc tgccaaaaga   2460
gcaggacccc aaattctgag ccccttactt gcctcacctg ctcccaccca tgctttcttc   2520
attcctcctc caaaagcccc agctccccac tgcaatccct tctgcaccca gccaggtcct   2580
atgacacaca cctcccccagt gcacacagac ctgcccaact gtgggctgc ccactgggca   2640 tttcataggt ggctcagtcc tcttccctct gcagctggcc ccagaaacct gccagttatt   2700
```

```
ggtgccaggt ctgtgccagg agggcgaggc ctgtcatttc tagtaatcct ctgggcagtg    2760
tgactgtacc tcttgcggca actcaaaggg agagggtgac ttgtcccggg tcacagagct    2820
gaaagggcag gtacaacagg tgacatgccg ggctgtctga gtttatgagg gcccagtctt    2880
gtgtctgccg ggcaatgagc aaggctcctt cctgtccaag ctccccgccc ctccccagcc    2940
tactgcctcc acccgaagtc tacttcctgg gtgggcagga actgggcact gtgcccaggg    3000
catgcactgc ctccacgcag caaccctcag agtcctgagc tgaaccaaga aggaggaggg    3060
ggtcgggcct ccgaggaagg cctagccgct gctgctgcca ggaattccag gttggagggg    3120
cggcaacctc ctgccagcct tcaggccact ctcctgtgcc tgccagaaga cagagagctt    3180
gaggagagct tgaggagagc aggaaaggtg ggacattgct gctgctgctc actcagttcc    3240
acaggtggga gggacagcag ggcttagagt gggggtcatt gtgcagatgg gaaaacaaag    3300
gcccagagag gggaagaaat gcccaggagc taccgagggc aggcgacctc aaccacagcc    3360
cagtgctgga gctgtgagtg gatgtagagc agcggaatat ccattcagcc agctcagggg    3420
aaggacaggg gccctgaagc caggggatgg agctgcaggg aagggagctc agagagaagg    3480
ggaggggagt ctgagctcag tttcccgctg cctgaaagga gggtggtacc tactcccttc    3540
acagggtaac tgaatgagag actgcctgga ggaaagctct tcaagtgtgg cccacccac     3600 cccagtgaca ccagccctg acacggggga ggagggcag catcaggagg ggctttctgg    3660
gcacacccag tacccgtctc tgagctttcc ttgaactgtt gcatttaat cctcacagca    3720 gctcaacaag gtacataccg tcaccatccc cattttacag atagggaaat tgaggctcgg    3780
agcggttaaa caactcacct gaggcctcac agccagtaag tgggttccct ggtctgaatg    3840
tgtgtgctgg aggatcctgt gggtcactcg cctggtagag ccccaaggtg gaggcataaa    3900
tgggactggt gaatgacaga aggggcaaaa atgcactcat ccattcactc tgcaagtatc    3960
tacggcacgt acgccagctc ccaagcaggt ttgcgggttg cacagcgggc gatgcaatct    4020
gatttaggct tttaaaggga ttgcaatcaa gtggggcccc actagcctca accctgtacc    4080
tcccctcccc tccacccca gcagtctcca aaggcctcca acaacccag agtgggggcc     4140 atgtatccaa agaaactcca agctgtatac ggatcacact ggttttccag gagcaaaaac    4200
agaaacaggc ctgaggctgg tcaaaattga acctcctcct gctctgagca gcctgggggg    4260
cagactaagc agagggctgt gcagacccac ataaagagcc tactgtgtgc caggcacttc    4320
acccgaggca cttcacaagc atgcttggga atgaaacttc caactctttg ggatgcaggt    4380
gaaacagttc ctggttcaga gaggtgaagc ggcctgcctg aggcagcaca gctcttcttt    4440
acagatgtgc ttccccacct ctaccctgtc tcacggcccc ccatgccagc ctgacggttg    4500
tgtctgcctc agtcatgctc catttttcca tcgggaccat caagagggtg tttgtgtcta    4560
aggctgactg ggtaactttg gatgagcggt ctctccgctc tgagcctgtt tcctcatctg    4620
tcaaatgggc tctaacccac tctgatctcc caggcggca gtaagtcttc agcatcaggc     4680
attttggggt gactcagtaa atggtagatc ttgctaccag tggaacagcc actaaggatt    4740
ctgcagtgag agcagagggc cagctaagtg gtactctccc agagactgtc tgactcacgc    4800 cacccctcc accttggaca caggacgctg tggtttctga gccaggtaca atgactcctt    4860
tcggtaagtg cagtggaagc tgtacactgc ccaggcaaag cgtccgggca gcgtaggcgg    4920
gcgactcaga tccagccag tggacttagc ccctgtttgc cctccgata actgggtga     4980 ccttggttaa tattcaccag cagcctcccc cgttgcccct ctggatccac tgcttaaata    5040
```

```
cggacgagga cagggccctg tctcctcagc ttcaggcacc accactgacc tgggacagtg    5100
aatcgtaagt atgcctttca ctgcgagagg ttctggagag gcttctgagc tccccatggc    5160
ccaggcaggc agcaggtctg ggcaggagg ggggttgtgg agtgggtatc cgcctgctga    5220
ggtgcagggc agatggagag gctgcagctg agctcctatt ttcataataa cagcagccat    5280
gagggttgtg tcctgtttcc cagtcctgcc cggtccccc tcggtacctc ctggtggata    5340
cactggttcc tgtaagcaga agtggatgag ggtgtctagg tctgcagtcc tggcacccca    5400
ggatggggga caccagccaa gatacagcaa cagcaacaaa gcgcagccat ttctttctgt    5460
ttgcacagct cctctgtctg tcggggctc ctgtctgttg tctcctataa gcctcaccac    5520
ctctcctact gcttgggcat gcatctttct ccccttctat agatgaggag gttaaggtcc    5580 agagagggt ggggaggaac gccggctcac attctccatc ccctccagat atgaccagga    5640
acagacctgt gccaggcctc agccttacat caaaatgggc ctccccatgc accgtggacc    5700
tctgggccct cctgtcccag tggaggacag gaagctgtga ggggcactgt cacccagggc    5760
tcaagctggc attcctgaat aatcgctctg caccaggcca cggctaagct cagtgcgtga    5820
ttaagcctca taaccctcca aggcagttac tagtgtgatt cccattttac agatgaggaa    5880
gatggggaca gagaggtgaa taactggccc caaatcacac accatccata attcgggctc    5940
aggcacctgg ctccagtccc caaactcttg aacctggccc tagtgtcact gtttctcttg    6000
ggtctcaggc gctggatggg gaacaggaaa cctgggctgg acttgaggcc tctctgatgc    6060
tcggtgactt cagacagttg ctcaacctct ctgttctctt gggcaaaaca tgataacctt    6120
tgacttctgt cccctcccct caccccaccc gaccttgatc tctgaagtgt tggaaggatt    6180 taattttcc tgcactgagt tttggagaca ggtcaaaaag atgaccaagg ccaaggtggc    6240
cagtttccta tagaacgcct ctaaaagacc tgcagcaata gcagcaagaa ctggtattct    6300
cgagaacttg ctgcgcagca ggcacttctt ggcatttat gtgtatttaa tttcacaata    6360
gctctatgac aaagtccacc tttctcatct ccaggaaact gaggttcaga gaggttaagt    6420
aacttgtcca aggtcacaca gctaatagca agttgacgtg gagcaatctg gcctcagagc    6480
ctttaatttt agccacagac tgatgctccc ctcttcattt agccaggctg cctctgaagt    6540
tttctgattc aagacttctg gcttcagctt tgtacacaga gatgattcaa tgtcaggttt    6600
tggagtgaaa tctgtttaat cccagacaaa acatttagga ttacatctca gttttgtaag    6660
caagtagctc tgtgattttt agtgagttat ttaatgctct ttggggctca attttctat    6720 ctataaaata gggctaataa tttgcacctt ataggggtaag ctttgaggac agattagatg    6780
atacggtgcc tgtaaaacac caggtgttag taagtgtggc aatgatggtg acgctgaggc    6840
tgatgtttgc ttagcatagg gttaggcagc tggcaggcag taaacagttg gataatttaa    6900
tggaaaattt gccaaactca gatgctgttc actgctgagc aggagcccct tcctgctgaa    6960
atggtcctgg ggagtgcagc aggctctccg ggaagaaatc taccatctct cgggcaggag    7020
ctcaacctgt gtgcaggtac agggagggct tcctcacctg gtgcccactc atgcattacg    7080
tcagttattc ctcatccctg tccaaaggat tctttttctcc attgtacagc tatgaagcta    7140
gtgctcaaag aagtgaagtc atttacccca ggcccctgc cagtaagtga cagggcctgg    7200
tcacacttgg gtttatttat tgcccagttc aacaggttgt ttgaccatag gcgagattct    7260
cttccctgca ccctgccggg ttgctcttgg tcccttattt tatgctcccg ggtagaaatg    7320
gtgtgagatt aggcagggag tggctcgctt ccctgtccct ggccccgcaa agagtgctcc    7380
cacctgcccc gatcccagaa atgtcaccat gaagccttca ttcttttggt ttaaagcttg    7440
```

```
gcctcagtgt ccgtacacca tggggtactt ggccagatgg cgactttctc ctctccagtc    7500
gccctcccag gcactagctt ttaggagtgc agggtgctgc ctctgataga agggccagga    7560
gagagcaggt tttggagtcc tgatgttata aggaacagct tgggaggcat aatgaaccca    7620
acatgatgct tgagaccaat gtcacagccc aattctgaca ttcatcatct gagatctgag    7680
gacacagctg tctcagttca tgatctgagt gctgggaaag ccaagacttg ttccagcttt    7740
gtcactgact tgctgtatag cctcaacaag gccctgaccc tctctgggct tcaaactctt    7800
cactgtgaaa ggaggaaacc agagtaggtg atgtgacacc aggaaagatg gatgggtgtg    7860
ggggaatgtg ctcctcccag ctgtcacccc ctcgccaccc tccctgcacc agcctctcca    7920
cctcctttga gcccagaatt cccctgtcta ggagggcacc tgtctcatgc ctagccatgg    7980
gaattctcca tctgttttgc tacattgaac ccagatgcca ttctaaccaa gaatcctggc    8040
tgggtgcagg ggctctcgcc tgtaacccca gcactttggg aggccaaggc aggcggatca    8100
agaggtcagg agttcaagac ctgcctggcc aacacggtga aacctcagct ctactaaaaa    8160
tacaaaaatt agccaggcgt ggtggcacac gcctgtaatc ccagctattt gggaagctga    8220
gacagaagaa tttcttgaac ccgggaggtg gaggtttcag tgagccgaga tcacgccact    8280
gcactccacc ctggcagata aagcgagact ctgtctcaaa aaaaacccaa aaacctatgt    8340
tagtgtacag agggccccag tgaagtcttc tcccagcccc actttgcaca actggggaga    8400
gtgaggcccc aggaccagag gattcttgct aaaggccaag tggatagtga tggccctgcc    8460
agggctagaa gccacaacct ctggccctga ggccactcag catatttagt gtccccaccc    8520
tgcagaggcc caactccctc ctgaccactg agccctgtaa tgatggggga atttccataa    8580
gccatgaagg actgcacaaa gttcagttgg gaagtgaaag agaaattaaa gggagatgga    8640
aatatacagc actaatttta gcaccgtctt tagttctaac aacactagct agctgaagaa    8700
aaatacaaac atgtattatg taatgtgtgg tctgttccat ttggattact tagaggcacg    8760
agggccagga gaaaggtggt ggagagaaac cagctttgca cttcatttgt tgctttattg    8820
gaaggaaact tttaaaagtc caaggggggtt gaagaatctc aatatttgtt atttccagct    8880
ttttttctcc agttttcat ttcccaaatt caaggacacc ttttttcttttg tattttgtta    8940 agatgatggt tttggttttg tgactagtag ttaacaatgt ggctgccggg catattctcc    9000
tcagctagga cctcagtttt tccatctgtg aagacggcag gttctaccta gggggctgca    9060
ggctggtggt ccgaagcctg ggcatatctg gagtagaagg atcactgtgg ggcagggcag    9120
gttctgtgtt gctgtggatg acgttgactt tgaccattgc tcggcagagc ctgctctcgc    9180
tggttcagcc acaggcccca ccactcccta ttgtctcagc cccgggtatg aaacatgtat    9240
tcctcactgg cctatcacct gaagcctttg aatttgcaac acctgccaac ccctccctca    9300
aaagagttgc cctctcagat ccttttgatg taaggtttgg tgttgagact tatttcacta    9360
aattctcata cataaacatc actttatgta tgaggcaaaa tgaggaccag ggagatgaat    9420
gacttgtcct ggctcataca cctggaaagt gacagagtca gattagatcc caggtctatc    9480
tgaagttaaa agaggtgtct tttcacttcc cacctcctcc atctactta aagcagcaca    9540 aaccccctgct ttcaaggaga gatgagcgtc tctaaagccc ctgacagcaa gagcccagaa    9600
ctgggacacc attagtgacc cagacggcag gtaagctgac tgcaggagca tcagcctatt    9660
cttgtgtctg ggaccacaga gcattgtggg gacagcccg tctcttggga aaaaaccct    9720 aagggctgag gatccttgtg agtgttgggt gggaacagct cccaggaggt ttaatcacag    9780
```

```
cccctccatg ctctctagct gttgccattg tgcaagatgc atttcccttc tgtgcagcag    9840
tttccctggc cactaaatag tgggattaga tagaagccct ccaagggctt ccagcttgac    9900
atgattcttg attctgatct ggcccgattc ctggataatc gtgggcaggc ccattcctct    9960
tcttgtgcct cattttcttc ttttgtaaaa caatggctgt accatttgca tcttagggtc   10020
attgcagatg taagtgttgc tgtccagagc ctgggtgcag gacctagatg taggattctg   10080
gttctgctac ttcctcagtg acattgaata gctgacctaa tctctctggc tttggtttct   10140
tcatctgtaa aagaaggata ttagcattag cacctcacgg gattgttaca agaaagcaat   10200
gaattaacac atgtgagcac ggagaacagt gcttggcata tggtaagcac tacgtacatt   10260
ttgctattct tctgattctt tcagtgttac tgatgtcggc aagtacttgg cacaggctgg   10320
tttaataatc cctaggcact ccacgtggt gtcaatccct gatcactggg agtcatcatg    10380
tgccttgact cggggcctgg ccccccatc tctgtcttgc aggacaatgc cgtcttctgt    10440 ctcgtgggc atcctcctgc tggcaggcct gtgctgcctg gtccctgtct ccctggctga   10500 ggatcccag ggagatgctg cccagaagac agatacatcc caccatgatc aggatcaccc   10560
aaccttcaac aagatcaccc caacctggc tgagttcgcc ttcagcctat accgccagct    10620
ggcacaccag tccaacagca ccaatatctt cttctcccca gtgagcatcg ctacagcctt   10680
tgcaatgctc tccctgggga ccaaggctga cactcacgat gaaatcctgg agggcctgaa   10740
tttcaacctc acggagattc cggaggctca gatccatgaa ggcttccagg aactcctccg   10800
taccctcaac cagccagaca gccagctcca gctgaccacc ggcaatggcc tgttcctcag   10860
cgagggcctg aagctagtgg ataagttttt ggaggatgtt aaaaagttgt accactcaga   10920
agccttcact gtcaacttcg ggacaccga agaggccaag aaacagatca acgattacgt    10980
ggagaagggt actcaaggga aaattgtgga tttggtcaag gagcttgaca gagacacagt   11040
ttttgctctg gtgaattaca tcttctttaa aggtaaggtt gctcaaccag cctgagctgt   11100
tcccatagaa acaagcaaaa atattctcaa accatcagtt cttgaactct ccttggcaat   11160
gcattatggg ccatagcaat gcttttcagc gtggattctt cagttttcta cacacaaaca   11220
ctaaaatgtt ttccatcatt gagtaatttg aggaaataat agattaaact gtcaaaacta   11280
ctgacagctc tgcagaactt ttcagagcct ttaatgtcct tgtgtatact gtatatgtag   11340
aatatataat gcttagaact atagaacaaa ttgtaataca ctgcataaag ggatagtttc   11400
atggaacata ctttacacga ctctagtgtc ccagaatcag tatcagtttt gcaatctgaa   11460
agacctgggt tcaaatcctg cctctaacac aattagcttt tgacaaaaac aatgcattct   11520
acctctttga ggtgctaatt tctcatctta gcatggacaa ataccattc ttgctgtcag    11580 gttttttag gattaaacaa atgacaaaga ctgtggggat ggtgtgtggc atacagcagg    11640
tgatggactc ttctgtatct caggctgcct tcctgcccct gaggggttaa aatgccaggg   11700
tcctgggggc cccagggcat tctaagccag ctcccactgt cccaggaaaa cagcataggg   11760
gaggggaggt gggaggcaag gccagggct gcttcctcca ctctgaggct cccttgctct    11820
tgaggcaaag gagggcagtg gagagcagcc aggctgcagt cagcacagct aaagtcctgg   11880
ctctgctgtg gccttagtgg gggcccaggt ccctctccag ccccagtctc ctccttctgt   11940
ccaatgagaa agctgggatc aggggtccct gaggcccctg tccactctgc atgcctcgat   12000
ggtgaagctc tgttggtatg gcagagggga ggctgctcag gcatctgcat ttcccctgcc   12060
aatctagagg atgaggaaag ctctcaggaa tagtaagcag aatgtttgcc ctggatgaat   12120
aactgagctg ccaattaaca aggggcaggg agccttagac agaaggtacc aaatatgcct   12180
```

```
gatgctccaa catttattt gtaatatcca agacaccctc aaataaacat atgattccaa    12240
taaaaatgca cagccacgat ggcatctctt agcctgacat cgccacgatg tagaaattct    12300
gcatcttcct ctagttttga attatcccca cacaatcttt ttcggcagct tggatggtca    12360
gtttcagcac cttttacaga tgatgaagct gagcctcgag ggatgtgtgt cgtcaagggg    12420
gctcagggct tctcaggag gggactcatg gtttctttat tctgctacac tcttccaaac    12480
cttcactcac ccctggtgat gcccaccttc ccctctctcc aggcaaatgg gagagaccct    12540
ttgaagtcaa ggacaccgag gaagaggact tccacgtgga ccaggtgacc accgtgaagg    12600
tgcctatgat gaagcgttta ggcatgttta acatccagca ctgtaagaag ctgtccagct    12660
gggtgctgct gatgaaatac ctgggcaatg ccaccgccat cttcttcctg cctgatgagg    12720
ggaaactaca gcacctggaa aatgaactca cccacgatat catcaccaag ttcctggaaa    12780
atgaagacag aaggtgattc cccaacctga gggtgaccaa gaagctgccc acacctctta    12840
gccatgttgg gactgaggcc catcaggact ggccagaggg ctgaggaggg tgaaccccac    12900
atccctgggt cactgctact ctgtataaac ttggcttcca gaatgaggcc accactgagt    12960
tcaggcagcg ccatccatgc tccatgagga ggacagtacc caggggtgag gaggtaaagg    13020
tctcgtccct ggggacttcc cactccagtg tggacactgt cccttcccaa tatccagtgc    13080
ccagggcagg gacagcagca ccaccacacg ttctggcaga accaaaaagg aacagatggg    13140
cttcctggca aaggcagcag tggagtgtgg agttcaaggg tagaatgtcc ctgggggac     13200 gggggaagag cctgtgtggc aaggcccaga aaagcaaggt tcggaattgg aacagccagg    13260
ccatgttcgc agaaggcttg cgtttctctg tcactttatc ggtgctgtta gattgggtgt    13320
cctgtagtaa gtgatactta aacatgagcc acacattagt gtatgtgtgt gcattcgtga    13380
ttatgcccat gccctgctga tctagttcgt tttgtacact gtaaaaccaa gatgaaaata    13440
caaaaggtgt cgggttcata ataggaatcg aggctggaat ttctctgttc catgccagca    13500
cctcctgagg tctctgctcc aggggttgag aaagaacaaa gaggctgaga gggtaacgga    13560
tcagagagcc cagagccaag ctgcccgctc acaccagacc ctgctcaggg tggcattgtc    13620
tccccatgga aaaccagaga ggagcactca gcctggtgtg gtcactcttc tcttatccac    13680
taaacggttg tcactgggca ctgccaccag ccccgtgttt ctctgggtgt agggccctgg    13740
ggatgttaca ggctgggggc caggtgaccc aacactacag ggcaagatga gacaggcttc    13800
caggacacct agaatatcag aggaggtggc atttcaagct tttgtgattc attcgatgtt    13860
aacattcttt gactcaatgt agaagagcta aagtagaac aaaccaaagc cgagttccca    13920
tcttagtgtg ggtggaggac acaggagtaa gtggcagaaa taatcagaaa agaaaacact    13980
tgcactgtgt tgggtcccag aagaacaaga ggaatgctgt gccatgcctt gaatttcttt    14040
tctgcacgac aggtctgcca gcttacattt acccaaactg tccattactg gaacctatga    14100
tctgaagagc gtcctgggtc aactgggcat cactaaggtc ttcagcaatg gggctgacct    14160
ctccggggtc acagaggagg caccccctgaa gctctccaag gtgagatcac cctgacgacc    14220
ttgttgcacc ctggtatctg tagggaagaa tgtgtggggg ctgcagctct gtcctgaggc    14280
tgaggaaggg gccgagggaa acaaatgaag acccaggctg agctcctgaa gatgcccgtg    14340
attcactgac acgggacgtg gtcaaacagc aaagccaggc aggggactgc tgtgcagctg    14400
gcactttcgg ggcctcccttt gaggttgtgt cactgacccct gaatttcaac tttgcccaag    14460
accttctaga cattgggcct tgatttatcc atactgacac agaaaggttt gggctaagtt    14520
```

```
gtttcaaagg aatttctgac tccttcgatc tgtgagattt ggtgtctgaa ttaatgaatg   14580
atttcagcta aagatgacac ttattttgga aaactaaagg cgaccaatga acaactgcag   14640
ttccatgaat ggctgcatta tcttggggtc tgggcactgt gaaggtcact gccagggtcc   14700
gtgtcctcaa ggagcttcaa gccgtgtact agaaaggaga gagccctgga ggcagacgtg   14760
gagtgacgat gctcttccct gttctgagtt gtgggtgcac ctgagcaggg ggagaggcgc   14820
ttgtcaggaa gatggacaga ggggagccag ccccatcagc caaagccttg aggaggagca   14880
aggcctatgt gacagggagg gagaggatgt gcagggccag ggccgtccag ggggagtgag   14940
cgcttcctgg gaggtgtcca cgtgagcctt gctcgaggcc tgggatcagc cttacaacgt   15000
gtctctgctt ctctcccctc caggccgtgc ataaggctgt gctgaccatc gacgagaaag   15060
ggactgaagc tgctggggcc atgtttttag aggccatacc catgtctatc cccccgagg    15120
tcaagttcaa caaaccctt gtcttcttaa tgattgaaca aaataccaag tctcccctct    15180
tcatgggaaa agtggtgaat cccacccaaa ataactgcc tctcgctcct caacccctcc    15240
cctccatccc tggcccccctc cctggatgac attaaagaag ggttgagctg gtccctgcct   15300
gcatgtgact gtaaatccct cccatgtttt ctctgagtct cccttttgcct gctgaggctg   15360
tatgtgggct ccaggtaaca gtgctgtctt cgggcccct gaactgtgtt catggagcat    15420
ctggctgggt aggcacatgc tgggcttgaa tccaggggg actgaatcct cagcttacgg    15480
acctgggccc atctgtttct ggagggctcc agtcttcctt gtcctgtctt ggagtcccca   15540
agaaggaatc acaggggagg aaccagatac cagccatgac cccaggctcc accaagcatc   15600
ttcatgtccc cctgctcatc ccccactccc cccacccag agttgctcat cctgccaggg    15660
ctggctgtgc ccaccccaag gctgccctcc tgggggcccc agaactgcct gatcgtgccg   15720
tggcccagtt ttgtggcatc tgcagcaaca caagagagag gacaatgtcc tcctcttgac   15780
ccgctgtcac ctaaccagac tcgggccctg cacctctcag gcacttctgg aaaatgactg   15840
aggcagattc ttcctgaagc ccattctcca tggggcaaca aggacaccta ttctgtcctt   15900
gtccttccat cgctgcccca gaaagcctca catatctccg tttagaatca ggtcccttct   15960
ccccagatga agaggagggt ctctgctttg ttttctctat ctcctcctca gacttgacca   16020
ggcccagcag gccccagaag accattaccc tatatccctt ctcctcccta gtcacatggc   16080
cataggcctg ctgatggctc aggaaggcca ttgcaaggac tcctcagcta tgggagagga   16140
agcacatcac ccattgaccc ccgcaacccc tcccttttcct cctctgagtc ccgactgggg   16200
ccacatgcag cctgacttct ttgtgcctgt tgctgtccct gcagtcttca gagggccacc   16260
gcagctccag tgccacggca ggaggctgtt cctgaatagc ccctgtggta agggccagga   16320
gagtccttcc atcctccaag gccctgctaa aggacacagc agccaggaag tcccctgggc   16380
ccctagctga aggacagcct gctccctccg tctctaccag gaatggcctt gtcctatgga   16440
aggcactgcc ccatcccaaa ctaatctagg aatcactgtc taaccactca ctgtcatgaa   16500
tgtgtactta aaggatgagg ttgagtcata ccaaatagtg atttcgatag ttcaaaatgg   16560
tgaaattagc aattctacat gattcagtct aatcaatgga taccgactgt ttcccacaca   16620
agtctccctgt tctcttaagc ttactcactg acagcctttc actctccaca aatacattaa   16680
agatatggcc atcaccaagc ccctaggat gacaccagac ctgagagtct gaagacctgg    16740
atccaagttc tgacttttcc ccctgacagc tgtgtgacct tcgtgaagtc gccaaacctc   16800
tctgagcccc agtcattgct agtaagacct gcctttgagt tggtatgatg ttcaagttag   16860
ataacaaaat gtttataccc attagaacag agaataaata gaactacatt tcttgcactt   16920
```

```
atgagctttc tgtgaatcag acatccctat gaagtacctc ccctggctgt ttctcattta   16980
ctcactgtag cagcactgcg atgtgtgagt atatctgctg tgctcttaaa ctccaaatct   17040
gaggaaactg aggctcagag aggctactgg tctcccacaa tgtcacacag ctcataagtg   17100
gcaaagctgg cttgatgggc tacttgttcc tctgaaccat accacctcac cacactctcc   17160
ccttcgaggg tcacgctaaa cttctgcaga ggtaattcct ccttaaacca gaagggttgc   17220
tggtggccca cagctcacgc ctagcacact tcatgagaaa acaccctgt gcccagtgtg    17280
gagcaggcat tgagctgaag gtggtgagca gaagctcatc caccagatgt tgacacagcc   17340
cgcagccttg ggcgacccac aggactcctc ttatttaact ggcatttggt aggagaacag   17400
gggcagagtc aaagacaagt tggctttctg gagagcccag ggcagggaag gaggtggcag   17460
cgctgagggc ggtcaccta gacaccatcg ttttactttg aagaattgtc tgtcacacac    17520
gagttgacag tcaggatggg agagacccca ttcaaactag cataacctcc cagagggaat   17580
tcctgggctc ccctgggaat caacagggat cagtcaagga tgggcagagt gtcatgacaa   17640
cctcattatg aggaagacaa atatatgtca caagtccgtg atgggacaac cataagacct   17700
cagcttcact gtatcttcca gagttttaaa aaaatgtatt cactgtccaa cgtgatcctc   17760
cagacaggtt ctgcaggacg cagcctagga ctcattatcc ccaaagtaca catggggaaa   17820
ctcaggccca gcaggtcaaa tgctctgtcc agtgtgggcc tggaaggcag gtcttctcca   17880
ctgttaggcc tggctgtccc caacagcaca tacttcctca gtccatatgg gatcacgata   17940
aacaactcca tcctccagga ccacactgca tcaacctgct gtgccctaac atcagctgaa   18000
ggccaagctg cggggcaccc tgggtgttcc aagtcacttt ccctctgcag gcaggaacct   18060
catcctgctc tgaaacagat gagagggaaa cgcagaaaac agcttccagc tcagccagga   18120
accttagagt cctgaccttt tacctcgcct aggagtttgc aggggagaga acacacgaat   18180
ttcggatttt aagcctaaat aaaggaagcc ttagtttgaa gtgcaagctc tgccggacag   18240
ggggcaccct gtgagcccca tttgttaaga ggacaatagt cagagagctt ccaggctctc   18300
acaccagaaa caggaaatac agatttcaca ctgatctcct tcccaggagc aacttgatcc   18360
tctccataaa tccgagcggg aagcatttat ccaaacaaca aacaagcaaa catgagctgt   18420
gtatggggga tagagagaat gaaacccagg tccatcccgg ggagaatgct ggtctatggc   18480
agtggggagc agtgaataaa tgaggcgtac atccatggat ctgggtggag agggtcaggg   18540
tgtaacccag gacctttcca gaggcatgag aaacagtcag cctacaccca cagatgacct   18600
caaacacccc aagtgctcct tgaaaggctg aggcttttgt gttgctcttg gttggattat   18660
tcacaggcaa tgaagtaaac aaggcacacc acaggactca gaaccaggga cagcttccgc   18720
aggaacctgg gtcagttcta aaaggacaaa tggaatgacc ctgagtagag aagtcagaga   18780
aaggcactct cactgaggca aactccctcc ccagcaggga cccaggcagc aactcggaaa   18840
agcaggagtg tcactattgt atcatatggg agagggcagg ctgtgtgctc tcagggaagt   18900
tcctcaactt ctctgtgccg tagtttcctc atctgcaaaa tgtaaatcaa atttgaggtt   18960
tcaatgcaat gacttatttc tctaaagttc cttgtccttg tcccatgtag cccagaaatc   19020
ttcctctggc ctagttgtgg agcctggcct aagtcgcaca ttgctggaga tggtgaagct   19080
gaccagcatg agaggtcagt ttctagaagc ccaaatccca acaggcataa gcctcaccct   19140
ccaatatcag ctctatcaga aacaaacaaa caaaaacatg tcttattcat ttgtcctttt   19200
cctcaaatgg gtggcacttg ggcagggcag aagggctggt tatccaagct tggaagatgc   19260
```

```
tgacagcaga cgcttcaatg gcagtaggag tttttctgatc actgtcattg gtatcacgct    19320
tactgttgaa atcgtgacat caggaatgat gaaaggaact agagtcagat ggtctggagc    19380
ggggaagtga ggagctgaaa cctccttcag tctggttgct gtgtcccag ggtgggtaga     19440
tcccctctgt tcatcccaca tgggacaagt agagcgggag aggaatcaac cctttctaaa    19500
gggttgaagc attgagctgt gagcttctcg gttgctgcag cacaatcctt gcccatcctg    19560
actgaaacaa ccagaattca tgaaatgcat caaagaagtc ttcacctact acgcaagcct    19620
ggaagggtga ctaagatctg aaaaacaccg ggaaggctaa aggaactccc acaaggaaac    19680
cccattagaa agttctagtt acaagatgct cagcacaggc catgcagaaa tacgcccaga    19740
tccggtggtg agcaaggaac ggtaggaatg tgagcactga gtcacgcagg agagactcat    19800
aggggctcaa gccagcaagg ggacggcctc caccccacgc actgttggcc aacagcttcc    19860
aggggcattt gctctcagaa gtcaaagctg attttccaca attgaagtgc tcactgtttg    19920
ggatgattta ggaacaacac caacaaaaag gaatgaacaa tcagagctaa tagaattgtg    19980
tttaaactct gctgggcttc                                                 20000

<210> SEQ ID NO 3
<211> LENGTH: 52
<212> TYPE: DNA
<213> ORGANISM: Homo sapien

<400> SEQUENCE: 3
tgcataaggc tgtgctgacc atcgacaaga aagggactga agctgctggg gc              52

<210> SEQ ID NO 4
<211> LENGTH: 3199
<212> TYPE: DNA
<213> ORGANISM: Homo sapien

<400> SEQUENCE: 4
tgggcaggaa ctgggcactg tgcccagggc atgcactgcc tccacgcagc aaccctcaga      60
gtcctgagct gaaccaagaa ggaggagggg gtcgggcctc cgaggaaggc ctagccgctg     120
ctgctgccag gaattccagg ttggaggggc ggcaacctcc tgccagcctt caggccactc     180
tcctgtgcct gccagaagag acagagcttg aggagagctt gaggagagca ggaaaggaca     240
atgccgtctt ctgtctcgtg gggcatcctc ctgctggcag gcctgtgctg cctggtccct     300
gtctccctgg ctgaggatcc ccagggagat gctgcccaga agacagatac atcccaccat     360
gatcaggatc acccaacctt caacaagatc accccccaacc tggctgagtt cgccttcagc     420
ctataccgcc agctggcaca ccagtccaac agcaccaata tcttcttctc cccagtgagc     480
atcgctacag ccttttgcaat gctctccctg gggaccaagg ctgacactca cgatgaaatc     540
ctggagggcc tgaatttcaa cctcacggag attccggagg ctcagatcca tgaaggcttc     600
caggaactcc tccgtaccct caaccagcca gacagccagc tccagctgac caccggcaat     660
ggcctgttcc tcagcgaggg cctgaagcta gtggataagt ttttggagga tgttaaaaag     720
ttgtaccact cagaagcctt cactgtcaac ttcggggaca ccgaagaggc caagaaacag     780
atcaacgatt acgtggagaa gggtactcaa gggaaaattg tggatttggt caaggagctt     840
gacagagaca cagttttttgc tctggtgaat tacatcttct ttaaaggcaa atgggagaga     900
ccctttgaag tcaaggacac cgaggaagag gacttccacg tggaccaggt gaccaccgtg     960
aaggtgccta tgatgaagcg tttaggcatg tttaacatcc agcactgtaa gaagctgtcc    1020
agctgggtgc tgctgatgaa atacctgggc aatgccaccg ccatcttctt cctgcctgat    1080
```

-continued

```
gagggggaaac tacagcacct ggaaaatgaa ctcacccacg atatcatcac caagttcctg    1140
gaaaatgaag acagaaggtc tgccagctta catttaccca aactgtccat tactggaacc    1200
tatgatctga agagcgtcct gggtcaactg ggcatcacta aggtcttcag caatggggct    1260
gacctctccg gggtcacaga ggaggcaccc ctgaagctct ccaaggccgt gcataaggct    1320
gtgctgacca tcgacgagaa agggactgaa gctgctgggg ccatgttttt agaggccata    1380
cccatgtcta tcccccccga ggtcaagttc aacaaaccct tgtcttctt aatgattgaa     1440 caaaatacca agtctcccct cttcatggga aaagtggtga atcccaccca aaaataactg    1500
cctctcgctc ctcaacccct cccctccatc cctggccccc tccctggatg acattaaaga    1560
agggttgagc tggtccctgc ctgcatgtga ctgtaaatcc ctcccatgtt ttctctgagt    1620
ctccctttgc ctgctgaggc tgtatgtggg ctccaggtaa cagtgctgtc ttcgggcccc    1680
ctgaactgtg ttcatggagc atctggctgg gtaggcacat gctgggcttg aatccagggg    1740
ggactgaatc ctcagcttac ggacctgggc ccatctgttt ctggagggct ccagtcttcc    1800
ttgtcctgtc ttggagtccc caagaaggaa tcacagggga ggaaccagat accagccatg    1860
accccaggct ccaccaagca tcttcatgtc ccctgctca tccccactc ccccccaccc      1920 agagttgctc atcctgccag ggctggctgt gcccacccca aggctgccct cctggggcc     1980 ccagaactgc ctgatcgtgc cgtggcccag ttttgtggca tctgcagcaa cacaagagag    2040
aggacaatgt cctcctcttg acccgctgtc acctaaccag actcgggccc tgcacctctc    2100
aggcacttct ggaaaatgac tgaggcagat tcttcctgaa gcccattctc catggggcaa    2160
caaggacacc tattctgtcc ttgtccttcc atcgctgccc cagaaagcct cacatatctc    2220
cgtttagaat caggtccctt ctccccagat gaagaggagg gtctctgctt tgttttctct    2280
atctcctcct cagacttgac caggcccagc aggcccaga agaccattac cctatatccc     2340
ttctcctccc tagtcacatg gccataggcc tgctgatggc tcaggaaggc cattgcaagg    2400
actcctcagc tatgggagag gaagcacatc acccattgac ccccgcaacc cctcccttc     2460 ctcctctgag tcccgactgg ggccacatgc agcctgactt cttttgtgcct gttgctgtcc   2520 ctgcagtctt cagagggcca ccgcagctcc agtgccacgg caggaggctg ttcctgaata    2580
gcccctgtgg taagggccag gagagtcctt ccatcctcca aggccctgct aaaggacaca    2640
gcagccagga agtcccctgg gccctagct gaaggacagc ctgctccctc cgtctctacc     2700
aggaatggcc ttgtcctatg gaaggcactg ccccatccca aactaatcta ggaatcactg    2760
tctaaccact cactgtcatg aatgtgtact taaaggatga ggttgagtca taccaaatag    2820
tgatttcgat agttcaaaat ggtgaaatta gcaattctac atgattcagt ctaatcaatg    2880
gataccgact gtttccccaca caagtctcct gttctcttaa gcttactcac tgacagcctt   2940
tcactctcca caaatacatt aaagatatgg ccatcaccaa gccccctagg atgacaccag    3000
acctgagagt ctgaagacct ggatccaagt tctgactttt cccctgaca gctgtgtgac     3060 cttcgtgaag tcgccaaacc tctctgagcc ccagtcattg ctagtaagac ctgcctttga    3120
gttggtatga tgttcaagtt agataacaaa atgtttatac ccattagaac agagaataaa    3180
tagaactaca tttcttgca                                                 3199
```

<210> SEQ ID NO 5
<211> LENGTH: 3513
<212> TYPE: DNA
<213> ORGANISM: Homo sapien

```
<400> SEQUENCE: 5
tgggcaggaa ctgggcactg tgcccagggc atgcactgcc tccacgcagc aaccctcaga      60
gtcctgagct gaaccaagaa ggaggagggg gtcgggcctc cgaggaaggc ctagccgctg     120
ctgctgccag gaattccagg ttggagggc ggcaacctcc tgccagcctt caggccactc     180
tcctgtgcct gccagaagag acagagcttg aggagagctt gaggagagca ggaaagggcg     240
gcagtaagtc ttcagcatca ggcattttgg ggtgactcag taaatggtag atcttgctac     300
cagtggaaca gccactaagg attctgcagt gagagcagag ggccagctaa gtggtactct     360
cccagagact gtctgactca cgccaccccc tccaccttgg acacaggacg ctgtggtttc     420
tgagccaggt acaatgactc ctttcgcagc ctcccccgtt gccctctgg atccactgct     480 taaatacgga cgaggacagg gccctgtctc ctcagcttca ggcaccacca ctgacctggg     540
acagtgaatc gacaatgccg tcttctgtct cgtggggcat cctcctgctg gcaggcctgt     600
gctgcctggt ccctgtctcc ctggctgagg atccccaggg agatgctgcc cagaagacag     660
atacatccca ccatgatcag gatcacccaa ccttcaacaa gatcacccccc aacctggctg     720 agttcgcctt cagcctatac cgccagctgg cacaccagtc caacagcacc aatatcttct     780 tctcccagt gagcatcgct acagcctttg caatgctctc cctggggacc aaggctgaca     840
ctcacgatga atcctggag ggcctgaatt tcaacctcac ggagattccg gaggctcaga     900
tccatgaagg cttccaggaa ctcctccgta ccctcaacca gccagacagc cagctccagc     960
tgaccaccgg caatggcctg ttcctcagcg agggcctgaa gctagtggat aagttttttgg    1020 aggatgttaa aaagttgtac cactcagaag ccttcactgt caacttcggg gacaccgaag    1080
aggccaagaa acagatcaac gattacgtgg agaagggtac tcaagggaaa attgtggatt    1140
tggtcaagga gcttgacaga gacacagtt ttgctctggt gaattacatc ttctttaaag    1200
gcaaatggga gagacccttt gaagtcaagg acaccgagga agaggacttc cacgtggacc    1260
aggtgaccac cgtgaaggtg cctatgatga agcgtttagg catgtttaac atccagcact    1320
gtaagaagct gtccagctgg gtgctgctga tgaaatacct gggcaatgcc accgccatct    1380
tcttcctgcc tgatgagggg aaactacagc acctggaaaa tgaactcacc cacgatatca    1440
tcaccaagtt cctggaaaat gaagacagaa ggtctgccag cttacattta cccaaactgt    1500
ccattactgg aacctatgat ctgaagagcg tcctgggtca actgggcatc actaaggtct    1560
tcagcaatgg ggctgacctc tccggggtca cagaggaggc acccctgaag ctctccaagg    1620
ccgtgcataa ggctgtgctg accatcgacg agaaagggac tgaagctgct ggggccatgt    1680
ttttagaggc catacccatg tctatccccc ccgaggtcaa gttcaacaaa ccctttgtct    1740
tcttaatgat tgaacaaaat accaagtctc ccctcttcat gggaaaagtg gtgaatccca    1800
cccaaaaata actgcctctc gctcctcaac ccctcccctc catccctggc cccctccctg    1860
gatgacatta agaagggtt gagctggtcc ctgcctgcat gtgactgtaa atccctccca    1920
tgttttctct gagtctccct ttgcctgctg aggctgtatg tgggctccag gtaacagtgc    1980
tgtcttcggg ccccctgaac tgtgttcatg gagcatctgg ctgggtaggc acatgctggg    2040
cttgaatcca gggggactg aatcctcagc ttacggacct gggcccatct gtttctggag    2100
ggctccagtc ttccttgtcc tgtcttggag tccccaagaa ggaatcacag gggaggaacc    2160
agataccagc catgacccca ggctccacca agcatcttca tgtcccctg ctcatccccc    2220 actcccccc acccagagtt gctcatcctg ccagggctgg ctgtgcccac ccaaggctg    2280 ccctcctggg ggccccagaa ctgcctgatc gtgccgtggc ccagttttgt ggcatctgca    2340
```

| | | |
|---|---|---|
| gcaacacaag agagaggaca atgtcctcct cttgacccgc tgtcacctaa ccagactcgg | 2400 | |
| gccctgcacc tctcaggcac ttctggaaaa tgactgaggc agattcttcc tgaagcccat | 2460 | |
| tctccatggg gcaacaagga cacctattct gtccttgtcc ttccatcgct gccccagaaa | 2520 | |
| gcctcacata tctccgttta gaatcaggtc ccttctcccc agatgaagag gagggtctct | 2580 | |
| gctttgtttt ctctatctcc tcctcagact tgaccaggcc cagcaggccc cagaagacca | 2640 | |
| ttaccctata tcccttctcc tccctagtca catggccata ggcctgctga tggctcagga | 2700 | |
| aggccattgc aaggactcct cagctatggg agaggaagca catcacccat tgaccccgc | 2760 | |
| aacccctccc tttcctcctc tgagtcccga ctggggccac atgcagcctg acttctttgt | 2820 | |
| gcctgttgct gtccctgcag tcttcagagg gccaccgcag ctccagtgcc acggcaggag | 2880 | |
| gctgttcctg aatagcccct gtggtaaggg ccaggagagt ccttccatcc tccaaggccc | 2940 | |
| tgctaaagga cacagcagcc aggaagtccc ctgggcccct agctgaagga cagcctgctc | 3000 | |
| cctccgtctc taccaggaat ggccttgtcc tatggaaggc actgcccat cccaaactaa | 3060 | |
| tctaggaatc actgtctaac cactcactgt catgaatgtg tacttaaagg atgaggttga | 3120 | |
| gtcataccaa atagtgattt cgatagttca aaatggtgaa attagcaatt ctacatgatt | 3180 | |
| cagtctaatc aatggatacc gactgtttcc cacacaagtc tcctgttctc ttaagcttac | 3240 | |
| tcactgacag cctttcactc tccacaaata cattaaagat atggccatca ccaagccccc | 3300 | |
| taggatgaca ccagacctga gagtctgaag acctggatcc aagttctgac ttttcccct | 3360 | |
| gacagctgtg tgaccttcgt gaagtcgcca aacctctctg agccccagtc attgctagta | 3420 | |
| agacctgcct ttgagttggt atgatgttca agttagataa caaaatgttt atacccatta | 3480 | |
| gaacagagaa taaatagaac tacatttctt gca | 3513 | |

<210> SEQ ID NO 6
<211> LENGTH: 3236
<212> TYPE: DNA
<213> ORGANISM: Homo sapien

<400> SEQUENCE: 6

| | | |
|---|---|---|
| tgggcaggaa ctgggcactg tgcccagggc atgcactgcc tccacgcagc aaccctcaga | 60 | |
| gtcctgagct gaaccaagaa ggaggagggg gtcgggcctc cgaggaaggc ctagccgctg | 120 | |
| ctgctgccag gaattccagg ttggagggc ggcaacctcc tgccagcctt caggccactc | 180 | |
| tcctgtgcct gccagaagag acagagcttg aggagagctt gaggagagca ggaaaggtgg | 240 | |
| gacattgctg ctgctgctca ctcagttcca caggacaatg ccgtcttctg tctcgtgggg | 300 | |
| catcctcctg ctggcaggcc tgtgctgcct ggtccctgtc tccctggctg aggatcccca | 360 | |
| gggagatgct gcccagaaga cagatacatc ccaccatgat caggatcacc caaccttcaa | 420 | |
| caagatcacc cccaacctgg ctgagttcgc cttcagccta taccgccagc tggcacacca | 480 | |
| gtccaacagc accaatatct tcttctcccc agtgagcatc gctacagcct ttgcaatgct | 540 | |
| ctccctgggg accaaggctg acactcacga tgaaatcctg gagggcctga atttcaacct | 600 | |
| cacggagatt ccggaggctc agatccatga aggcttccag gaactcctcc gtaccctcaa | 660 | |
| ccagccagac agccagctcc agctgaccac cggcaatggc ctgttcctca gcgagggcct | 720 | |
| gaagctagtg gataagtttt tggaggatgt taaaaagttg taccactcag aagccttcac | 780 | |
| tgtcaacttc ggggacaccg aagaggccaa gaaacagatc aacgattacg tggagaaggg | 840 | |
| tactcaaggg aaaattgtgg atttggtcaa ggagcttgac agagacacag tttttgctct | 900 | |

```
ggtgaattac atcttcttta aaggcaaatg ggagagaccc tttgaagtca aggacaccga    960
ggaagaggac ttccacgtgg accaggtgac caccgtgaag gtgcctatga tgaagcgttt   1020
aggcatgttt aacatccagc actgtaagaa gctgtccagc tgggtgctgc tgatgaaata   1080
cctgggcaat gccaccgcca tcttcttcct gcctgatgag gggaaactac agcacctgga   1140
aaatgaactc acccacgata tcatcaccaa gttcctggaa aatgaagaca aaggtctgc    1200
cagcttacat ttacccaaac tgtccattac tggaacctat gatctgaaga gcgtcctggg   1260
tcaactgggc atcactaagg tcttcagcaa tggggctgac ctctccgggg tcacagagga   1320
ggcaccctg aagctctcca aggccgtgca taaggctgtg ctgaccatcg acgagaaagg    1380
gactgaagct gctggggcca tgttttttaga ggccataccc atgtctatcc ccccgaggt   1440
caagttcaac aaacccttg tcttcttaat gattgaacaa ataccaagt ctcccctctt     1500
catgggaaaa gtggtgaatc ccacccaaaa ataactgcct ctcgctcctc aacccctccc   1560
ctccatccct ggccccctcc ctggatgaca ttaaagaagg gttgagctgg tccctgcctg   1620
catgtgactg taaatccctc ccatgttttc tctgagtctc cctttgcctg ctgaggctgt   1680
atgtgggctc caggtaacag tgctgtcttc gggcccctg aactgtgttc atggagcatc    1740
tggctgggta ggcacatgct gggcttgaat ccagggggga ctgaatcctc agcttacgga   1800
cctgggccca tctgtttctg gagggctcca gtcttccttg tcctgtcttg gagtccccaa   1860
gaaggaatca caggggagga accagatacc agccatgacc ccaggctcca ccaagcatct   1920
tcatgtcccc ctgctcatcc cccactcccc cccacccaga gttgctcatc ctgccagggc   1980
tggctgtgcc cacccaagg ctgccctcct ggggcccca gaactgcctg atcgtgccgt     2040
ggcccagttt tgtggcatct gcagcaacac aagagagagg acaatgtcct cctcttgacc   2100
cgctgtcacc taaccagact cggggccctgc acctctcagg cacttctgga aaatgactga   2160
ggcagattct tcctgaagcc cattctccat ggggcaacaa ggacacctat tctgtccttg   2220
tccttccatc gctgccccag aaagcctcac atatctccgt ttagaatcag gtcccttctc   2280
cccagatgaa gaggagggtc tctgctttgt tttctctatc tcctcctcag acttgaccag   2340
gcccagcagg cccagaaga ccattaccct atatcccttc tcctccctag tcacatggcc    2400
ataggcctgc tgatggctca ggaaggccat tgcaaggact cctcagctat gggagaggaa   2460
gcacatcacc cattgacccc cgcaacccct cccctttcctc ctctgagtcc cgactggggc   2520
cacatgcagc ctgacttctt tgtgcctgtt gctgtccctg cagtcttcag agggccaccg   2580
cagctccagt gccacggcag gaggctgttc ctgaatagcc cctgtggtaa gggccaggag   2640
agtccttcca tcctccaagg ccctgctaaa ggacacagca gccaggaagt cccctgggcc   2700
cctagctgaa ggacagcctg ctccctccgt ctctaccagg aatggccttg tcctatggaa   2760
ggcactgccc catcccaaac taatctagga atcactgtct aaccactcac tgtcatgaat   2820
gtgtacttaa aggatgaggt tgagtcatac caaatagtga tttcgatagt tcaaaatggt   2880
gaaattagca attctacatg attcagtcta atcaatggat accgactgtt tcccacacaa   2940
gtctcctgtt ctcttaagct tactcactga cagcctttca ctctccacaa atacattaaa   3000
gatatggcca tcaccaagcc ccctaggatg acaccagacc tgagagtctg aagacctgga   3060
tccaagttct gacttttccc cctgacagct gtgtgacctt cgtgaagtcg ccaaacctct   3120
ctgagcccca gtcattgcta gtaagacctg cctttgagtt ggtatgatgt tcaagttaga   3180
taacaaaatg tttataccca ttagaacaga gaataaatag aactacattt cttgca       3236
```

<210> SEQ ID NO 7
<211> LENGTH: 3532
<212> TYPE: DNA
<213> ORGANISM: Homo sapien

<400> SEQUENCE: 7

```
tgggcaggaa ctgggcactg tgcccagggc atgcactgcc tccacgcagc aaccctcaga      60
gtcctgagct gaaccaagaa ggaggagggg gtcgggcctc cgaggaaggc ctagccgctg     120
ctgctgccag gaattccagg ttggaggggc ggcaacctcc tgccagcctt caggccactc     180
tcctgtgcct gccagaagag acagagcttg aggagagctt gaggagagca ggaaaggtgg     240
gacattgctg ctgctgctca ctcagttcca cagggcggca gtaagtcttc agcatcaggc     300
attttggggt gactcagtaa atggtagatc ttgctaccag tggaacagcc actaaggatt     360
ctgcagtgag agcagagggc cagctaagtg gtactctccc agagactgtc tgactcacgc     420
caccccctcc accttggaca caggacgctg tggtttctga gccagcagcc tccccgttg      480 cccctctgga tccactgctt aaatacggac gaggacaggg ccctgtctcc tcagcttcag     540
gcaccaccac tgacctggga cagtgaatcg acaatgccgt cttctgtctc gtgggcatc      600 ctcctgctgg caggcctgtg ctgcctggtc cctgtctccc tggctgagga tccccaggga     660
gatgctgccc agaagacaga tacatcccac catgatcagg atcacccaac cttcaacaag     720
atcaccccca acctggctga gttcgccttc agcctatacc gccagctggc acaccagtcc     780
aacagcacca atatcttctt ctccccagtg agcatcgcta cagcctttgc aatgctctcc     840
ctggggacca aggctgacac tcacgatgaa atcctgagg gcctgaattt caacctcacg     900
gagattccgg aggctcagat ccatgaaggc ttccaggaac tcctccgtac cctcaaccag     960
ccagacagcc agctccagct gaccaccggc aatggcctgt tcctcagcga gggcctgaag    1020
ctagtggata gttttttgga ggatgttaaa agttgtacc actcagaagc cttcactgtc    1080
aacttcgggg acaccgaaga ggccaagaaa cagatcaacg attacgtgga aagggtact     1140 caagggaaaa ttgtggattt ggtcaaggag cttgacagag acacagtttt tgctctggtg    1200
aattacatct tctttaaagg caaatgggag agacccttg aagtcaagga caccgaggaa    1260
gaggacttcc acgtggacca ggtgaccacc gtgaaggtgc tatgatgaa gcgtttaggc    1320 atgtttaaca tccagcactg taagaagctg tccagctggg tgctgctgat gaaatacctg    1380
ggcaatgcca ccgccatctt cttcctgcct gatgagggga aactacagca cctggaaaat    1440
gaactcaccc acgatatcat caccaagttc ctggaaaatg aagacagaag gtctgccagc    1500
ttacatttac ccaaactgtc cattactgga acctatgatc tgaagagcgt cctgggtcaa    1560
ctgggcatca ctaaggtctt cagcaatggg gctgacctct ccggggtcac agaggaggca    1620
cccctgaagc tctccaaggc cgtgcataag gctgtgctga ccatcgacga aaagggact     1680 gaagctgctg gggccatgtt tttagaggcc atacccatgt ctatccccc cgaggtcaag    1740 ttcaacaaac cctttgtctt cttaatgatt gaacaaaata ccaagtctcc cctcttcatg    1800
ggaaaagtgg tgaatcccac ccaaaaataa ctgcctctcg ctcctcaacc cctcccctcc    1860
atccctggcc ccctccctgg atgacattaa agaagggttg agctggtccc tgcctgcatg    1920
tgactgtaaa tccctcccat gttttctctg agtctccctt tgcctgctga ggctgtatgt    1980
gggctccagg taacagtgct gtcttcgggc ccctgaact gtgttcatgg agcatctggc    2040
tgggtaggca catgctgggc ttgaatccag ggggactga atcctcagct tacgacctg     2100 ggcccatctg tttctggagg gctccagtct tccttgtcct gtcttggagt ccccaagaag    2160
```

```
gaatcacagg ggaggaacca gataccagcc atgaccccag gctccaccaa gcatcttcat    2220
gtcccctgc tcatccccca ctcccccca cccagagttg ctcatcctgc cagggctggc     2280
tgtgcccacc ccaaggctgc cctcctgggg gccccagaac tgcctgatcg tgccgtggcc    2340
cagttttgtg gcatctgcag caacacaaga gagaggacaa tgtcctcctc ttgacccgct    2400
gtcacctaac cagactcggg ccctgcacct ctcaggcact tctggaaaat gactgaggca    2460
gattcttcct gaagcccatt ctccatgggg caacaaggac acctattctg tccttgtcct    2520
tccatcgctg ccccagaaag cctcacatat ctccgtttag aatcaggtcc cttctcccca    2580
gatgaagagg agggtctctg ctttgttttc tctatctcct cctcagactt gaccaggccc    2640
agcaggcccc agaagaccat taccctatat cccttctcct cctagtcac atggccatag     2700
gcctgctgat ggctcaggaa ggccattgca aggactcctc agctatggga gaggaagcac    2760
atcacccatt gaccccgca accctccct ttcctcctct gagtcccgac tggggccaca      2820
tgcagcctga cttctttgtg cctgttgctg tccctgcagt cttcagaggg ccaccgcagc    2880
tccagtgcca cggcaggagg ctgttcctga atagcccctg tggtaaggc caggagagtc     2940
cttccatcct ccaaggccct gctaaaggac acagcagcca ggaagtcccc tgggcccta    3000
gctgaaggac agcctgctcc ctccgtctct accaggaatg ccttgtcct atggaaggca    3060
ctgccccatc ccaaactaat ctaggaatca ctgtctaacc actcactgtc atgaatgtgt    3120
acttaaagga tgaggttgag tcataccaaa tagtgatttc gatagttcaa aatggtgaaa    3180
ttagcaattc tacatgattc agtctaatca atggataccg actgtttccc acacaagtct    3240
cctgttctct taagcttact cactgacagc ctttcactct ccacaaatac attaaagata    3300
tggccatcac caagcccct aggatgacac cagacctgag agtctgaaga cctggatcca     3360
agttctgact tttcccctg acagctgtgt gaccttcgtg aagtcgccaa acctctctga    3420
gccccagtca ttgctagtaa gacctgcctt tgagttggta tgatgttcaa gttagataac    3480
aaaatgttta tacccattag aacagagaat aaatagaact acatttcttg ca            3532
```

<210> SEQ ID NO 8
<211> LENGTH: 3340
<212> TYPE: DNA
<213> ORGANISM: Homo sapien

<400> SEQUENCE: 8

```
tgggcaggaa ctgggcactg tgcccagggc atgcactgcc tccacgcagc aaccctcaga     60
gtcctgagct gaaccaagaa ggaggagggg gtcgggcctc cgaggaaggc ctagccgctg    120
ctgctgccag gaattccagg ttggaggggc ggcaacctcc tgccagcctt caggccactc    180
tcctgtgcct gccagaagag acagagcttg aggagagctt gaggagagca ggaaaggtgg    240
gacattgctg ctgctgctca ctcagttcca cagcagcctc cccgttgcc cctctggatc     300
cactgcttaa atacggacga ggacagggcc ctgtctcctc agcttcaggc accaccactg    360
acctgggaca gtgaatcgac aatgccgtct tctgtctcgt ggggcatcct cctgctggca    420
ggcctgtgct gcctggtccc tgtctccctg gctgaggatc cccagggaga tgctgcccag    480
aagacagata catcccacca tgatcaggat cacccaacct tcaacaagat cacccccaac    540
ctggctgagt tcgccttcag cctataccgc cagctggcac accagtccaa cagcaccaat    600
atcttcttct ccccagtgag catcgctaca gcctttgcaa tgctctccct ggggaccaag    660
gctgacactc acgatgaaat cctggagggc ctgaatttca acctcacgga gattccggag    720
gctcagatcc atgaaggctt ccaggaactc ctccgtaccc tcaaccagcc agacagccag    780
```

```
ctccagctga ccaccggcaa tggcctgttc ctcagcgagg gcctgaagct agtggataag      840
tttttggagg atgttaaaaa gttgtaccac tcagaagcct tcactgtcaa cttcggggac      900
accgaagagg ccaagaaaca gatcaacgat tacgtggaga agggtactca agggaaaatt      960
gtggatttgg tcaaggagct tgacagagac acagttttg ctctggtgaa ttacatcttc      1020
tttaaaggca aatgggagag acccttgaa gtcaaggaca ccgaggaaga ggacttccac      1080
gtggaccagg tgaccaccgt gaaggtgcct atgatgaagc gtttaggcat gtttaacatc      1140
cagcactgta agaagctgtc cagctgggtg ctgctgatga ataccctggg caatgccacc      1200
gccatcttct tcctgcctga tgaggggaaa ctacagcacc tggaaaatga actcacccac      1260
gatatcatca ccaagttcct ggaaaatgaa gacagaaggt ctgccagctt acatttaccc      1320
aaactgtcca ttactggaac ctatgatctg aagagcgtcc tgggtcaact gggcatcact      1380
aaggtcttca gcaatggggc tgacctctcc ggggtcacag aggaggcacc cctgaagctc      1440
tccaaggccg tgcataaggc tgtgctgacc atcgacgaga aagggactga agctgctggg      1500
gccatgtttt tagaggccat acccatgtct atccccccg aggtcaagtt caacaaaccc      1560
tttgtcttct taatgattga acaaaatacc aagtctcccc tcttcatggg aaaagtggtg      1620
aatcccaccc aaaaataact gcctctcgct cctcaacccc tcccctccat ccctggcccc      1680
ctccctggat gacattaaag aagggttgag ctggtccctg cctgcatgtg actgtaaatc      1740
cctcccatgt tttctctgag tctcccttg cctgctgagg ctgtatgtgg gctccaggta      1800
acagtgctgt cttcgggccc cctgaactgt gttcatggag catctggctg ggtaggcaca      1860
tgctgggctt gaatccaggg gggactgaat cctcagctta cggacctggg cccatctgtt      1920
tctggagggc tccagtcttc cttgtcctgt cttggagtcc ccaagaagga atcacagggg      1980
aggaaccaga taccagccat gaccccaggc tccaccaagc atcttcatgt cccctgctc      2040 atccccccact ccccccacc cagagttgct catcctgcca gggctggctg tgcccacccc      2100
aaggctgccc tcctgggggc cccagaactg cctgatcgtg ccgtggccca gttttgtggc      2160
atctgcagca acacaagaga gaggacaatg tcctcctctt gacccgctgt cacctaacca      2220
gactcgggcc ctgcacctct caggcacttc tggaaaatga ctgaggcaga ttcttcctga      2280
agcccattct ccatggggca acaaggacac ctattctgtc cttgtccttc catcgctgcc      2340
ccagaaagcc tcacatatct ccgtttagaa tcaggtccct tctccccaga tgaagaggag      2400
ggtctctgct ttgttttctc tatctcctcc tcagacttga ccaggccag caggccccag      2460 aagaccatta ccctatatcc cttctcctcc ctagtcacat ggccataggc ctgctgatgg      2520
ctcaggaagg ccattgcaag gactcctcag ctatgggaga ggaagcacat cacccattga      2580
cccccgcaac ccctccctt cctcctctga gtcccgactg gggccacatg cagcctgact      2640
tctttgtgcc tgttgctgtc cctgcagtct tcagagggcc accgcagctc cagtgccacg      2700
gcaggaggct gttcctgaat agccctgtg gtaaggccca ggagagtcct tccatcctcc      2760
aaggccctgc taaaggacac agcagccagg aagtcccctg ggcccctagc tgaaggacag      2820
cctgctccct ccgtctctac caggaatggc cttgtcctat ggaaggcact gccccatccc      2880
aaactaatct aggaatcact gtctaaccac tcactgtcat gaatgtgtac ttaaaggatg      2940
aggttgagtc ataccaaata gtgatttcga tagttcaaaa tggtgaaatt agcaattcta      3000
catgattcag tctaatcaat ggataccgac tgtttcccac acaagtctcc tgttctctta      3060
agcttactca ctgacagcct ttcactctcc acaaatacat taaagatatg gccatcacca      3120
```

-continued

| | |
|---|---|
| agcccctag gatgacacca gacctgagag tctgaagacc tggatccaag ttctgacttt | 3180 |
| tcccctgac agctgtgtga ccttcgtgaa gtcgccaaac ctctctgagc cccagtcatt | 3240 |
| gctagtaaga cctgcctttg agttggtatg atgttcaagt tagataacaa aatgtttata | 3300 |
| cccattagaa cagagaataa atagaactac atttcttgca | 3340 |

<210> SEQ ID NO 9
<211> LENGTH: 3495
<212> TYPE: DNA
<213> ORGANISM: Homo sapien

<400> SEQUENCE: 9

| | |
|---|---|
| tgggcaggaa ctgggcactg tgcccagggc atgcactgcc tccacgcagc aaccctcaga | 60 |
| gtcctgagct gaaccaagaa ggaggagggg gtcgggcctc cgaggaaggc ctagccgctg | 120 |
| ctgctgccag gaattccagg ttggaggggc ggcaacctcc tgccagcctt caggccactc | 180 |
| tcctgtgcct gccagaagag acagagcttg aggagagctt gaggagagca ggaaagggcg | 240 |
| gcagtaagtc ttcagcatca ggcattttgg ggtgactcag taaatggtag atcttgctac | 300 |
| cagtggaaca gccactaagg attctgcagt gagagcagag ggccagctaa gtggtactct | 360 |
| cccagagact gtctgactca cgccaccccc tccaccttgg acacaggacg ctgtggtttc | 420 |
| tgagccagca gcctccccg ttgcccctct ggatccactg cttaaatacg gacgaggaca | 480 |
| gggccctgtc tcctcagctt caggcaccac cactgacctg ggacagtgaa tcgacaatgc | 540 |
| cgtcttctgt ctcgtggggc atcctcctgc tggcaggcct gtgctgcctg gtccctgtct | 600 |
| ccctggctga ggatccccag ggagatgctg cccagaagac agatacatcc caccatgatc | 660 |
| aggatcaccc aaccttcaac aagatcaccc ccaacctggc tgagttcgcc ttcagcctat | 720 |
| accgccagct ggcacaccag tccaacagca ccaatatctt cttctcccca gtgagcatcg | 780 |
| ctacagcctt tgcaatgctc tccctgggga ccaaggctga cactcacgat gaaatcctgg | 840 |
| agggcctgaa tttcaacctc acggagattc cggaggctca gatccatgaa ggcttccagg | 900 |
| aactcctccg taccctcaac cagccagaca gccagctcca gctgaccacc ggcaatggcc | 960 |
| tgttcctcag cgagggcctg aagctagtgg ataagtttt ggaggatgtt aaaaagttgt | 1020 |
| accactcaga agccttcact gtcaacttcg ggacaccga agaggccaag aaacagatca | 1080 |
| acgattacgt ggagaagggt actcaaggga aaattgtgga tttggtcaag agcttgaca | 1140 |
| gagacacagt ttttgctctg gtgaattaca tcttctttaa aggcaaatgg gagagaccct | 1200 |
| ttgaagtcaa ggacaccgag gaagaggact tccacgtgga ccaggtgacc accgtgaagg | 1260 |
| tgcctatgat gaagcgttta ggcatgtta acatccagca ctgtaagaag ctgtccagct | 1320 |
| gggtgctgct gatgaaatac ctgggcaatg ccaccgccat cttcttcctg cctgatgagg | 1380 |
| ggaaactaca gcacctggaa aatgaactca cccacgatat catcaccaag ttcctggaaa | 1440 |
| atgaagacag aaggtctgcc agcttacatt tacccaaact gtccattact ggaacctatg | 1500 |
| atctgaagag cgtcctgggt caactgggca tcactaaggt cttcagcaat ggggctgacc | 1560 |
| tctccggggt cacagaggag gcacccctga agctctccaa ggccgtgcat aaggctgtgc | 1620 |
| tgaccatcga cgagaaaggg actgaagctg ctggggccat gttttagag gccatacccca | 1680 |
| tgtctatccc ccccgaggtc aagttcaaca aacccttgt cttcttaatg attgaacaaa | 1740 |
| ataccaagtc tccctctctt atgggaaaag tggtgaatcc cacccaaaaa taactgcctc | 1800 |
| tcgctcctca acccctcccc tccatccctg gcccctccc tggatgacat taagaaggg | 1860 |
| ttgagctggt ccctgcctgc atgtgactgt aaatccctcc catgttttct ctgagtctcc | 1920 |

-continued

```
ctttgcctgc tgaggctgta tgtgggctcc aggtaacagt gctgtcttcg ggccccctga    1980
actgtgttca tggagcatct ggctgggtag gcacatgctg ggcttgaatc cagggggggac   2040 tgaatcctca gcttacggac ctgggcccat ctgtttctgg agggctccag tcttccttgt    2100
cctgtcttgg agtccccaag aaggaatcac aggggaggaa ccagatacca gccatgaccc    2160
caggctccac caagcatctt catgtccccc tgctcatccc ccactccccc ccacccagag    2220
ttgctcatcc tgccagggct ggctgtgccc accccaaggc tgccctcctg ggggcccag     2280 aactgcctga tcgtgccgtg gcccagtttt gtggcatctg cagcaacaca agagagagga    2340
caatgtcctc ctcttgaccc gctgtcacct aaccagactc gggccctgca cctctcaggc    2400
acttctggaa aatgactgag gcagattctt cctgaagccc attctccatg gggcaacaag    2460
gacacctatt ctgtccttgt ccttccatcg ctgccccaga aagcctcaca tatctccgtt    2520
tagaatcagg tcccttctcc ccagatgaag aggagggtct ctgctttgtt ttctctatct    2580
cctcctcaga cttgaccagg cccagcaggc cccagaagac cattacccta tatcccttct    2640
cctccctagt cacatggcca taggcctgct gatggctcag gaaggccatt gcaaggactc    2700
ctcagctatg ggagaggaag cacatcaccc attgacccccc gcaaccccctc cctttcctcc   2760 tctgagtccc gactggggcc acatgcagcc tgacttcttt gtgcctgttg ctgtccctgc    2820
agtcttcaga gggccaccgc agctccagtg ccacggcagg aggctgttcc tgaatagccc    2880
ctgtggtaag ggccaggaga gtccttccat cctccaaggc cctgctaaag gacacagcag    2940
ccaggaagtc ccctgggccc ctagctgaag gacagcctgc tccctccgtc tctaccagga    3000
atggccttgt cctatggaag gcactgcccc atcccaaact aatctaggaa tcactgtcta    3060
accactcact gtcatgaatg tgtacttaaa ggatgaggtt gagtcatacc aaatagtgat    3120
ttcgatagtt caaaatggtg aaattagcaa ttctacatga ttcagtctaa tcaatggata    3180
ccgactgttt cccacacaag tctcctgttc tcttaagctt actcactgac agcctttcac    3240
tctccacaaa tacattaaag atatggccat caccaagccc cctaggatga caccagacct    3300
gagagtctga agacctggat ccaagttctg acttttcccc ctgacagctg tgtgaccttc    3360
gtgaagtcgc caaacctctc tgagcccag tcattgctag taagacctgc ctttgagttg    3420
gtatgatgtt caagttagat aacaaaatgt ttatacccat tagaacagag aataaataga    3480
actacatttc ttgca                                                     3495
```

<210> SEQ ID NO 10
<211> LENGTH: 3492
<212> TYPE: DNA
<213> ORGANISM: Homo sapien
<400> SEQUENCE: 10

```
tgggcaggaa ctgggcactg tgcccagggc atgcactgcc tccacgcagc aaccctcaga     60
gtcctgagct gaaccaagaa ggaggagggg gtcgggcctc cgaggaaggc ctagccgctg    120
ctgctgccag gaattccagg ttggaggggc ggcaacctcc tgccagcctt caggccactc    180
tcctgtgcct gccagaagag acagagcttg aggagagctt gaggagagca ggaaagggcg    240
gcagtaagtc ttcagcatca ggcattttgg ggtgactcag taaatggtag atcttgctac    300
cagtggaaca gccactaagg attctgcagt gagagcagag ggccagctaa gtggtactct    360
cccagagact gtctgactca cgccaccccc tccaccttgg acacaggacg ctgtggtttc    420
tgagccagcc tcccccgttg cccctctgga tccactgctt aaatacggac gaggacaggg    480
```

```
ccctgtctcc tcagcttcag gcaccaccac tgacctggga cagtgaatcg acaatgccgt    540
cttctgtctc gtggggcatc ctcctgctgg caggcctgtg ctgcctggtc cctgtctccc    600
tggctgagga tccccaggga gatgctgccc agaagacaga tacatcccac catgatcagg    660
atcacccaac cttcaacaag atccccccca acctggctga gttcgccttc agcctatacc    720
gccagctggc acaccagtcc aacagcacca atatcttctt ctccccagtg agcatcgcta    780
cagcctttgc aatgctctcc ctggggacca aggctgacac tcacgatgaa atcctggagg    840
gcctgaattt caacctcacg gagattccgg aggctcagat ccatgaaggc ttccaggaac    900
tcctccgtac cctcaaccag ccagacagcc agctccagct gaccaccggc aatggcctgt    960
tcctcagcga gggcctgaag ctagtggata agttttttgga ggatgttaaa aagttgtacc   1020
actcagaagc cttcactgtc aacttcgggg acaccgaaga ggccaagaaa cagatcaacg   1080
attacgtgga agggtact caagggaaaa ttgtggattt ggtcaaggag cttgacagag      1140
acacagtttt tgctctggtg aattacatct tctttaaagg caaatgggag agacccttg    1200
aagtcaagga caccgaggaa gaggacttcc acgtggacca ggtgaccacc gtgaaggtgc   1260
ctatgatgaa gcgtttaggc atgtttaaca tccagcactg taagaagctg tccagctggg   1320
tgctgctgat gaaatacctg ggcaatgcca ccgccatctt cttcctgcct gatgagggga   1380
aactacagca cctggaaaat gaactcaccc acgatatcat caccaagttc ctggaaaatg   1440
aagacagaag gtctgccagc ttacatttac ccaaaactgtc cattactgga acctatgatc   1500
tgaagagcgt cctgggtcaa ctgggcatca ctaaggtctt cagcaatggg gctgacctct   1560
ccggggtcac agaggaggca cccctgaagc tctccaaggc cgtgcataag gctgtgctga   1620
ccatcgacga gaaagggact gaagctgctg gggccatgtt tttagaggcc atacccatgt   1680
ctatccccc cgaggtcaag ttcaacaaac cctttgtctt cttaatgatt gaacaaaata    1740
ccaagtctcc cctcttcatg ggaaaagtgg tgaatcccac ccaaaaataa ctgcctctcg   1800
ctcctcaacc cctcccctcc atccctggcc ccctccctgg atgacattaa gaagggttg    1860
agctggtccc tgcctgcatg tgactgtaaa tccctcccat gttttctctg agtctcccct   1920
tgcctgctga ggctgtatgt gggctccagg taacagtgct gtcttcgggc cccctgaact   1980
gtgttcatgg agcatctggc tgggtaggca catgctgggc ttgaatccag gggggactga   2040
atcctcagct tacggacctg ggcccatctg tttctggagg gctccagtct tccttgtcct   2100
gtcttggagt ccccaagaag gaatcacagg ggaggaacca gataccagcc atgacccag   2160
gctccaccaa gcatcttcat gtcccccctg tcatccccca ctccccccca cccagagttg   2220
ctcatcctgc cagggctggc tgtgcccacc ccaaggctgc cctcctgggg gcccagaac   2280
tgcctgatcg tgccgtggcc cagttttgtg gcatctgcag caacacaaga gagaggacaa   2340
tgtcctcctc ttgacccgct gtcacctaac cagactcggg ccctgcacct ctcaggcact   2400
tctggaaaat gactgaggca gattcttcct gaagcccatt ctccatgggg caacaaggac   2460
acctattctg tccttgtcct tccatcgctg ccccagaaag cctcacatat ctccgtttag   2520
aatcaggtcc cttctcccca gatgaagagg agggtctctg ctttgttttc tctatctcct   2580
cctcagactt gaccagcccc agcaggcccc agaagaccat tacctatat cccttctcct    2640
ccctagtcac atggccatag gctgctgat ggctcaggaa ggccattgca aggactcctc    2700
agctatggga gaggaagcac atcacccatt gaccccgca accccctccct ttcctcctct   2760
gagtcccgac tgggggccaca tgcagcctga cttctttgtg cctgttgctg tccctgcagt   2820
cttcagaggg ccaccgcagc tccagtgcca cggcaggagg ctgttcctga atagcccctg   2880
```

-continued

| | | | |
|---|---|---|---|
| tggtaagggc | caggagagtc | cttccatcct | ccaaggccct gctaaaggac acagcagcca | 2940 |
| ggaagtcccc | tgggccccta | gctgaaggac | agcctgctcc ctccgtctct accaggaatg | 3000 |
| gccttgtcct | atggaaggca | ctgccccatc | ccaaactaat ctaggaatca ctgtctaacc | 3060 |
| actcactgtc | atgaatgtgt | acttaaagga | tgaggttgag tcataccaaa tagtgatttc | 3120 |
| gatagttcaa | aatggtgaaa | ttagcaattc | tacatgattc agtctaatca atggataccg | 3180 |
| actgtttccc | acacaagtct | cctgttctct | taagcttact cactgacagc ctttcactct | 3240 |
| ccacaaatac | attaaagata | tggccatcac | caagccccct aggatgacac cagacctgag | 3300 |
| agtctgaaga | cctggatcca | agttctgact | tttccccctg acagctgtgt gaccttcgtg | 3360 |
| aagtcgccaa | acctctctga | gccccagtca | ttgctagtaa gacctgcctt tgagttggta | 3420 |
| tgatgttcaa | gttagataac | aaaatgttta | tacccattag aacagagaat aaatagaact | 3480 |
| acatttcttg | ca | | | 3492 |

<210> SEQ ID NO 11
<211> LENGTH: 3510
<212> TYPE: DNA
<213> ORGANISM: Homo sapien

<400> SEQUENCE: 11

| | | | |
|---|---|---|---|
| tgggcaggaa | ctgggcactg | tgcccagggc | atgcactgcc tccacgcagc aaccctcaga | 60 |
| gtcctgagct | gaaccaagaa | ggaggagggg | gtcgggcctc cgaggaaggc ctagccgctg | 120 |
| ctgctgccag | gaattccagg | ttggaggggc | ggcaacctcc tgccagcctt caggccactc | 180 |
| tcctgtgcct | gccagaagag | acagagcttg | aggagagctt gaggagagca ggaaagggcg | 240 |
| gcagtaagtc | ttcagcatca | ggcattttgg | ggtgactcag taaatggtag atcttgctac | 300 |
| cagtggaaca | gccactaagg | attctgcagt | gagagcagag ggccagctaa gtggtactct | 360 |
| cccagagact | gtctgactca | cgccacccc | tccaccttgg acacaggacg ctgtggtttc | 420 |
| tgagccaggt | acaatgactc | ctttcgcctc | ccccgttgcc cctctggatc cactgcttaa | 480 |
| atacggacga | ggacagggcc | ctgtctcctc | agcttcaggc accaccactg acctgggaca | 540 |
| gtgaatcgac | aatgccgtct | tctgtctcgt | ggggcatcct cctgctggca ggcctgtgct | 600 |
| gcctggtccc | tgtctccctg | gctgaggatc | cccagggaga tgctgcccag aagacagata | 660 |
| catcccacca | tgatcaggat | cacccaacct | tcaacaagat caccccccaac ctggctgagt | 720 |
| tcgccttcag | cctataccgc | cagctggcac | accagtccaa cagcaccaat atcttcttct | 780 |
| ccccagtgag | catcgctaca | gccttttgcaa | tgctctccct ggggaccaag gctgacactc | 840 |
| acgatgaaat | cctggagggc | ctgaatttca | acctcacgga gattccggag gctcagatcc | 900 |
| atgaaggctt | ccaggaactc | ctccgtaccc | tcaaccagcc agacagccag ctccagctga | 960 |
| ccaccggcaa | tggcctgttc | ctcagcgagg | gcctgaagct agtggataag ttttggagg | 1020 |
| atgttaaaaa | gttgtaccac | tcagaagcct | tcactgtcaa cttcggggac accgaagagg | 1080 |
| ccaagaaaca | gatcaacgat | tacgtggaga | agggtactca agggaaaatt gtggatttgg | 1140 |
| tcaaggagct | tgacagagac | acagtttttg | ctctggtgaa ttacatcttc tttaaaggca | 1200 |
| aatgggagag | accctttgaa | gtcaaggaca | ccgaggaaga ggacttccac gtggaccagg | 1260 |
| tgaccaccgt | gaaggtgcct | atgatgaagc | gtttaggcat gtttaacatc cagcactgta | 1320 |
| agaagctgtc | cagctgggtg | ctgctgatga | aatacctggg caatgccacc gccatcttct | 1380 |
| tcctgcctga | tgaggggaaa | ctacagcacc | tggaaaatga actcacccac gatatcatca | 1440 |

```
ccaagttcct ggaaaatgaa gacagaaggt ctgccagctt acatttaccc aaactgtcca    1500
ttactggaac ctatgatctg aagagcgtcc tgggtcaact gggcatcact aaggtcttca    1560
gcaatggggc tgacctctcc ggggtcacag aggaggcacc cctgaagctc tccaaggccg    1620
tgcataaggc tgtgctgacc atcgacgaga aagggactga agctgctggg gccatgtttt    1680
tagaggccat acccatgtct atccccccg aggtcaagtt caacaaaccc tttgtcttct    1740
taatgattga acaaaatacc aagtctcccc tcttcatggg aaaagtggtg aatcccaccc    1800
aaaaataact gcctctcgct cctcaacccc tccctccat ccctggcccc ctccctggat    1860
gacattaaag aagggttgag ctggtccctg cctgcatgtg actgtaaatc cctcccatgt    1920
tttctctgag tctccctttg cctgctgagg ctgtatgtgg gctccaggta acagtgctgt    1980
cttcgggccc cctgaactgt gttcatggag catctggctg ggtaggcaca tgctgggctt    2040
gaatccaggg gggactgaat cctcagctta cggacctggg cccatctgtt tctggagggc    2100
tccagtcttc cttgtcctgt cttggagtcc caagaagga atcacagggg aggaaccaga    2160
taccagccat gaccccaggc tccaccaagc atcttcatgt cccctgctc atcccccact    2220 cccccccacc cagagttgct catcctgcca gggctggctg tgcccacccc aaggctgccc    2280
tcctgggggc cccagaactg cctgatcgtg ccgtggccca gttttgtggc atctgcagca    2340
acacaagaga gaggacaatg tcctcctctt gacccgctgt cacctaacca gactcgggcc    2400
ctgcacctct caggcacttc tggaaaatga ctgaggcaga ttcttcctga gcccattct    2460 ccatggggca acaaggacac ctattctgtc cttgtccttc catcgctgcc ccagaaagcc    2520
tcacatatct ccgtttagaa tcaggtccct tctccccaga tgaagaggag ggtctctgct    2580
ttgttttctc tatctcctcc tcagacttga ccaggcccag caggcccag aagaccatta    2640 ccctatatcc cttctcctcc ctagtcacat ggccataggc ctgctgatgg ctcaggaagg    2700
ccattgcaag gactcctcag ctatgggaga ggaagcacat cacccattga ccccgcaac    2760 ccctcccttt cctcctctga gtcccgactg gggccacatg cagcctgact tctttgtgcc    2820
tgttgctgtc cctgcagtct tcagagggcc accgcagctc cagtgccacg gcaggaggct    2880
gttcctgaat agcccctgtg gtaagggcca ggagagtcct tccatcctcc aagggccctgc   2940 taaaggacac agcagccagg aagtcccctg ggcccctagc tgaaggacag cctgctccct    3000
ccgtctctac caggaatggc cttgtcctat ggaaggcact gccccatccc aaactaatct    3060
aggaatcact gtctaaccac tcactgtcat gaatgtgtac ttaaaggatg aggttgagtc    3120
ataccaaata gtgatttcga tagttcaaaa tggtgaaatt agcaattcta catgattcag    3180
tctaatcaat ggataccgac tgtttcccac acaagtctcc tgttctctta agcttactca    3240 ctgcagcct ttcactctcc acaaatacat taaagatatg gccatcacca agcccctag    3300 gatgacacca gacctgagag tctgaagacc tggatccaag ttctgacttt tccccctgac    3360
agctgtgtga ccttcgtgaa gtcgccaaac ctctctgagc cccagtcatt gctagtaaga    3420
cctgcctttg agttggtatg atgttcaagt tagataacaa aatgtttata cccattagaa    3480
cagagaataa atagaactac atttcttgca                                     3510
```

<210> SEQ ID NO 12
<211> LENGTH: 3303
<212> TYPE: DNA
<213> ORGANISM: Homo sapien

<400> SEQUENCE: 12

```
tgggcaggaa ctgggcactg tgcccagggc atgcactgcc tccacgcagc aaccctcaga      60
```

```
gtcctgagct gaaccaagaa ggaggagggg gtcgggcctc cgaggaaggc ctagccgctg    120
ctgctgccag gaattccagg ttggaggggc ggcaacctcc tgccagcctt caggccactc    180
tcctgtgcct gccagaagag acagagcttg aggagagctt gaggagagca ggaaagcagc    240
ctcccccgtt gccctctgg atccactgct taaatacgga cgaggacagg gccctgtctc     300
ctcagcttca ggcaccacca ctgacctggg acagtgaatc gacaatgccg tcttctgtct    360
cgtggggcat cctcctgctg gcaggcctgt gctgcctggt ccctgtctcc ctggctgagg    420
atccccaggg agatgctgcc cagaagacag atacatccca ccatgatcag gatcacccaa    480
ccttcaacaa gatcaccccc aacctggctg agttcgcctt cagcctatac cgccagctgg    540
cacaccagtc caacagcacc aatatcttct tctccccagt gagcatcgct acagcctttg    600
caatgctctc cctggggacc aaggctgaca ctcacgatga aatcctggag ggcctgaatt    660
tcaacctcac ggagattccg gaggctcaga tccatgaagg cttccaggaa ctcctccgta    720
ccctcaacca gccagacagc cagctccagc tgaccaccgg caatggcctg ttcctcagcg    780
agggcctgaa gctagtggat aagttttggg aggatgttaa aaagttgtac cactcagaag    840
ccttcactgt caacttcggg gacaccgaag aggccaagaa acagatcaac gattacgtgg    900
agaagggtac tcaagggaaa attgtggatt tggtcaagga gcttgacaga gacacagttt    960
ttgctctggt gaattacatc ttctttaaag gcaaatggga gagacccttt gaagtcaagg   1020
acaccgagga gaggacttc cacgtggacc aggtgaccac cgtgaaggtg cctatgatga    1080
agcgtttagg catgtttaac atccagcact gtaagaagct gtccagctgg gtgctgctga   1140
tgaaatacct gggcaatgcc accgccatct tcttcctgcc tgatgagggg aaactacagc   1200
acctggaaaa tgaactcacc cacgatatca tcaccaagtt cctggaaaat gaagacagaa   1260
ggtctgccag cttacattta cccaaactgt ccattactgg aacctatgat ctgaagagcg   1320
tcctgggtca actgggcatc actaaggtct tcagcaatgg ggctgacctc tccggggtca   1380
cagaggaggc accctgaag ctctccaagg ccgtgcataa ggctgtgctg accatcgacg    1440
agaaagggac tgaagctgct ggggccatgt ttttagaggc catacccatg tctatccccc    1500
ccgaggtcaa gttcaacaaa ccctttgtct tcttaatgat tgaacaaaat accaagtctc    1560
ccctcttcat gggaaaagtg gtgaatccca cccaaaaata actgcctctc gctcctcaac    1620
ccctcccctc catccctggc cccctccctg gatgacatta agaagggtt gagctggtcc     1680 ctgcctgcat gtgactgtaa atccctccca tgttttctct gagtctccct ttgcctgctg    1740
aggctgtatg tgggctccag gtaacagtgc tgtcttcggg cccctgaac tgtgttcatg     1800 gagcatctgg ctgggtaggc acatgctggg cttgaatcca gggggactg aatcctcagc    1860 ttacggacct gggcccatct gtttctggag ggctccagtc ttccttgtcc tgtcttggag    1920
tccccaagaa ggaatcacag gggaggaacc agataccagc catgacccca ggctccacca    1980
agcatcttca tgtcccctg ctcatccccc actcccccc acccgagagtt gctcatcctg     2040 ccagggctgg ctgtgcccac cccaaggctg ccctcctggg ggcccagaa ctgcctgatc     2100 gtgccgtggc ccagttttgt ggcatctgca gcaacacaag agagaggaca atgtcctcct    2160
cttgacccgc tgtcacctaa ccagactcgg gccctgcacc tctcaggcac ttctggaaaa    2220
tgactgaggc agattcttcc tgaagcccat tctccatggg gcaacaagga cacctattct    2280
gtccttgtcc ttccatcgct gccccagaaa gcctcacata tctccgttta gaatcaggtc    2340
ccttctcccc agatgaagag gagggtctct gctttgtttt ctctatctcc tcctcagact    2400
```

```
tgaccaggcc cagcaggccc cagaagacca ttaccctata tcccttctcc tccctagtca    2460
catggccata ggcctgctga tggctcagga aggccattgc aaggactcct cagctatggg    2520
agaggaagca catcacccat tgaccccgc aaccctccc tttcctcctc tgagtcccga     2580
ctggggccac atgcagcctg acttctttgt gcctgttgct gtccctgcag tcttcagagg    2640
gccaccgcag ctccagtgcc acggcaggag gctgttcctg aatagcccct gtggtaaggg    2700
ccaggagagt ccttccatcc tccaaggccc tgctaaagga cacagcagcc aggaagtccc    2760
ctgggcccct agctgaagga cagcctgctc cctccgtctc taccaggaat ggccttgtcc    2820
tatggaaggc actgccccat cccaaaactaa tctaggaatc actgtctaac cactcactgt    2880
catgaatgtg tacttaaagg atgaggttga gtcataccaa atagtgattt cgatagttca    2940
aaatggtgaa attagcaatt ctacatgatt cagtctaatc aatggatacc gactgtttcc    3000
cacacaagtc tcctgttctc ttaagcttac tcactgacag cctttcactc tccacaaata    3060
cattaaagat atggccatca ccaagccccc taggatgaca ccagacctga gagtctgaag    3120
acctggatcc aagttctgac ttttccccct gacagctgtg tgaccttcgt gaagtcgcca    3180
aacctctctg agcccagtc attgctagta agacctgcct ttgagttggt atgatgttca    3240
agttagataa caaaatgttt atacccatta gaacagagaa taaatagaac tacatttctt    3300
gca                                                                  3303

<210> SEQ ID NO 13
<211> LENGTH: 3300
<212> TYPE: DNA
<213> ORGANISM: Homo sapien

<400> SEQUENCE: 13
tgggcaggaa ctgggcactg tgcccagggc atgcactgcc tccacgcagc aaccctcaga      60
gtcctgagct gaaccaagaa ggaggagggg gtcgggcctc cgaggaaggc ctagccgctg    120
ctgctgccag gaattccagg ttggagggg ggcaacctcc tgccagcctt caggccactc    180
tcctgtgcct gccagaagag acagagcttg aggagagctt gaggagagca ggaaagcctc    240
ccccgttgcc cctctggatc cactgcttaa atacggacga ggacagggcc ctgtctcctc    300
agcttcaggc accaccactg acctgggaca gtgaatcgac aatgccgtct tctgtctcgt    360
ggggcatcct cctgctggca ggcctgtgct gcctggtccc tgtctccctg ctgaggatc    420
cccagggaga tgctgcccag aagacagata catcccacca tgatcaggat cacccaacct    480
tcaacaagat caccccccaac ctggctgagt tcgccttcag cctataccgc cagctggcac    540
accagtccaa cagcaccaat atcttcttct ccccagtgag catcgctaca gcctttgcaa    600
tgctctccct ggggaccaag gctgacactc acgatgaaat cctggagggc ctgaatttca    660
acctcacgga gattccggag gctcagatcc atgaaggctt ccaggaactc ctccgtaccc    720
tcaaccagcc agacagccag ctccagctga ccaccggcaa tggcctgttc ctcagcgagg    780
gcctgaagct agtggataag ttttttggagg atgttaaaaa gttgtaccac tcagaagcct    840
tcactgtcaa cttcggggac accgaagagg ccaagaaaca gatcaacgat tacgtggaga    900
agggtactca agggaaaatt gtggatttgg tcaaggagct tgacagagac acagtttttg    960
ctctggtgaa ttacatcttc tttaaaggca atgggagag accctttgaa gtcaaggaca    1020
ccgaggaaga ggacttccac gtggaccagg tgaccaccgt gaaggtgcct atgatgaagc    1080
gtttaggcat gtttaacatc cagcactgta agaagctgtc cagctgggtg ctgctgatga    1140
aatacctggg caatgccacc gccatcttct tcctgcctga tgaggggaaa ctacagcacc    1200
```

```
tggaaaatga actcacccac gatatcatca ccaagttcct ggaaaatgaa gacagaaggt    1260
ctgccagctt acatttaccc aaactgtcca ttactggaac ctatgatctg aagagcgtcc    1320
tgggtcaact gggcatcact aaggtcttca gcaatggggc tgacctctcc ggggtcacag    1380
aggaggcacc cctgaagctc tccaaggccg tgcataaggc tgtgctgacc atcgacgaga    1440
aagggactga agctgctggg gccatgtttt tagaggccat acccatgtct atcccccccg    1500
aggtcaagtt caacaaaccc tttgtcttct taatgattga acaaaatacc aagtctcccc    1560
tcttcatggg aaaagtggtg aatcccaccc aaaaataact gcctctcgct cctcaacccc    1620
tcccctccat ccctggcccc ctccctggat gacattaaag aagggttgag ctggtccctg    1680
cctgcatgtg actgtaaatc cctcccatgt tttctctgag tctccctttg cctgctgagg    1740
ctgtatgtgg gctccaggta acagtgctgt cttcgggccc cctgaactgt gttcatggag    1800
catctggctg ggtaggcaca tgctgggctt gaatccaggg gggactgaat cctcagctta    1860
cggacctggg cccatctgtt tctggagggc tccagtcttc cttgtcctgt cttggagtcc    1920
ccaagaagga atcacagggg aggaaccaga taccagccat gaccccaggc tccaccaagc    1980
atcttcatgt cccctgctc atccccac ccccccacc cagagttgct catcctgcca    2040
gggctggctg tgcccacccc aaggctgccc tcctggggc cccagaactg cctgatcgtg    2100
ccgtggccca gttttgtggc atctgcagca acacaagaga gaggacaatg tcctcctctt    2160
gacccgctgt cacctaacca gactcgggcc ctgcacctct caggcacttc tggaaaatga    2220
ctgaggcaga ttcttcctga agcccattct ccatggggca acaaggacac ctattctgtc    2280
cttgtccttc catcgctgcc ccagaaagcc tcacatatct ccgtttagaa tcaggtccct    2340
tctccccaga tgaagaggag ggtctctgct ttgttttctc tatctcctcc tcagacttga    2400
ccaggcccag caggccccag aagaccatta ccctatatcc cttctcctcc ctagtcacat    2460
ggccataggc ctgctgatgg ctcaggaagg ccattgcaag gactcctcag ctatgggaga    2520
ggaagcacat cacccattga cccccgcaac ccctcccttt cctcctctga gtcccgactg    2580
gggccacatg cagcctgact tctttgtgcc tgttgctgtc cctgcagtct tcagagggcc    2640
accgcagctc cagtgccacg gcaggaggct gttcctgaat agccctgtg gtaagggcca    2700 ggagagtcct tccatcctcc aaggccctgc taaaggacac agcagccagg aagtcccctg    2760
ggcccctagc tgaaggacag cctgctccct ccgtctctac caggaatggc cttgtcctat    2820
ggaaggcact gccccatccc aaactaatct aggaatcact gtctaaccac tcactgtcat    2880
gaatgtgtac ttaaaggatg aggttgagtc ataccaaata gtgatttcga tagttcaaaa    2940
tggtgaaatt agcaattcta catgattcag tctaatcaat ggataccgac tgtttcccac    3000
acaagtctcc tgttctctta agcttactca ctgacagcct ttcactctcc acaaatacat    3060
taaagatatg gccatcacca agcccctag gatgacacca gacctgagag tctgaagacc    3120
tggatccaag ttctgacttt tcccctgac agctgtgtga ccttcgtgaa gtcgccaaac    3180
ctctctgagc cccagtcatt gctagtaaga cctgcctttg agttggtatg atgttcaagt    3240
tagataacaa aatgttttata cccattagaa cagagaataa atagaactac atttcttgca    3300
```

<210> SEQ ID NO 14
<211> LENGTH: 20000
<212> TYPE: DNA
<213> ORGANISM: Macaca mulatta

<400> SEQUENCE: 14

```
aacatgaaca tggtggcctt gtcagaaagc aagtgtgtgt tgctgaaaca tcagcagaga    60
ttgtcaaagg gataaagaga taacttaaaa gggttcctac tgaccaaaat gagacaagtt   120
ggccatctaa aatcaaatca taattatagt tcaataggac acatttcgtc tcttaaatct   180
tccaatccat aatgaccatc atggcccata acctcaaaag agtaaagtta aaataaagtt   240
cagaaaaggt tagttgcaat aaaacattag ttttattaat tttaacaaga aggggatgaa   300
gctatagatg catttttttt ccttctttta actatgttgc cccttacaag gtacagcttt   360
gccttatttt tctctgtctg agtaaggata aagagtaaag gccgggcatg gtggctcaca   420
cctgtaattc cagcgctttg ggaggccgag gcaggaggat cacttgaggc caggagtttg   480
agaccagcgt ggccaacatg atgaaatctc gccactacta aaaatataaa aattagttgg   540
aaatggtagc gcatgcctgt aatgccagct actctggagg ctgaggcaca agaatcactt   600
gcaattccgg aattcaggag gtggagtttg cagtaagcca agattgcgcc actgtaactc   660
cagcctgggt gactgagtga gactctgtct caaaaaaaga agaataaaaa caagaagttg   720
tgagtaggcc aaatagttcc agaaaaagca gaaatccacc accccccga cacacaggaa   780 gcggctcagg aggtgacgca gagaaggaaa gtgtgtctgc tggggttttg caagttggtt   840
aatttgaaag atccctcaag gaggtaaaca aatggtgcaa acttcattca ttcatctcct   900
ggaagataaa cttcgaacac ccaactaacc ccaccaatta aatgagttaa aggaagacag   960
acacaagtgt caattatgct aacagagctc tgtgttaaat accccaccag catcgcctca  1020
tttaagcctc acaactatgt gggaaagaga cttttatccc cattttacag ataaggaaac  1080
caattctcag agaactgagg ccctccccca gatccaagtc cgcttagctc cagtcacccc  1140
acgtcctctg catgtcacag gtgctcagaa agatgcagat gcaccttcag gaagccaaaa  1200
tgagcagagc ccctaaagag cggattgacg gcctctttct ggaaaaaatg gaagtttgaa  1260
tctgaggagg tatccctcaa caacaggtgc tgctcaccaa gtctggggcc aaacgcagca  1320
gctgttctcc cacttagacc cctgagacct gtctataagg tttttcagag cgaggacaca  1380
tccccaaagg ttgtggcttc tggtggttag cattgacttg gggcccatcc catgccagag  1440
gctgcccgaa gtgcttaaat gttattacct catttgatct tcacaatcct aacggaagtg  1500
actcttctaa gagtctccct atctcacaga tgagggaacc gaggcacaga gaggttaagt  1560
ggcttgtcta agagctcaca gaaagagcgg tggagctaag gcttgacccc agatgttaga  1620
tcctgagccc atgctttaac cagtgacctg cactgcctcc caaagaagga agctggtgcc  1680
tgggagggag ggtgcagagc gagggtgtgc atggtgcatg tgtgtgtttg tggggtggcc  1740
agcactcttc ggggcacttt gccaatgagt tcagctcccc tgaagtccac tgttgctctc  1800
ctgaccagtc actcagtctg gatttacttg gcccaaggcc attggcacca gcctggccaa  1860
cattgtggcc aggcttaccc ccttacccgc ttccttgctg cagaccccaa atcttgactc  1920
ctacatccct atccagccta caccacgagg ctccccatctc cgggcagggc cctgtgatgg  1980
gtcagggcct cccagatgc cccttgttca ttaccagctc acaggatctt cccatgacgc  2040
atttcctctg aggggatcag cccagatgct gcaatagaca attctggaag taaccgagtg  2100
gacaagactt tccccatcgt gtcctggggt tcctggggtc acagtgtcct tgtgaatggc  2160
cactgagtgc tcccacctcc ccttaccgcc cggggttttg tcctggtgca ttttcccaga  2220
tcatcccagc ccttcctccc aggatggatg tccagagcag ggcaagggct gagcctagag  2280
ccctggaacc aaaagaacag gacccccaaat tctgagcccc ttacttgccc cacctgctcc  2340
cacccatgct ttcttcattc ctcctccaaa tgccccagct ccccactgca atcccttctg  2400
```

```
cacccagcca ggtcctatga cacacacctc cccagtgcac acagacctgc ccagccgcag    2460
ggctgcccac tgggcatgtc ataggtggct cagtcctctt ccctctgcaa ctggcccag    2520 aaacctgcca gatgttggtg ccaggtctgt gccagaaggg caaggcctgt catttctagt    2580
aatcctctgg gcagtgtgac tgcacctttt acggcagctc aaagggagag ggtgactcgt    2640
cctgggtcac agagctgaca gggcgggtag aacaggtgat atgcagggct ttctgagttt    2700
atgagggccc agtcttgtgt ctgcctggca atgggcaagg cccctttcctg cccaagctcc    2760 ccgcccctcc ccaacctatt gcctccgcca cccgccaccc gaggccaact tcctgggtgg    2820
gcaggaactg ggcctgtgc ccagggcgtg cactgcctcc acgcagcaac cctcagagta    2880
ctgagctgag caaaggagga ggaggggatc agcactctga ggaaggccta gccactgctg    2940
ctgccaggaa ttccaggtag gagggcggc aaccttctgc cagcccccag gccactctcc    3000
tgtgcctgcc agaggagacg gagcttgagg agagcaggaa aggtggaaca atgctgctgc    3060
tgctcactct gttccacaga tgggaggac agtggggctt ggagtggggg tcatggcaca    3120
gatgggaaaa tgaaggctca gagaggggaa gaaatgccca ggaggtaccg agggcaggcg    3180
acctcaacca cagcccagca ctggagctgt gagtagacgt agagtagcag aatatccatt    3240
cagccagctc aggggaagga caggggccct gaagccaagg catggagctg gcagggaaga    3300
gagctcagag agaaggggag gggagtctga gctcagtttc ccactgcctg aaaagagggt    3360
ggtacctact cccctcacag ggtaactgaa tgagactgcc tggaggaaag ctcttcaaat    3420
gtggcccacc ccaccccagt gacccctgac atggggggagg aaggacagca tcagaaggga    3480 cttttccgggc acacccagca cccagctctg agctgtcctt gaactgttgc attttaatcc    3540
tcacagcagc tcaacaaggt acataccgtc accgtcccca ttttacagat ggggaaattg    3600
aggctcagag cagttaaaca actcacctga ggcctcacag ccagttaagt gggttccctg    3660
gtctgaatat gtgtgctgga ggatcctgtg ggtcactcgc ctggtagagc cccaaggtgg    3720
aggcataagt gggactggtg aatgacagaa ggggcaaaaa acacactcat ccattaattc    3780
tggaagtatc cacggcacgt acgccagctc ccaagcaagt ttgcacattg cacaaagggt    3840
gatgcaatct gatttaggct tttaaaggga ttgcaatcaa gtggggccct actggcctca    3900
accctgtacc accctcccct tccatcccca gtagtcccca aagacctcca tcaaccccag    3960
gatggggccc gtattcccaa agaaaatcca agctgtatac gcatcacact gattttccag    4020
gagcagaaac agaaacaggc ctgaggctgg tcagaattga accccctcct gctctgagca    4080
gcctgcgggg caggctaagc agagggctgt gcagacccac ataaagagtc tactgtgtgc    4140
caggcacttc acccaaggca cttcacaagc atgcttggga atgagacttc caactctcta    4200
ggatgcaggt gaaacacttc ctggttcaaa caggtgaagc ggcctgcctg agacagcatc    4260
acgcttcttt acaggtttgc tctcccacct ctaccctgtc tcatggtccc ccatgccggc    4320
ctgacgcttg tgtctgcctc agtcatgctc catttttcca tccggacaat caagagggtt    4380
tttgtgtcta aggctgactg ggtaacttcg gatgagcggc ctctctgctc tgagcctcag    4440
tttcctcatc tgtcaaatgg gctctaaccc actctgatct cccagggcgg catcagtctt    4500
cagcatcagg catttcgggg tgaattagta aatggtagat cttgctacca gtggaacagc    4560
cgctaaggat tctgcagtga gagcagaggg ccagcaaagt ggtactctcc cagcgactgg    4620
ctgactcacg ccaccccctc cacccttggac gcaggacact gtggtttctg agccaggtac    4680
aatgactcct tttggtacgt gcagtggagg ctgtatgctg ctcaggcaga gcgtccggac    4740
```

```
agcgtgggcg ggcgactcag cgcccagcct gtgaacttag tccctgtttg ctcctccggt    4800
aactggggtg atcttggtta atattcacca gcagcctccc ccgttgcccc tctgcaccca    4860
ctgcttaaat acggacaagg acagggctct gtctcctcag cctcaggcac caccactgac    4920
ctgggacggt gaatcgtaag tatgcctttc actgcgagag gttctggaga ggcttctgag    4980
tcccccacgg cccaggcagg cagcaggtct ggggcaggag gggggttgtg gagcgggtat    5040
ccgcccgctg aggtgccggg cagatggagg ggctgcagct gggctcctat tgtcgtaata    5100
acagcagcca tgagggttgt gtcctgcttc ccagtcctgc ccggtcccca ctcagtacct    5160
actggtggat acactggctt ttgtaagcag aagtgcacga gggtgtctag ctccgcggtc    5220
ctggcacccc aagatacagc aacagcaagg aagcgcagcc atttcttcct gtttgtgcag    5280
ctcctgtgtc tgtcaggggg ttcctatctg ttgtctcctg taagcctcac cacctctcct    5340
actacttgga cacgcatctt tttcccttc tatggatgag gaggttaagg ttcagggagg    5400
ggtgaggagg aacgccggct cacattctcc atccctcca gatacggcca ggaacagacc    5460
tgtgccaggt ctcagcctta catcaagatg gtctccccc tgcactgtgg acctctgggc    5520
cctcctgtcc cagtggagga caggaagctg tgaggggcac cgtcacccag ggttcaagct    5580
ggcattcctg aataatcgct ctgtgccagg ccacggctaa gctctgtgca cgattaagcc    5640
tcataaccct ccaaggcagt taccagggtg attcccattt tacagatgag gaagttgggg    5700
accgagtggt taataactgg ccccaaatca cacaccatcc ataatttggg ctcaggcacc    5760
tggctccagg ccccgaaatc ctgagcctgg ccctagtgct caccgtttct ctcaggtctc    5820
aggcgctgga tggggaacag gaagcctggg ctggacttga ggcctctctg atgctcggtg    5880
acttcagaca gttgctcaac ctctctgttc tcttgggcaa acatgataa cctttgacct    5940 ctgtcccctc ccctcacccc acccgacctt gatctctgga gtgttggaag aatttaattt    6000
ttcctgcact gagtttggag acaggggtca aaaagctgac caaggccaag ctggccagtt    6060
tcccatagaa cgcctctaaa agacctgcag cactagcagc aagaactggt attcttgaga    6120
acttactgtg caccaggcac ttcttggtat tttgtgcata tttaatttca caataactct    6180
atgacaaagt ccacctttct catctccagg aaactgaggt tcagagaggt taagtaacgt    6240
gtccaaggtc acacagttaa tagcaagttg atctggagca atctggcctg agagcctcta    6300
attctagcca caaactgagg ctgccctct tcatttagcc aggccacctc tgaaatcttc    6360
tggttcaaga cttctggctc cagctttgta cacagagact attaaatgtc aggttttgca    6420
gtcacatctg tttaatccca gacaaaacat ctgggattaa atctcagttt tgtaagcaag    6480
tagctctgtg attttagtg agttatttaa tcctctttgg cctcaatttt tctgtctata    6540
aaatagggtt aatcatttgc acctcatagg gtaagctttg aggacagatt agatgataca    6600
gtgcctgtaa atcgcctggt gttagtaagt gtggcaatga tggtgacact gaggttgatg    6660
tttgcttagc ataggttagg cagctagcag gcagtaaaca aatacttgga gaatttaatg    6720
gaaaattggc caaactcaga tgctgttcac tgctgagcag gagccccctc ctgctgaaat    6780
gggtcctggg gagcgcagca gctggcagga agaaatctgc catctctcgg gcaggagctc    6840
aacctctgtg caggcacagg gacggcttcc gcacctggtg cccactcacg cattacgtca    6900
gttattcctc atctctctcc aagggattct tttctccact gtatagctct gaagccaatg    6960
ctcacagaag tgaagtcatt taccccgggc cccctgccag taagtgacag ggcctggtca    7020
cacttgggtt tatttattgc ccatttcaac aggtcgtttg accataggcg agattctctt    7080
ccctgcaccc tgctgggttg ctcttggtcc cttatttat gctcccgggt agaaatggtg    7140
```

-continued

```
tgagattagg caggaagtgg cttgcttccc tctccctggc cctgcaaagg gtgctcccac    7200
ctgccccagt tccagaaatg tcaccatgaa gtcttcattc ttctgtttta aagcttggcc    7260
tcagtgtcca tacaccatgg ggtacttgac catctacttt ctcctctcca gccgccctcc    7320
caggcactag cttttgaggg tgcagggtgc tgcctctgat agaagggccg ggagagagca    7380
ggttttggag tcctgatgct atgaggaaca gcttgggagg cataatgaac ccaacacgat    7440
gcttgagacc aatgtcagag cccaattctg ccattcatca tctgagattt gagggcacag    7500
ctgtctcagt ccgtgatctg agtgctggga aagccaagac ttgttccagc tttgtcacca    7560
acttgctgta tggcctcgac aaggccctga ccctctctgg gcttcaaact cttcactgtg    7620
aaaggaggaa accagaggag gtgatgtgac gccagaaaag atggatgggt gtgggaatt    7680 gtgctcctcc cagctgtcac cccctctcca ccctcccctgc accagcctcg ccacctcctt    7740
cgagcccagc agcctcctgt ctaggagggt gcctcttctc catctgtttt gctacatcga    7800
acccagatgc cattctaacc aagaatcctg gctgggtgca gtgacactca cctgtaaccc    7860
cagcactttg ggaggccgag gcaggcggat caagaggtca ggatttcaag acctgcctgg    7920
ccaacatggt gaaatctcgt ctctactaaa aatacaaaaa ttagccagat gtggtggcat    7980
gtgcctgtaa tcccagctac ttgggaaact gaggcaggag aactgcttga acctgggagg    8040
cagaggtttc agtgagccaa gatcacacca ctgcactcta gcctggggga taaagcgaga    8100
ctctgtctca aaaaaaaaaa aaaaaaaat cctatgttag cgtacagagg tccccagtga    8160
ggtcttctcc cagccccact ttgcacaact ggggagagtg aggccccagg accagaggat    8220
gcttactcaa ggccaaacgg atagtgatgg ccctgccagg actagaagcc acaacttctg    8280
gccctaaggc cactcagcgt atttagtgtc cccaccctgc agaggcccaa ctccctcctg    8340
ccctctgagc tctgtaatga tgggggaatt tccataaacc atgaaggact gcacaaaatc    8400
cagctgggaa gtgaaagaga aacctaaggg agatggaaat atacagcact aattttagca    8460
ccgtcttcag ttctaacaac actagctagt tgaagaaaaa tacaaacatg tattatgtag    8520
tgtgtggtcc gttccatttg gattacttag aggcaagagg gccaggagaa aggtggtaga    8580
gagaaaccag ctttaggctt cattttgttg ctttactgga aagaaacttt taacagtcca    8640 gggggtcaa tgaatctcaa tatttgttat ttccaacttt tttctccagt gtttcatttc    8700
ccaaattcaa ggacacattt ttctttgtat tttgttaaga tgatgatttt acttttgtga    8760
ctagtagtta actatgtggc tgccaggcat attctcctca gctaggacct cagttttccc    8820
atctgtgtag acagcaggtt ctacttaggg ggctgcagat tgatggtccg aagtctgggc    8880
atatctggag tagaaggagc actgtggggc atggcaggct ctgcgttgct gtggatgaca    8940
ctgactttga ccattgctca gcagagcctg ctctcgccgg ttcagccaca ggccccacca    9000
ctccctattg tctcagcccc agctatgaaa catgtattcc tcactggact atcacctgaa    9060
ggctttgaat ttgcaacacc tgtcaacccc tccctcaaaa gggttgccct ctcagatcct    9120
tttgatgtaa ggtttggtgt ctagacttat ttcactaaat tcttccaaca gcctcacttt    9180
atgtatgagg caaatgaggc accagggaga taaatgacgt gtcctggctc atacacctgg    9240
aaagtgacag agtcagatta gatcccaggt ctatctgaag ctaaaagaga tgcttttca    9300 cttcccacca cgcccatctc ctttaaagca gcacaaagcc ttgcttcaca ggagagatga    9360
gcttctctaa agtccctgac agcaagagcc cagaactggg acaccattgg tgatccagat    9420
ggcaggtgag ctgactgcag ggacatcagc ctattcttgt ggctgggacc acagagcatt    9480
```

```
gtggggacag ccccctctct taggaaaaaa ccctaagggc tgaggatcct tgtgagtgtt    9540
gggagggaac agctcccagg ggatttaatc acagccccac catgctctag ctggtgccat    9600
tgtgcaagat gcatttccct tctgtgcagc agtgtccctg ccactcaac  agtgggatta    9660 gatagaagcc ctccaagggc ttctagcttg acgtgattct tcattctgat ctggcccgat    9720
tcctggataa tcgtggccag gcccattcct cttcttatgc ctcatttgct tcttttgtaa    9780
aacagtggct gtaccacttg catcttaggg tcattgcaga tgtaagtgga gctgtccaga    9840
gcctgggcgc aggacctaga tgtaggattc tggttctgct actttacttc ctcagtgaca    9900
ttgaataggt gacctaatct ctctggtttt ggtttcttca tctgaaaaag aaggatagta    9960
gcatcagcac ctcacaggat tgttacaaga aagcaatgag ttaacacatg tgcgcacgta   10020
gaacagtgct tggcatatgg taagcactac atacattttg ctattcttct gattctttca   10080
gtgttactga tgtcagcaag tacttggcac aggctggttt aataagcctt aggcacttcc   10140
acgtggtgtc aatcccgggt cactgggagt catcatgtgc cctgactcgg ggcctggccc   10200
ccgtctctgt cttgcaggac aatgccatct tctgtctcat ggggcgtcct cctgctggca   10260
ggcctgtgct gcctgctccc cggctctctg gctgaggatc cccagggaga tgctgcccag   10320
aagacggata catcccacca tgatcaggac cacccaaccc tcaacaagat cacccccagc   10380
ctggctgagt tcggcttcag cctataccgc cagctggcac accagtccaa cagcaccaat   10440
atcttcttct ccccagtgag catcgctaca gcctttgcaa tgctctccct ggggaccaag   10500
gctgacactc acagtgaaat cctggagggc ctgaatttca acgtcacgga gattccggag   10560
gctcaggtcc atgaaggctt ccaggaactc ctccataccc tcaacaagcc agacagccag   10620
ctccagctga ccaccggcaa cggcctgttc ctcaacaaga gcctgaaggt agtggataag   10680 ttttggagg atgtcaaaaa actgtaccac tcagaagcct tctctgtcaa ctttgaggac   10740
accgaagagg ccaagaaaca gatcaacaat tacgtggaga aggaaactca agggaaaatt   10800
gtggatttgg tcaaggagct tgacagagac acagttttg  ctctggtgaa ttacatcttc   10860
tttaaaggta aggttgcaaa accagcctga gctgttccca tagaaacaac caaaaatatt   10920
ctcaaaccat catctcttga actctccttg gcaatgcatt atgggctata gaaatgcatg   10980
tcagtgtggg ctcttcaatt ttctacacac aaacactaaa atgttttcca tcattgagta   11040
atttgaggga ataatagatt aaattgtcaa aaccgctgac agctctgcag aactttccag   11100
agcctttaat gtccttgtgt gtactgtgta cgtagaatat ataatgctta gaactataga   11160
acaaattgta atatactgca taaagggata gtttcatgga acgtacttta gacgactcta   11220
gtgtcccaga atcagtatca gttttgcagt ctgaaagacc tgggttcaaa tcccgcctct   11280
accactatta gcttttgaca ccgaacaatg cattctacct ccttgaggtg ctaatttccc   11340
atcttagcat ggacaaaata gtttttttta ggattaaaca agtgacaaac accttgggaa   11400
aagtgtggca tacagtaggt ggtgggctcc tctgtatctc aggctgcctt cctgcccctg   11460 agggggtgctc ttgaggcaaa ggagggcagt ggagagcagc aggctgcag  tcagcacaac   11520 tggggtcctg gctctgctgt ggcttagggc aggccccggt ccctctccag ccccagtctc   11580
ctccttctgt ccaatgagaa agctgggatc ggggtccctg aggcccctgt ccactctgca   11640
tgcctcgatg gtgaagctct cttggcatgg cagaggggag gctgctcagg catctgcatt   11700
tcccctgcca atccagggga taaagaaaac cctcaggaat agtaagcaga atgtttgccc   11760
tgaatgaata actgagctgc caattaacaa gaggcaggga gccttagaca ggaggtaaca   11820
aatatgcctg atgctccaac attttatttg taatatccaa gacaccctca aataaacata   11880
```

```
cgattccaat aaaatgcaca gtcaggatgg catctcttag ccttacatct ctgcgatgta   11940
gaaattctgc atcttcctct agttttgaat tatctccaca cagaccttt tggcagcctg    12000 gatggttggt ttcagcacct tttgcagatg atgaagctga ggcttgaggg atgtgtgtcg   12060
tcaagggggt tcagggcttc tcagggaggg gactgatggc tcctttattc tgccacactc   12120
ttccaaacct tcacccaccc ctactgatgc ccgccttacc ctctctgtcc aggcaaatgg   12180
gagagaccct ttgacgttga ggccaccaag gaagaggact tccacgtgga ccaggcgacc   12240
accgtgaagg tgcccatgat gaggcgttta ggcatgttta acatctacca ctgtgagaag   12300
ctgtccagct gggtgctgct gatgaaatac ctgggcaatg ccaccgccat cttcttcctg   12360
cctgatgagg ggaaactgca gcacctggaa aatgaactca cccatgatat catcaccaag   12420
ttcctggaaa atgaaaacag caggtgattc cccaacctga gggtgaccaa gaagctgccc   12480
acacctctta gccacgttgg gactgaggcc cgtcagaact gaccagaggg ttggagaggg   12540
tgaacactac atccctgggt cactgctact ctgcataaac ttggcttcca gaatgaggcc   12600
accactgagt tcaggtggca ccggccatgc tccatgagca ggacagtacc caggggtgac   12660
gaggtaaagg tctcgtcctt ggggacttcc cactccagcg tggacactgt cccttcccaa   12720
tatccagtgc ccaggacagg gacagcagca ccaccacacg ttctggcaga accaaaaggg   12780
aacagatggg cttcctggca aaggcagtag tggagtgtgg agttcaaggg tagactgtcc   12840
ctgtggggat gggggaagag cctgtgtggc taggcccaga aaagcaaggt tcaaaattgg   12900
aatagccagg gcatgttagc aaaaggcttg agtttctctg tcactttatc ggtgctgtta   12960
gattgggtgc cctgtagtaa atgatactcc aatatgagtc acacattagt gtgtctgtgt   13020
gcattcgtaa ttatgcccat gccctcctat ctagtttatt ttgtacactg taaaaccaag   13080
atgaaaatac aaaaggtgtt gggttcataa taggaattga ggctggaatt tctttgtttc   13140
acgccagcac ctcctgaggt ccctgctcca ggggttgaga agaacaaggg aggctgagag   13200
ggtaactgat cagagagccc aaagccaggc tgcccgctca ccagacccc tgctcgggg    13260 ggctctgtct ccccatggaa aacaagaggg gagcactcag cctggtgtgg tcagtcttct   13320
gggggcactg ctaccagccc atgttcctct gggtatagga ccctggggat gtttcaggct   13380
gggggcccag tgaccaaaca ctacagggca ggatgagaca tgcttccagt acacctagaa   13440
tctcagagga ggtggcattt caagctttca tgattcattt tgatgttaaca ttctttgact   13500 cagtgtagaa gagctaatag tagaacaaac caaagccaag ttcccatgtt agagtgggtg   13560
gaggacacag gagtaagtgg cagaaataat cagaaaagaa aacacttgca ctgcggtggg   13620
tcccagaaga acaagaggaa tgctgtgcca tgccctgaat ttcttttctg catggcaggt   13680
ctgccaactt acatttaccc agactggcca ttactgaaac ctatgatctg aagacagtcc   13740
tgggccacct gggtatcact aaggtcttca gcaatggggc tgacctctcg gggatcacgg   13800
aggaggcacc cctgaagctc tccaaggtga gatcaccctg atgaccctgt gcacccgg    13860 gatctgtagg gaaggatgta tgggggctgc agttctgtcc tgaggctgag aaggggcca   13920 agggaaacaa atgaagaccg aggctgagct cctgaggatg cccgtgattc actgacgcgg   13980
gacgtggtca gacggcaaag ccaggcaggg gcctgctgtg ctgctggcac tttcagggcc   14040
tcccttgagg ttgtgtcacc gaccccgaat ttcatctttg cccaggacct tctagacatt   14100
gggccttgat ttatccatat tgacacagaa aggtttgggc taagttgttt caaaggactt   14160
tgtgactcct tcgatctgtg agatttggtg tctgaatgaa tgaatgatgt cagctaaaga   14220
```

```
tgactcttcc tttggaaaac taaaggtgac caaagaacaa ctgcagttcc gtgaacggct    14280
gcgttgtctt gggatctggg cactgtgaag gtcactgtca gggtccatgt cctcgaggag    14340
cttcaagctg tgtgctagaa aggagagagc cctggagaca ggcgtggagt ggcgatgctc    14400 tttcccttc tgagttgtgg gtgcaccctg agcaggggca taggcgcttg tcaggaagat    14460
agacagaggg gagccagccc tgtcagccaa agccttgagg aggagcaagg tctgtgtgac    14520
agggagggag aggatgtgca gggccagggc tgtgcagcgg gagaaaggcc tgagtgaaca    14580
cttcctggga ggtgtccacg tgagccttgc tccaggcctg ggctgggca caactcagcc    14640 ttagaacatg tctctgcttc tctcccttcc aggccgtgca taaggctgtg ctgaccatcg    14700
atgagaaagg gactgaagct gctggggcca tgtttttaga ggccataccc atgtctattc    14760
cccccgaggt caagttcaac aaacccttg tcttcttaat gattgaacaa ataccaagt    14820 ctcccctctt catgggaaaa gtggtgaatc ccacccagaa ataactgcct gtcactcctc    14880
agcccctccc ctccatccct ggccccctcc ctgaatgaca ttaaagaagg gttgagctgg    14940
tccctgcctg cgtgtgtgac tgcaaacccc tccatgttg tctctgggtc ttcctttgcc    15000
tgctgaggcc gtgtgtgggc tccaggtcac agtgctctct ccggacccc tcaactgtgt    15060 tcatggagca tctggctggg caggcatatg ctgggccagg atggaggggg ctgaatcctc    15120
agcttacgga cctgggccca tctgtttctg gagagctcca gtcttccttg tcctgtcttg    15180
gagtccctaa taaggaatca caggggagga atcagatacc agcccatgac cccaggctcc    15240
tccaagcatc ttcatgtccc cctgctcatc ccccactccc cgccacccag agttcctcat    15300
cctgccaggg ctgcctgtgc caccccaag gctgccctcc tggagcccg agaactgcct    15360 gaccatgccc tagccctgtt ttgtggcatc tgcaacaaca aaagagagag gaccgtgtcc    15420
tcttcttgtc ccactgtcac ctaaccaggc ttgggcccgg cgcctcttgg gcacttctgg    15480
aaaacaactg aagcagattc ctcctgaagc ccattctcca tggggcgaca aggacaccta    15540
ttctgccctt gtccttccat cgctgcccca taaagcctca catgtctcag tttagaatca    15600
ggtcccttct cctcagatga agaggagggt ctctgcttct ttttctctat ctcctcctca    15660
gactcaacca ggcccagcag tccccacaag accattaccc tatatccctt ctcctcccta    15720
gtcatgtggc cataggcctg ctgatggctc acgaaggcca tcgcaaggat tccccagcta    15780
tgggagagga agcacagcac ccactgaccc ctgcaacccc tctctttctc ccctgagtcc    15840
tgactggggc cacatgaagc ctgacttctt tgtgcctgtt gctgtccctg cagtcttcag    15900
agggcagccg cagctccagt gccatggaag gaggctgttc cggaatagcc cttgtggtaa    15960
gggccaggag agtccttcca tcctccaagg ctctgctaaa gggcacagca gccaggaggt    16020
cccctgagcc cccagctgaa ggacaggctg ctccctctgt ctctaccagg aattgccttg    16080
tcctgtggaa ggcactgacc catcccaaac taatcttgga atccctgtct aaccactcac    16140
tgtcatgaat gtgtgcttaa aggatgaggt tgagtcaaac caaatagtga tttttgtagt    16200
tcaaaatggt gaaattagca attcaacatg attcagccta atcaatggat accaactgtt    16260
tcccacacaa gtctcctgtt ctcttaagct tactcagtga cagccttca ctctccacaa    16320 atacattaaa gatatgaccg tcaccaagcc tcctaggatg acaccagacc tgagagtctg    16380
aagaccggta tcccctgcc agctgtgtga ccttcatgaa gtcgccaaac ctttctgagc    16440
cacagccgtg gccagtaaga cctgcctttg agttggtacg atgttcaagt cagataataa    16500
aacaccgttt acacctatta gagcagagaa taaatagagc tacatttctt gcatttatga    16560
gctttctgtg aatcagacat ccctgtgaag aacctccctg gctatttctc atttaataac    16620
```

```
tgtagcagca ctgtgatgtg tgagtagatc cgctgtgctc ttaaactcca aatctacata    16680
tgaggaaact gaggctcaga gaggctgctg gtctcccaca atgtcacata gttcataagt    16740
ggcaaagctg gcttgatggg ctactcgttc ctctgaacca caccacctca ccacactctc    16800
cccttcgagg gtcatgctaa acttctgcag agctaattcc tccttaaacc ataagggttg    16860
ctggtggccc acagctcacg cctagcacgc ttcatgagaa aaacgccctc cacccaatgt    16920
ggagcaggcc ctgagctgaa ggtggtgagc agaagctcat ccaccagatg ttgacacagc    16980
ccgcggcctt gggcgaccca caggactcct cttatttaac tggcatttgg taggagaaca    17040
ggggcagagt caaagacaag tgggctttcc ggagcagcca ggacagggaa ggaggctgca    17100
gtgctgaggg catcacctta gacaccatcg ttttactttg aagaatcgtc tgtcacacac    17160
gagttgacag tccggttggg agagactcca ttcaaaccag cataagctcc cagaggaatt    17220
cctgggctcc tgtgggaatc aacagggatc agtcaggggt gggcagagtg tcatgacaac    17280
ctcattagga ggaagacaaa tacatgtcac aagtccgtga ggcaacagcc ataagacctc    17340
agcttcactg tatcttccag agttttttaa aaaatgcatt cactgtctaa tgtgatcctc    17400
cagacaggtc ctgcaggact cagcctagga atcattatcc ccaaagtaca catggggaaa    17460
ctgaggccca gcaggtcaaa tgctctgtcc agtgtgggcc tggaaggcag gacttctccg    17520
ctcttaggcc tggctgtccc caactgcaca cacttcctca gtccatatgg gatcacgata    17580
aaaactccat cctccagaac cgcactgcgt caacctgctg tgctctaaca acagctgaag    17640
gccgagctgc ggggcatcct gggtgttccg agtcagtttc ccactgcagg caggaacctc    17700
atcctgctct gaaacagatg agagggaaac acggaaaaca gctgcgagct cagccgggaa    17760
cctcagagtc atgacctttt accccaccta ggagtttgca ggggacagaa cacacgaatt    17820
tgagatttta agcctaaaca aaggaagcct tggtttgaag tgcaagctct gccagacaga    17880
gggcaccctg tgagccccat tgttaagag gacgatagtc agggagcttc taggttctca    17940
caccagaaat gggaaataca gattatacat tgatctcctt cccaggagca acttgatcct    18000
cccataaatc cgagcaggca gcatttattc aaacaacaaa caagcaaaca ggagctgcgt    18060
atgggggata gagagatgaa acccaggtcc gtccctggga gagtgctgat ctacggcggt    18120
ggggaacggt gaataaacga ggcgtgcgtc catggatctg ggtggagagg gtcagggtgc    18180
agcccgggac ctttccagag gcgtaagaaa tgatcagtat acacccgcag atgacctcaa    18240
acaccccaag ggctccttga aaggctgagg cctttgtgtt gttcttggtt ggaaaattca    18300
caggcagtgg agtgaacaag gcacacggca ggactcagag ccaggacag cttctgcagg     18360 aacccggctc agttctaaaa ggacaaatgg aatgaccctg agtaaagaag tcagagaagg    18420
gcaccctcac tgaggcaaac tccctcccca gcagggaccc agcagcaacc caaaaaagca    18480
ggagtctcac ttcatcatca tatgggagag ggcaggctgt gtgatctcag ggaagttcct    18540
caacttctct gtgccatagt ttcctcatct gcaaaatgta aatcgaattt gaggtctcga    18600
tgaaatgtct tatttctcta aagtcccttg tccttgtccc atgcagccta gaaatcttcc    18660
tctggcctag ttgtggagcc aaggatagac cgggcctgaa tcttacattg ctggagatgg    18720
tgaagctgac cagcatgaga ggtcaggttt tagaagccca aatcccagca ggcataagcc    18780
tcaccctcca atatcagctt tatcagaaac aaaaaaataa catgtcatat ccatttgccc    18840
ttttccttaa atgagtagca cttgggcagg gcagaggggc tgattatcca agctgggaag    18900
acgctgacag cagacgcttc aatggcagtc taggagtttt ctgataactg tcattggtat    18960
```

```
cacacttact attgaaatcg tgacatcagg aatgatgaaa ggaactagag tcacatggtc    19020
tggagcaggg aagtgaggag ctgaaacctc cttcaacctg gttgctgtgt ccccagggtg    19080
ggtaaagccc ctctgttcat cccacatgga acaaatagag tggaatcagt ccttgctaaa    19140
gggttgaaga actgagctgt gagcttcttg attgctgcag cacaatcctt gcccatcctg    19200
actgatataa ccagaattcg tgaaatgcat caaataagtc ttcaactact atgcaagcct    19260
gggagggtga ctaagatctg aaaaacacaa ggaaagctaa aggaattccc acaaggaaac    19320
tccattagaa agttctagtt acaaggtact cagcacaggc catgcagaaa taagcccaga    19380
tccggtggtg agcaggaaag ggtggggatg tgagtgctga gccacacagg agagagtaat    19440
agaggctcaa gccagcaagg ggacggccac caccccacgc agtgttggcc aacagtttcc    19500
ggggcatttg ctctcagaag tcaaagctga ttttccagaa ttgaagtgct cattgtttgg    19560
gatgatttag gaacaacatc agcaaaaacg aatgaacaat cagggctaat agaattgtgt    19620
ttaaactctg ttgggcttcc ttgacagagg gcacggggag caaaaaaagt cagcagtgtg    19680
tattaagtaa aaaaactttt tttcccttt aattggcagt taatacccctc aaaatatgtt    19740 ctgagattga tcaagtaagt gtccttcggc attaaaatat taggatgcaa ttgctaaggg    19800
cttcttagca aagttgaaag aacacaggaa tcccaactcc actgtctcct tagcatgcaa    19860
tcctgagtgg gctgttacag ctgtctgtgc ctcagcgccc tcacctgcaa gacaggtaaa    19920 ataaaccta actcctaggt tacttttgtg gattaatgtg caaagcgtca ccctaaaaaa    19980
gtgctgctac ttaaatgacc                                                20000
```

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 20
tggtgctgtt ggactggtgt                                              20

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21
gatattggtg ctgttggact                                              20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
ggctgtagcg atgctcactg                                              20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
gggtttgttg aacttgacct                                              20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24 ccactttcc catgaagagg                                               20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
ttgggtggga ttcaccactt                                              20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
ctttaatgtc atccagggag                                              20

<210> SEQ ID NO 27
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 27
tctttaatgt catccaggga                                          20

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
ttctttaatg tcatccaggg                                          20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
cttctttaat gtcatccagg                                          20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
ccttctttaa tgtcatccag                                          20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
cccttcttta atgtcatcca                                          20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
acccttcttt aatgtcatcc                                          20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
```
tcaacccttc tttaatgtca                                               20

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34 ctcaacccttt ctttaatgtc                                              20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
gctcaaccct tctttaatgt                                               20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
agctcaaccc ttctttaatg                                               20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
cagctcaacc cttctttaat                                               20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
ccagctcaac ccttctttaa                                               20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
accagctcaa cccttcttta                                               20

<210> SEQ ID NO 40
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 40
gaccagctca acccttcttt                                                    20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
ggaccagctc aacccttctt                                                    20

<210> SEQ ID NO 42
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 42
gtccctttct tgtcgatgg                                                     19

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
ccttccctga aggttcctcc                                                    20

<210> SEQ ID NO 44

<400> SEQUENCE: 44

000

<210> SEQ ID NO 45
<211> LENGTH: 20
<212> TYPE: DNA
<213> ORGANISM: Artificial sequence
<220> FEATURE:
<223> OTHER INFORMATION: Primer

<400> SEQUENCE: 45
ggagatgctg cccagaagac                                                    20

<210> SEQ ID NO 46
<211> LENGTH: 20
<212> TYPE: DNA
<213> ORGANISM: Artificial sequence
<220> FEATURE:
<223> OTHER INFORMATION: Primer

<400> SEQUENCE: 46
gctggcggta taggctgaag                                                    20

<210> SEQ ID NO 47
<211> LENGTH: 30
<212> TYPE: DNA
<213> ORGANISM: Artificial sequence
```

```
<220> FEATURE:
<223> OTHER INFORMATION: Probe

<400> SEQUENCE: 47
atcaggatca cccaaccttc aacaagatca                                      30

<210> SEQ ID NO 48
<211> LENGTH: 20
<212> TYPE: DNA
<213> ORGANISM: Artificial sequence
<220> FEATURE:
<223> OTHER INFORMATION: Primer

<400> SEQUENCE: 48
ggagatgctg cccagaagac                                                 20

<210> SEQ ID NO 49
<211> LENGTH: 20
<212> TYPE: DNA
<213> ORGANISM: Artificial sequence
<220> FEATURE:
<223> OTHER INFORMATION: Primer

<400> SEQUENCE: 49
gctggcggta taggctgaag                                                 20

<210> SEQ ID NO 50
<211> LENGTH: 30
<212> TYPE: DNA
<213> ORGANISM: Artificial sequence
<220> FEATURE:
<223> OTHER INFORMATION: Probe

<400> SEQUENCE: 50
atcaggatca cccaaccttc aacaagatca                                      30

<210> SEQ ID NO 51
<211> LENGTH: 21
<212> TYPE: DNA
<213> ORGANISM: Artificial sequence
<220> FEATURE:
<223> OTHER INFORMATION: Primer

<400> SEQUENCE: 51
gaccaccgtg aaggtgccta t                                               21

<210> SEQ ID NO 52
<211> LENGTH: 24
<212> TYPE: DNA
<213> ORGANISM: Artificial sequence
<220> FEATURE:
<223> OTHER INFORMATION: Primer

<400> SEQUENCE: 52
ggacagcttc ttacagtgct ggat                                            24

<210> SEQ ID NO 53
<211> LENGTH: 20
<212> TYPE: DNA
<213> ORGANISM: Artificial sequence
<220> FEATURE:
<223> OTHER INFORMATION: Probe

<400> SEQUENCE: 53
atgaagcgtt taggcatgtt                                                 20
```

```
<210> SEQ ID NO 54
<211> LENGTH: 23
<212> TYPE: DNA
<213> ORGANISM: Artificial sequence
<220> FEATURE:
<223> OTHER INFORMATION: Primer

<400> SEQUENCE: 54
tctttaaagg caaatgggag aga                                              23

<210> SEQ ID NO 55
<211> LENGTH: 20
<212> TYPE: DNA
<213> ORGANISM: Artificial sequence
<220> FEATURE:
<223> OTHER INFORMATION: Primer

<400> SEQUENCE: 55
tgcctaaacg cctcatcatg                                                  20

<210> SEQ ID NO 56
<211> LENGTH: 20
<212> TYPE: DNA
<213> ORGANISM: Artificial sequence
<220> FEATURE:
<223> OTHER INFORMATION: Probe

<400> SEQUENCE: 56
ccacgtggac caggcgacca                                                  20

<210> SEQ ID NO 57
<211> LENGTH: 21
<212> TYPE: DNA
<213> ORGANISM: Artificial sequence
<220> FEATURE:
<223> OTHER INFORMATION: Primer

<400> SEQUENCE: 57
tcatggaaag cctctgtgga t                                                21

<210> SEQ ID NO 58
<211> LENGTH: 16
<212> TYPE: DNA
<213> ORGANISM: Artificial sequence
<220> FEATURE:
<223> OTHER INFORMATION: Primer

<400> SEQUENCE: 58
gcggcccgtg atgaga                                                      16

<210> SEQ ID NO 59
<211> LENGTH: 24
<212> TYPE: DNA
<213> ORGANISM: Artificial sequence
<220> FEATURE:
<223> OTHER INFORMATION: Probe

<400> SEQUENCE: 59
cccacaagtc ccagaaccgc agtg                                             24
```